US009725498B2

(12) United States Patent
Russell et al.

(10) Patent No.: US 9,725,498 B2
(45) Date of Patent: Aug. 8, 2017

(54) DESIGNER COLLAGENS AND USE THEREOF

(71) Applicant: The Texas A&M University System, College Station, TX (US)

(72) Inventors: Brooke H. Russell, Pearland, TX (US); Magnus Hook, Houston, TX (US); Mariah S. Hahn, College Station, TX (US); Elizabeth M. Cosgriff-Hernandez, College Station, TX (US); Neungseon Seo, Carmel, IN (US); Marvin Xuejun Xu, Missouri City, TX (US); Jose J. Rivera, Humble, TX (US); Mary Beth Browning, Houston, TX (US)

(73) Assignee: THE TEXAS A&M UNIVERSITY SYSTEM, College Station, TX (US)

( * ) Notice: Subject to any disclaimer, the term of this patent is extended or adjusted under 35 U.S.C. 154(b) by 130 days.

(21) Appl. No.: 14/095,451

(22) Filed: Dec. 3, 2013

(65) Prior Publication Data
US 2014/0163205 A1 Jun. 12, 2014

Related U.S. Application Data

(63) Continuation of application No. 12/804,306, filed on Jul. 19, 2010, now Pat. No. 8,618,250.

(60) Provisional application No. 61/335,432, filed on Jan. 7, 2010, provisional application No. 61/271,218, filed on Jul. 17, 2009.

(51) Int. Cl.
C07K 14/78 (2006.01)
C07K 16/28 (2006.01)
A61L 15/32 (2006.01)
A61L 27/24 (2006.01)
A61L 27/50 (2006.01)
A61K 38/00 (2006.01)

(52) U.S. Cl.
CPC ............ *C07K 14/78* (2013.01); *A61L 15/325* (2013.01); *A61L 27/24* (2013.01); *A61L 27/507* (2013.01); *A61L 2430/02* (2013.01); *A61L 2430/06* (2013.01); *A61L 2430/34* (2013.01); *C07K 2319/00* (2013.01); *C07K 2319/33* (2013.01); *C07K 2319/70* (2013.01)

(58) Field of Classification Search
CPC ............................ C07K 16/18; C07K 16/2842
See application file for complete search history.

(56) References Cited

U.S. PATENT DOCUMENTS

| 6,150,081 | A  | 11/2000 | Van Heerde et al. |
| 6,171,827 | B1 | 1/2001  | Bulleid et al. |
| 7,504,490 | B1 | 3/2009  | Weinstock et al. |
| 7,745,391 | B2 | 6/2010  | Minz et al. |
| 8,618,250 | B2 | 12/2013 | Russell et al. |
| 2003/0064436 | A1* | 4/2003 | Vaughan ............... C07K 14/78 435/69.1 |
| 2004/0214282 | A1* | 10/2004 | Hook ................... C07K 14/315 435/69.1 |
| 2006/0035336 | A1 | 2/2006 | Hook et al. |
| 2006/0083730 | A1* | 4/2006 | Kusanagi ............ A61F 2/30756 424/94.1 |
| 2007/0099244 | A1 | 5/2007 | Xu et al. |
| 2008/0014613 | A1* | 1/2008 | Hook .................... C07K 14/78 435/69.1 |
| 2008/0139477 | A1* | 6/2008 | Vaughan ............... C07K 14/78 435/69.1 |
| 2009/0169615 | A1* | 7/2009 | Pinsky .................... A61K 8/14 424/450 |
| 2009/0203627 | A1* | 8/2009 | Hook .................... C07K 14/78 514/21.5 |

FOREIGN PATENT DOCUMENTS

WO 2011/008303 A2 1/2011

OTHER PUBLICATIONS

Xu et al. (2002) Streptococcal ScI1 and ScI2 Proteins Form Collagen-like Triple Helices, J. Biol. Chem., vol. 277, pp. 27312-27318.*
Zeltz et al. (2014) Molecular composition and function of integrin-based collagen glues—Introducing COLINBRIs, Biochem. Biophy. Acta, vol. 1840, pp. 2533-2548).*
Knight et al. (2000) The Collagen-binding A-domains of Integrins a1b1 and a2b1 Recognize the Same Specific Amino Acid Sequence, GFOGER, in Native (Triple-helical) Collagens, J. Biol. Chem., vol. 275, pp. 35-40.*
Caswell, et al., "Identification of the First Prokaryotic Collagen Sequence Motif that Mediates Binding to Human Collagen Receptors, Integrins α2β1 and α11β1," The Journal of Biological Chemistry, Dec. 26, 2008, vol. 283, No. 52, pp. 36168-36175.
Hoe, et al., "Characterization of the Immune Response to Collagen-Like Proteins ScI1 and ScI2 of Serotype M1 and M28 Group A *Streptococcus*," FEMS Microbiol Lett, (First published online Oct. 24, 2007), pp. 142-149.
Humtsoe, et al., "A Streptococcal Collagin-Like Protein Interacts with the α2β1 Integrin and Induces Intracellular Signaling," The Journal of Biological Chemistry, (Apr. 8, 2005), vol. 280, No. 14, pp. 13848-13857.
Kim, et al., "A Novel Binding Site in Collagen Type III for Integrins α1β1 and α2β1," The Journal of Biological Chemistry, Sep. 16, 2005, vol. 280, No. 37, pp. 32512-32520.

(Continued)

*Primary Examiner* — Anand Desai
*Assistant Examiner* — Samuel Liu
(74) *Attorney, Agent, or Firm* — Chainey P. Singleton; Edwin S. Flores; Chalker Flores, LLP

(57) ABSTRACT

The present disclosure provides synthetic collagen and methods of making and using synthetic collagen that include a synthetic collagen that facilitates wound closure comprising an isolated and purified triple helical backbone protein that facilitates wound closure comprising one or more alteration in a triple helical backbone protein sequence, that stabilize the isolated and purified triple helical backbone protein and does not disrupt an additional collagen ligand interaction; and one or more integrin binding motifs, wherein the isolated and purified triple helical backbone protein facilitates wound closure.

16 Claims, 27 Drawing Sheets

(56) References Cited

OTHER PUBLICATIONS

Mohs, et al., "Mechanism of Stabilization of a Bacterial Collagen Triple Helix in the Absence of Hydroxyproline," The Journal of Biological Chemistry, Oct. 12, 2007, vol. 282, No. 41, pp. 29757-29765.

Raynal, et al., "Use of Synthetic Peptides to Locate Novel Integrin α2β1-Binding Motifs in Human Collagen III," The Journal of Biological Chemistry, Feb. 17, 2006, vol. 281, No. 7, pp. 3821-3831.

Sweeney, et al., "Angiogenesis in Collagen I Requires α2β1 Ligation of a GFP*GER Sequence and Possibly p38 MAPK Activation and Focal Adhesion Disassembly," The Journal of Biological Chemistry, Aug. 15, 2003, vol. 278, No. 33, pp. 30516-30524.

Xu, et al., "Multiple Binding Sites in Collagen Type I for the Integrins α1β1 and α2β1," The Journal of Biological Chemistry, Dec. 15, 2000, vol. 275, No. 50, pp. 38981-38989.

Xu, et al., "Streptococcal Sc11 and Sc12 Proteins form Collagen-Like Triple Helices," The Journal of Biological Chemistry, Jul. 26, 2002, vol. 277, No. 30, pp. 27312-27318.

Yoshizumi, et al., "Self-Association of *Streptococcus* Pyogenes Collagen-Like Constructs into Higher Order Structures," Protein Science, (Published online Apr. 16, 2009), vol. 18:1241-1251.

Korean Intellectual Property Office (ISA), International Search Report for PCT/US2010/002029, dated Apr. 26, 2011, 6 pages.

Korean Intellectual Property Office (ISA), International Preliminary Report on Patentability for PCT/US2010/002029, dated Apr. 25, 2011, 6 pages.

European Patent Office, Extended European Search Report for EP Appl. No. 10800176.9 dated Mar. 30, 2012, 6 pp.

Han, et al. "Assessment of prokaryotic collagen-like sequences derived from streptococcal ScI1 and ScI2 proteins as a source of recombinant GXY polymers" Appl Microbiol Biotechnol (Published online Mar. 22, 2006) 72: 109-115.

Seo, et al. "An Engineered α1 Integrin-binding Collagenous Sequence" The Journal of Biological Chemistry, vol. 285, No. 40, pp. 31046-31054, Oct. 1, 2010.

\* cited by examiner

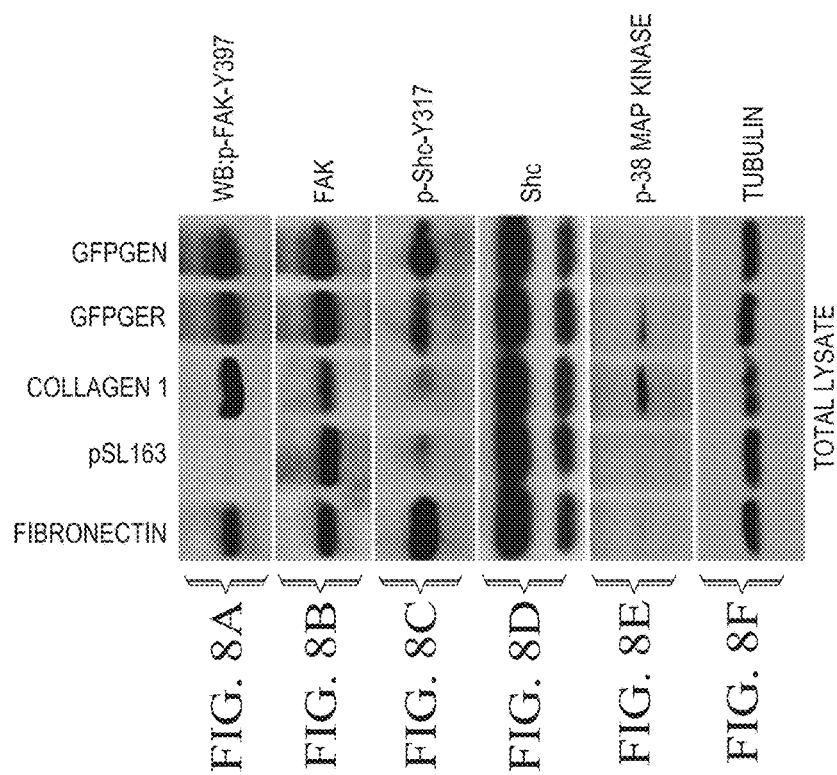
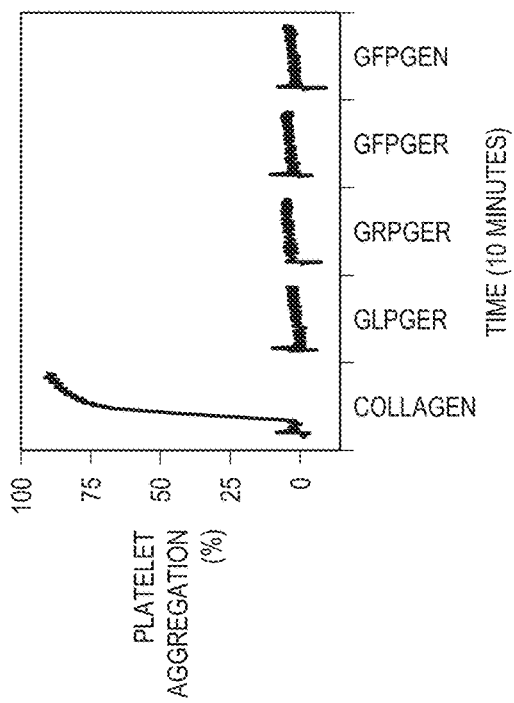
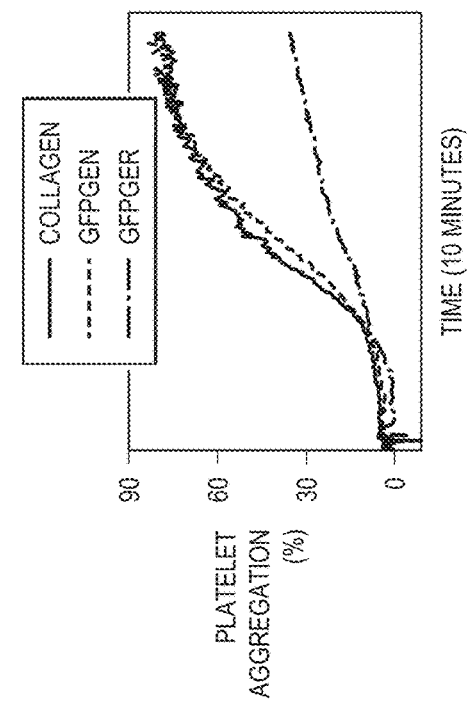

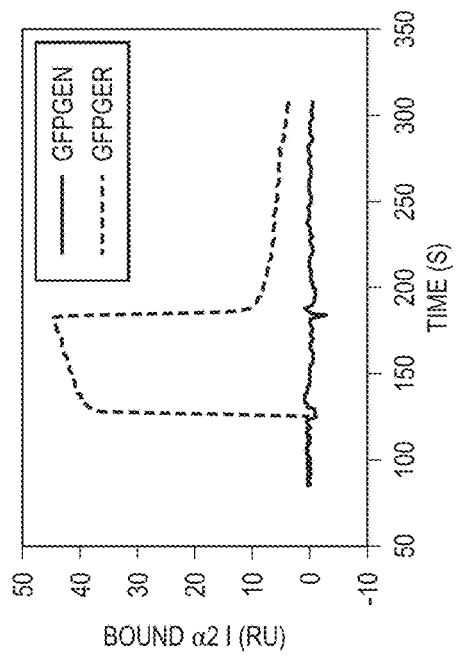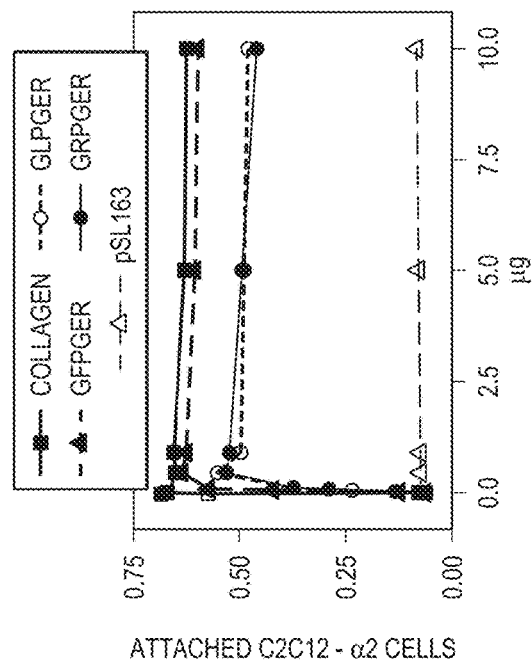
FIG. 7A
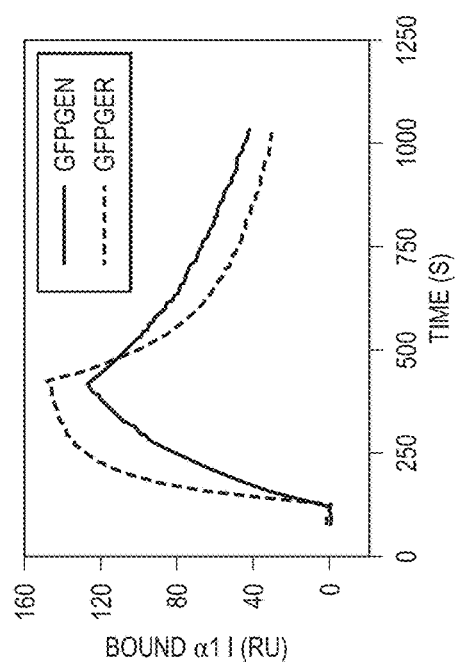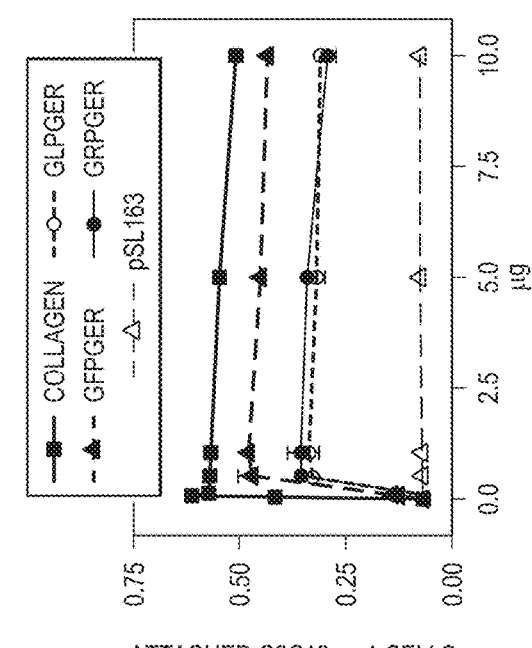
FIG. 7B

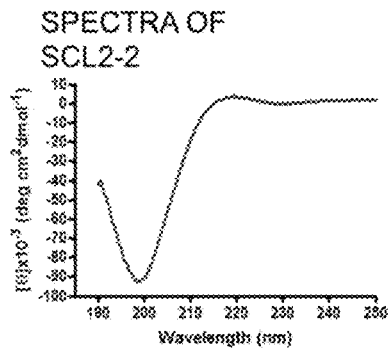
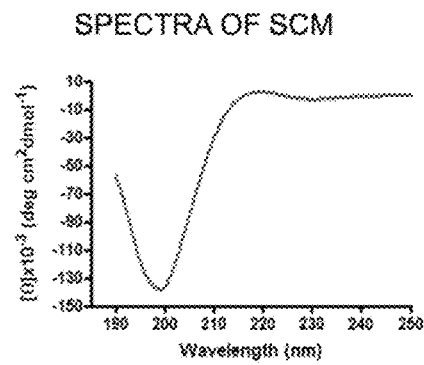
Fig. 20A
Fig. 20B
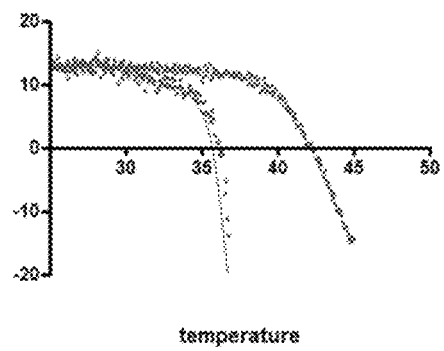
Fig. 20C
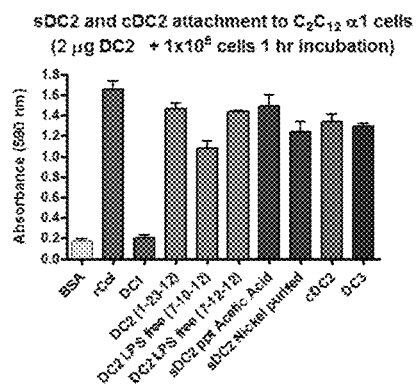
Fig. 21

DESIGNER COLLAGENS AND USE THEREOF

CROSS-REFERENCE TO RELATED APPLICATIONS

This Non-Provisional Patent application is a Continuation-in-Part and claims priority based on U.S. patent application Ser. No. 12/804,306, filed Jul. 19, 2010, which claims priority to U.S. Provisional Application Ser. No. 61/335,432 and U.S. Ser. No. 61/271,218, the entire contents of which are incorporated herein by reference.

STATEMENT OF FEDERALLY FUNDED RESEARCH

None.

REFERENCE TO A SEQUENCE LISTING

The present application includes a Sequence Listing filed separately as required by 37 CFR 1.821-1.825.

TECHNICAL FIELD OF THE INVENTION

The present invention relates generally to the field of collagen-mimetic protein and interaction of extracellular matrix protein with receptors and cell signaling. More specifically, the present invention relates to collagen-mimetic protein used in wound dressing.

BACKGROUND OF THE INVENTION

Without limiting the scope of the invention, its background is described in connection with novel collagen-mimetic protein and bioactive hydrogels containing collagen-mimetic protein having structure characteristic of native collagen but lacking collagen's array of cell adhesion, cytokine binding, and enzyme-cleavage sites to allow directed engineering to specify functional activity.

Collagen is a major component of the extracellular matrix (ECM). At least 27 genetically different collagen types have been identified, each containing at least one dominant collagenous domain. These collagenous domains have a characteristic triple helix structure formed by repeating Gly-X-Y sequences in each participating chain where X often is Proline and Y is hydroxyproline. The collagen monomers often assemble into more complex structures of varying organizations such as fibrils (types I-III, V and XI), networks (types IV, VIII and X) and beaded filaments (type VI). The fibrillar collagen types I and III are the major structural components of the extracellular matrix of skin, cardiac and vascular tissues, whereas type II collagen is a major structural component of cartilage. In addition to contributing to the structural integrity of the tissues, collagens also affect cell behavior through interactions with other matrix proteins and cellular receptors.

The integrins are a family of heterodimeric cell surface receptors involved in cell-cell and cell-substrate adhesion. They act as bridging molecules that link intracellular signaling molecules to the extracellular matrix through bi-directional signaling and control cell behavior and tissue architecture. Four integrins, $\alpha1\beta1$, $\alpha2\beta1$, $\alpha10\beta1$ and $\alpha11\beta1$ have been shown to bind collagens. Collagen integrin interactions play a role in normal and pathological physiology and directly affect cell adhesion, migration, proliferation and differentiation as well as angiogenesis, platelet aggregation and extracellular matrix assembly. However, the precise molecular mechanisms that lead to these activities are not understood.

Collagen binding by the four integrins is mediated by a ~200 amino acids long so-called inserted domain (I domain) found between blades 2 and 3 of the $\beta$-propeller domain of the $\alpha$ chains. All four I domains ($\alpha_1 I$, $\alpha_2 I$, $\alpha_{10} I$, $\alpha_{11} I$) contain a metal ion-dependent adhesion site (MIDAS) that is required for coordinating a divalent cation and is essential for collagen binding. Synthetic collagen peptides containing the type I collagen derived sequences, GFOGER (SEQ ID NO: 1) or GLOGER (SEQ ID NO: 2) bind with high affinity to $\alpha_1 I$, $\alpha_2 I$ and $\alpha_{11} I$; furthermore, synthetic peptides containing these sequences inhibit the binding of I domains to intact collagens. The crystal structures of apo-$\alpha_2 I$ and $\alpha_2 I$ in complex with a collagen peptide containing the GFOGER (SEQ ID NO: 1) sequence have been solved and showed that the apo-$\alpha_2 I$ adopted an inactive "closed" conformation and the ligand bound $\alpha_2 I$, an active "open" conformation. The Glu residue in the collagen peptide was shown in the structure of the complex to directly interact with a $Mg^{2+}$ ion coordinated by the MIDAS motif and the Arg residue forms a salt bridge with D219 in $\alpha_2 I$. The importance of the GER sequence in collagen for integrin binding was confirmed by mutagenesis studies, which showed that replacing Glu in the collagen peptide with an Asp residue completely abolished the binding whereas replacing the Arg with a Lys residue reduced the binding by 50%. The Phe residue in the collagen sequence appeared to participate in hydrophobic interactions with $\alpha_2 I$ and could be replaced by Leu. Both GFOGER (SEQ ID NO: 1) and GLOGER (SEQ ID NO: 2) bind to $\alpha_1 I$ and $\alpha_2 I$ (Xu et al., 2000). However, changing the Phe residue to a Met or an Ala reduced the apparent affinity of I domains (Siljander et al., 2004). GASGER (SEQ ID NO: 3) was also reported to be recognized by the I domains but bound with lower affinity than GFOGER (SEQ ID NO: 1) and GLOGER (SEQ ID NO: 2) (Zhang et al., 2003; Siljander et al., 2004; Xu et al., 2000). Therefore, GFOGER (SEQ ID NO: 1) and GLOGER (SEQ ID NO: 2) are the only two known collagen-derived sequence motifs that support high affinity binding by the collagen-binding I domains. However, the GFOGER (SEQ ID NO: 1) and GLOGER (SEQ ID NO: 2) motifs are absent in some collagens such as human type III collagen. Additionally, CHO cell expressing $\alpha1\beta1$ and $\alpha2\beta1$ could adhere and spread on human type III collagen and furthermore, the recombinant proteins of $\alpha1I$ and $\alpha2I$ could bind to this collagen type.

Collagen and its derivative, gelatin, have been used in medical, pharmaceutical and consumer products for more than 100 years. Collagen biomaterials approved for use in humans are predominantly obtained from animal sources. Animal derived collagens have a risk of immunogenecity and have a risk of contamination with pathogens such as viruses and prions, which cause the human form of mad cow disease. These limitations can be overcome by recombinant protein expression technologies. Several groups have generated recombinant collage type I or III from expression systems utilizing, mammalian, insect, yeast, and plant cells. However, these materials are not currently in clinical trials. These materials have several limits including high cost and low yields. Regardless of how these collagens are obtained, the collagen molecule contains molecular properties that differ widely in function. The introduction of this plethora of different properties can cause an adverse reaction on a molecular level that can lead to scar tissue formation, immunogenic effects, adhesion production, and thrombosis. Thus, there is a need in the art for collagen biomaterials that are devoid of or having reduced undesirable effects including risk of immunogenicity. The present invention fulfills this long-standing need and desire in the art.

SUMMARY OF THE INVENTION

The present disclosure provides a synthetic collagen that facilitates wound closure comprising an isolated and purified triple helical backbone protein that facilitates wound closure comprising one or more alteration in a triple helical backbone protein sequence, that stabilize the isolated and purified triple helical backbone protein and does not disrupt an additional collagen ligand interaction; and one or more integrin binding motifs, wherein the isolated and purified triple helical backbone protein facilitates wound closure.

The isolated and purified triple helical backbone protein may be produced in a prokaryotic expression system and the triple helical backbone may be derived from a Streptococcal protein. The one or more integrin binding motifs may be one or more GXY collagen-like repeats and have a collagen ligand binding affinity that is altered. The collagen ligand may be an integrin or a $\alpha1\beta1$. The isolated and purified triple helical backbone protein may have a higher melting temperature than an unmodified triple helical backbone protein. The isolated and purified triple helical backbone protein may be supported by a matrix and the matrix may be a polymer matrix, e.g., the polymer matrix is a poly(ethylene glycol) hydrogel. Alternatively, the matrix may be an acellular derived mammalian matrix. The isolated and purified triple helical backbone protein may be formed into a vascular graft, a wound dressing, or matrices for bone and cartilage regeneration. More specifically, the isolated and purified triple helical backbone protein may be formed into a lumen of a vascular graft. The isolated and purified triple helical backbone protein binds a fibronectin and the fibronectin may be in an acellular matrix derived from mammals. Although the composition may be in various forms and formulations one such composition is a topical composition.

Another embodiment of the present disclosure provides a hybrid collagen matrix having an acellular derived mammalian matrix; an isolated and purified triple helical backbone protein in contact with the acellular derived mammalian matrix to form an acellular-collagen hybrid matrix, wherein the isolated and purified triple helical backbone protein comprises one or more alteration in a triple helical backbone protein sequence that stabilize the isolated and purified triple helical backbone protein and does not disrupt an additional collagen ligand interaction and one or more integrin binding motifs, wherein the isolated and purified triple helical backbone protein facilitates tissue regeneration through cell infiltration.

The isolated and purified triple helical backbone protein binds a fibronectin and the fibronectin may be in an acellular matrix derived from mammals, e.g., human cadaver, animal, etc. The acellular-collagen hybrid matrix is in the form of a vascular graft, a chronic wound dressing, a matrices for bone regeneration or a matrices for cartilage regeneration or a matrices for soft tissue repair. The isolated and purified triple helical backbone protein may be produced in a prokaryotic expression system and the triple helical backbone may be derived from a Streptococcal protein. The one or more integrin binding motifs may be one or more GXY collagen-like repeats and have a collagen ligand binding affinity that is altered. The collagen ligand may be an integrin or a $\alpha1\beta1$. The isolated and purified triple helical backbone protein may have a higher melting temperature than an unmodified triple helical backbone protein.

Another embodiment of the present disclosure provides includes a hybrid collagen hydrogel matrix comprising a polymer matrix; an isolated and purified triple helical backbone protein linked to the polymer matrix to form a hybrid collagen hydrogel matrix, wherein the isolated and purified triple helical backbone protein comprises one or more integrin binding motifs and one or more alteration in a triple helical backbone protein sequence, wherein the one or more alteration in a triple helical backbone protein sequence stabilize the isolated and purified triple helical backbone protein and does not disrupt an additional collagen ligand interaction, and wherein the isolated and purified triple helical backbone protein and the polymer matrix are linked away from the one or more integrin binding motifs.

The isolated and purified triple helical backbone protein may be produced in a prokaryotic expression system and the triple helical backbone may be derived from a Streptococcal protein. The one or more integrin binding motifs may be one or more GXY collagen-like repeats and have a collagen ligand binding affinity that is altered. The collagen ligand may be an integrin or a $\alpha1\beta1$. The isolated and purified triple helical backbone protein may have a higher melting temperature than an unmodified triple helical backbone protein. The matrix may be a polymer matrix, e.g., the polymer matrix is a poly(ethylene glycol) hydrogel.

Another embodiment of the present disclosure provides method of tissue integration by providing an acellular derived mammalian matrix; contacting the acellular derived mammalian matrix with an isolated and purified triple helical backbone protein, wherein the isolated and purified triple helical backbone protein comprises one or more alteration in a triple helical backbone protein sequence that stabilize the isolated and purified triple helical backbone protein and does not disrupt an additional collagen ligand interaction and one or more integrin binding motifs, wherein the isolated and purified triple helical backbone protein and the acellular derived mammalian matrix integrate together.

The isolated and purified triple helical backbone protein may be produced in a prokaryotic expression system and the triple helical backbone may be derived from a Streptococcal protein. The one or more integrin binding motifs may be one or more GXY collagen-like repeats and have a collagen ligand binding affinity that is altered. The collagen ligand may be an integrin or a $\alpha1\beta1$. The isolated and purified triple helical backbone protein may have a higher melting temperature than an unmodified triple helical backbone protein. The isolated and purified triple helical backbone protein may be supported by a matrix and the matrix may be a polymer matrix, e.g., the polymer matrix is a poly(ethylene glycol) hydrogel. Alternatively, the matrix may be an acellular derived mammalian matrix. The isolated and purified triple helical backbone protein may be formed into a vascular graft, a wound dressing, or matrices for bone and cartilage regeneration. More specifically, the isolated and purified triple helical backbone protein may be formed into a lumen of a vascular graft. The isolated and purified triple helical backbone protein binds a fibronectin and the fibronectin may be in an acellular matrix derived from mammals. Although the composition may be in various forms and formulations one such composition is a topical composition.

BRIEF DESCRIPTION OF THE DRAWINGS

For a more complete understanding of the features and advantages of the present invention, reference is now made to the detailed description of the invention along with the accompanying figures and in which:

FIG. 13A shows Coomassie-stained 12% SDS-PAGE analysis of functionalized Designer Collagens (P163 Control, P163-F, GFPGER-F, (SEQ ID NO:10) GFP-GEN-F (SEQ ID NO:11)) with and without heat denaturation. FIG. 13B shows that functionalized Designer Collagens demonstrate a typical peak at 220 nm in the circular dichroism (CD) spectra indicative of a triple helical structure. FIG. 13C shows a representative thermal transition of functionalized Designer Collagen monitored at 220 nm indicating an alteration in protein conformation at ~37° C.

FIGS. 20A and 20B are images of circular dichroism spectra of SCL2-2 and stable collagen-mimetic (SCM). The peak at 220 nm in the plot is indicative of the formation of a triple helix structure. FIG. 20C is a plot of the thermal transitions of Scl2-2 (red crossing 0 at 36) and SCM (green crossing 0 at 42).

FIG. 21 is a graph of cell adherence of collagen mimetics to substrates for C2C12 cell adherence.

DETAILED DESCRIPTION OF THE INVENTION

Figure 1:
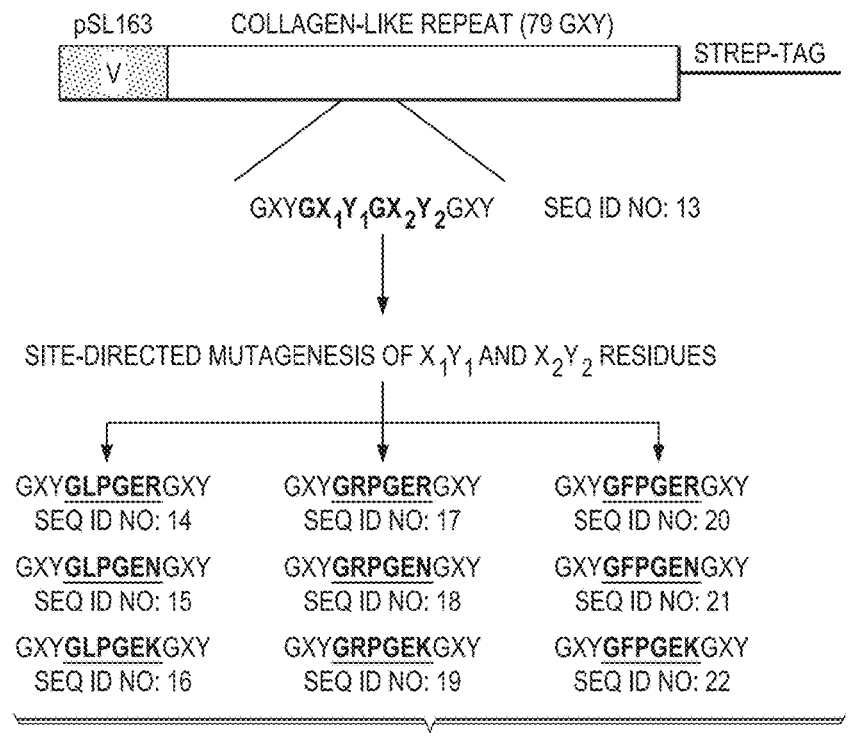
FIG. 1 shows pSL163, a collagen-like protein from Group A *Streptococcus* used as a template to insert receptor-binding motifs by site-directed mutagenesis to change the attachment of the endothelial cells, as did type I Collagen.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The present invention has identified the design, production and use of "designer collagens". Designer Collagens encompass the following characteristics: a triple helical backbone protein produced in a prokaryotic expression system with an 'inserted' biologically active sequence(s).

The triple helical backbone is derived from a Streptococcal protein and is considered collagen-like. 'Inserted' sequences are generated by standard molecular biologically techniques, including computer modeling and site-directed mutagenesis. Biologically active sequences impart a specific function to another molecule or cell with a desired effect. An example of an 'inserted' biologically active sequence is an integrin binding motif.

Collagen is a major component of the extracellular matrix and it functions to provide tensile strength to tissues as well as influence cell behavior through interactions with cellular receptors. Collagen has been used as a biomaterial in medical, pharmaceutical and consumer products for more than one hundred years. Collagen biomaterials approved for use in humans are predominantly derived from animal sources and have certain limits. These limitations can be overcome by advances in collagen-cell interactions and recombinant protein expression technologies. Designer Collagens as biomaterials have the potential to improve collagen's use in current markets and also Designer Collagens may be used in markets where collagen is not considered an optimal biomaterial. Designer Collagens are highly purified, fully characterized, and can be genetically customized to exhibit desired features for particular applications of interest including presentation of receptor binding motifs.

Thus, in one embodiment of the present invention, there is provided a recombinant synthetic collagen. This recombinant synthetic collagen contains a triple helical backbone protein produced in a prokaryotic expression system. Preferably, the protein contains at least one 'inserted' biologically active sequence(s). In one preferred form, the recombinant synthetic collagen has a triple helical backbone derived from a Streptococcal protein. Preferably, the Streptococcal protein contains a collagen-like repeat of GXYGX1Y1GX2Y2GXY (SEQ ID NO: 13) and wherein the recombinant synthetic collagen is created by changing X1 position to L, R, or F residues or Y2 position to R, K, or N residues. In one preferred form, the biologically active sequence is an integrin binding motif Generally, the recombinant synthetic collagen of the present invention are capable of binding to integrins α1β1 and/or α2β1 without hydroxyproline.

In the recombinant synthetic collagen of the present invention, representative biologically active sequences are GLPGER (SEQ ID NO: 4), GLPGEN (SEQ ID NO: 5), GLPGEK (SEQ ID NO: 6), GRPGER (SEQ ID NO: 7), GRPGEN (SEQ ID NO: 8), GRPGEK (SEQ ID NO: 9), GFPGER (SEQ ID NO: 10), GFPGEN (SEQ ID NO: 11), or GFPGEK (SEQ ID NO: 12). In one form, the recombinant synthetic collagen of the present invention are produced in a bacterial expression system deficient in post-translational modification.

Particularly, in a related embodiment, the present invention therefore provides the specific biologically active motif sequences of the recombinant synthetic collagen shown in GLPGER (SEQ ID NO: 4), GLPGEN (SEQ ID NO: 5), GLPGEK (SEQ ID NO: 6), GRPGER (SEQ ID NO: 7), GRPGEN (SEQ ID NO: 8), GRPGEK (SEQ ID NO: 9), GFPGER (SEQ ID NO: 10), GFPGEN (SEQ ID NO: 11), and GFPGEK (SEQ ID NO: 12).

As is described in detail infra, the recombinant synthetic collagen of the present invention may be designed to have a variety of functions. For example, the collagen containing sequences GLPGER (SEQ ID NO: 4), GRPGER (SEQ ID NO: 7), or GFPGER (SEQ ID NO: 10)), support adherence of both α1β1 and α2β1, spreading of endothelial cells, fibroblasts, chondrocytes, and smooth muscle cells. Also, the collagen containing sequence GFPGER (SEQ ID NO: 10) support adherence and spread of mesenchymal stem cells and adipocyte stem cells. In addition, the collagen containing sequences GFPGER (SEQ ID NO: 10) and GFPGEN (SEQ ID NO: 11) support adherence and spread of mesenchymal stem cells.

In one embodiment, the present invention provides a recombinant synthetic collagen containing a GFPGEN (SEQ ID NO:11) sequence selectively bind to integrin α1β1, but not to α2β1. This recombinant synthetic collagen supports adherence of endothelial cells, fibroblasts, and chondrocytic cells, but does not support adherence of smooth muscle cells.

In another embodiment, the present invention provides a recombinant synthetic collagen containing GLPGER (SEQ ID NO:4), GRPGER (SEQ ID NO:7), GFPGER (SEQ ID NO:10), or GFPGEN (SEQ ID NO:11) sequences. Such recombinant synthetic collagens do not aggregate platelets and are non-thrombogenic.

In another embodiment, the present invention provides a recombinant synthetic collagen containing a GFPGER (SEQ ID NO:10) sequence. Such a recombinant synthetic collagen inhibits collagen-induced platelet aggregation. In another embodiment, the present invention provides a recombinant synthetic collagen containing a GFPGEN (SEQ ID NO:11) sequence. Such a recombinant synthetic collagen does not inhibit collagen-induced platelet aggregation. In another embodiment, the present invention provides a recombinant synthetic collagen containing one, two, three, four and/or five multiple cell binding motifs. Such recombinant synthetic collagens have a density dependent increase in integrin affinity, cell binding, and cell migration. In another embodiment, the present invention provides a recombinant synthetic collagen containing one, two, three, four and/or five GLPGER (SEQ ID NO: 4) cell binding motifs.

In another embodiment, the present invention provides a recombinant synthetic collagen wherein said collagen is affixed to or linked in a chemical manner to a scaffold with intrinsic tensile properties. A person having ordinary skill in this art would readily recognize useful scaffolds but representative examples include but are not limited to PEG-containing hydrogels, ECM components, and mesh materials.

In another embodiment, the present invention provides a recombinant synthetic collagen containing a triple helical backbone protein produced in a prokaryotic expression system. In another embodiment, the present invention provides a recombinant synthetic collagen further comprising an insert selected from the group consisting of but not limited to bone sialoprotein binding sequences, von Willibrand factor, integrins α10β1 and α11β1 binding sequences, and an extracellular matrix constituent.

The following example(s) are given for the purpose of illustrating various embodiments of the invention and are not meant to limit the present invention in any fashion.

Example 1

Designer Collagens produced in a bacterial expression system bind to integrin α1β1 and/or α2β1 and as substrates support adherence and spreading of multiple cell types.

Post-translational modification of collagen to include hydroxyproline residues is important to stabilize the triple helical conformation of collagen. Hydroxyproline has also been implicated in collagen binding to integrins, including α1β1 and α2β1. For example, unhydroxylated collagen produced in plants shows reduced binding affinity for integrin α1β1 and failed to bind α2β1. Adhesion of platelets on unhydroxylated collagen via integrin α2β1 is weaker than on hydroxylated collagen and unhydroxylated collagen fails to induce platelet aggregation. This data suggests that hydroxyproline on collagen is essential for high affinity binding to α1β1 and α2β1. A molecular mechanism detailing the binding differences of unhydroxylated and hydroxylated collagen to integrins α1β1 and α2β1 is unknown. Therefore, the present invention describes new materials capable of binding to integrins α1β1 and α2β1 without hydroxyproline.

Designer Collagens with 'inserted' biologically active sequences, GLPGER (SEQ ID NO: 4), GLPGEN (SEQ ID NO: 5), GLPGEK (SEQ ID NO: 6), GRPGER (SEQ ID NO: 7), GRPGEN (SEQ ID NO: 8), GRPGEK (SEQ ID NO: 9), GFPGER (SEQ ID NO: 10), GFPGEN (SEQ ID NO: 11), GFPGEK (SEQ ID NO: 12), were produced in a bacterial expression system, which is deficient in post-translational modification, including hydroxylation of proline and lysine residues. Designer Collagens with 'inserted' sequences (GLPGER (SEQ ID NO: 4), GRPGER (SEQ ID NO: 7), and GFPGER (SEQ ID NO: 10)), however, support adherence of both α1β1 and α2β1 regardless of the lack of hydroxyproline. This conclusion was reached by ELISA-based assays and Surface Plasmon Resonance analysis. Since many cell types express αβ1 and α2β1, Designer Collagens support adherence and spreading of different cell types including endothelial cells, fibroblasts, chondrocytes, and smooth muscle cells. Cell adherence was quantified and cell morphology was evaluated using fluorescence microcopy techniques.

Example 2

Designer Collagens with a GFPGEN (SEQ ID NO: 11) residue sequence selectively bind to integrin α1β1, but not to α2β1. Selective binding was determined by ELISA-based assays and Surface Plasmon Resonance analysis. The Designer Collagen with GFPGEN (SEQ ID NO: 11) as a substrate supports adherence of endothelial cells, fibroblasts, and chondrocytic cells, but does not support adherence of smooth muscle cells.

Example 3

The Designer Collagens are non-thrombogenic. Collagen is one of several agonists that can activate platelets by the binding of specific sequences, GFOGER (SEQ ID NO: 1) and/or GLOGER (SEQ ID NO: 2), to integrin α2β1 on platelets. Designer Collagens with residue motifs GLPGER (SEQ ID NO: 4), GRPGER (SEQ ID NO: 7), GFPGER (SEQ ID NO: 10), and GFPGEN (SEQ ID NO: 11) were tested in platelet aggregation assays to determine whether they activate platelets. Designer Collagens do not aggregate platelets at 10-fold higher concentrations than native collagen in platelet aggregation assays. This data indicates that these Designer Collagens are completely non-thrombogenic although they contain sequences that are derived from native collagen, which act as an agonist for platelet aggregation.

Designer Collagens were tested in platelet aggregation inhibition assays to determine whether they can inhibit collagen-induced platelet aggregation. Designer Collagens with GFPGER (SEQ ID NO: 10) inhibits collagen-induced platelet aggregation indicating that Designer Collagens with GFPGER competes with native collagen to bind α2β1 without aggregating platelets. The Designer Collagen with GFPGER is an antagonist to inhibit collagen-induced platelet aggregation via the blocking of α2β1 integrin. The Designer Collagen with a GFPGEN (SEQ ID NO: 11) residue sequence did not inhibit collagen-induced platelet aggregation since the Designer Collagen only binds to integrin α1β1 that is not normally expressed on platelets. The Designer Collagen with GFPGEN (SEQ ID NO: 11) would be an ideal biomaterial for vascular applications.

The introduction of one, two, three, four and/or five multiple cell binding motifs results in a density dependent increase in integrin affinity, cell binding, and cell migration. This was determined by comparing Designer Collagens with one, two, three, four and five GLPGER cell binding motifs. Integrin affinity was assessed by surface plasmon resonance. Cell binding and migration was demonstrated with human umbilical vein endothelial cells.

Example 4

Construction of Designer Collagens. Bacterial collagen-like proteins derived from Group A *Streptococcus* have been used as a template to produce Designer Collagens with inserted motifs with specific functions. The functional motifs have receptor binding activities through an interaction with collagen binding integrins, α1β1 and α2β1. These proteins are termed Designer Collagens and they include the following characteristics: humanized collagen fragments or fragments generated through computer modeling that are inserted into a bacterial collagen-like backbone and produced in a prokaryotic expression system. pSL163, a collagen-like protein from Group A *Streptococcus* was used as a template to insert receptor-binding motifs. Site-directed mutagenesis was performed to change X1 position to L, R, or F residues or and X2 position to R, K, or N residues (FIG. 1). These constructs were expressed in *E. coli* and recombinant proteins were purified. The library of Designer Collagens contains recombinant proteins with the following receptor-binding motifs: GLPGER (SEQ ID NO: 4), GRPGER (SEQ ID NO: 7), GFPGER (SEQ ID NO: 10), GLPGEN (SEQ ID NO: 5), GRPGEN (SEQ ID NO: 8), GFPGEN (SEQ ID NO: 11), GLPGEK (SEQ ID NO: 12), GRPGEK (SEQ ID NO: 9), and GFPGEK (SEQ ID NO: 12). The present invention characterized the identity and purity of these recombinant proteins using SDS-PAGE, Western-blot analysis, and Circular Dichroism spectroscopy. All of these proteins formed a triple helical structure. The binding of the Designer Collagens with residue sequences of GLPGER (SEQ ID NO: 4), GRPGER (SEQ ID NO: 7), GFPGER (SEQ ID NO: 10), GLPGEN (SEQ ID NO: 5), GRPGEN (SEQ ID NO: 8), GFPGEN (SEQ ID NO: 11), GLPGEK (SEQ ID NO: 12), GRPGEK (SEQ ID NO: 9), and GFPGEK (SEQ ID NO: 12), to α1 and α2 I domains were examined in ELISA-based assays. The binding of Designer Collagens with residue sequences of GFPGER (SEQ ID NO: 10), GRPGER (SEQ ID NO: 7), GLPGER (SEQ ID NO: 4), and GFPGEN (SEQ ID NO: 11) was tested using Surface Plasmon Resonance analysis using a BIAcore 3000 machine. C2C12 cells, derived from a mouse myoblast cell line, lack expression of the α-subunit of collagen binding integrins α1β1, α2β1, α10β1, and α11β1. These cells can be utilized to determine the individual contribution of integrin binding to a substrate. The a subunits are stably expressed in individual cells line, C2C12-α1 and C2C12-α2. Whether immobilized Designer Collagens in the library support adherence and spreading of these cell types was tested. In addition, endothelial cells, fibroblasts, chondrocytic cells, and smooth muscle cells were tested in adherence and spreading assays. The ability of cells to migrate on immobilized Designer Collagens in 96 well plates, tissue culture chamber slides, or modified migration assays plates was determined. The Designer Collagens were also tested in platelet aggregation assays to determine whether the Designer Collagens bind and activate platelets.

Based on the experimental data, proteins with unique and novel characteristics were demonstrated. The Designer Collagen with GFPGEN (SEQ ID NO: 11) residues is a biomaterial for vascular applications. The Designer Collagen with GFPGER (SEQ ID NO: 10) residues is an antagonist, which blocks interaction of collagen with α2β1 on platelets. The Designer Collagen with GFPGER (SEQ ID NO: 10) residues can interact with α1α1 and α2β1 and therefore may be a cell recruiting molecule with applications in angiogenesis, wound healing, and orthopedics.

Designer Collagens need to be biocompatible and non-immunogenic in humans, which will be addressed using appropriate animal models before clinical trials. Modification of certain portions of Designer Collagen may be required for appropriate use in humans. Designer Collagens are proteins that do not naturally form higher ordered structures such as fibers; therefore, Designer Collagens lack intrinsic tensile properties or a three-dimensional structure. Designer Collagens may need to be affixed to or linked in a chemical manner to a scaffold with intrinsic tensile properties. Currently, PEG-containing hydrogels, ECM components, and mesh materials may be used as scaffolds.

Example 5

Figure 2A:
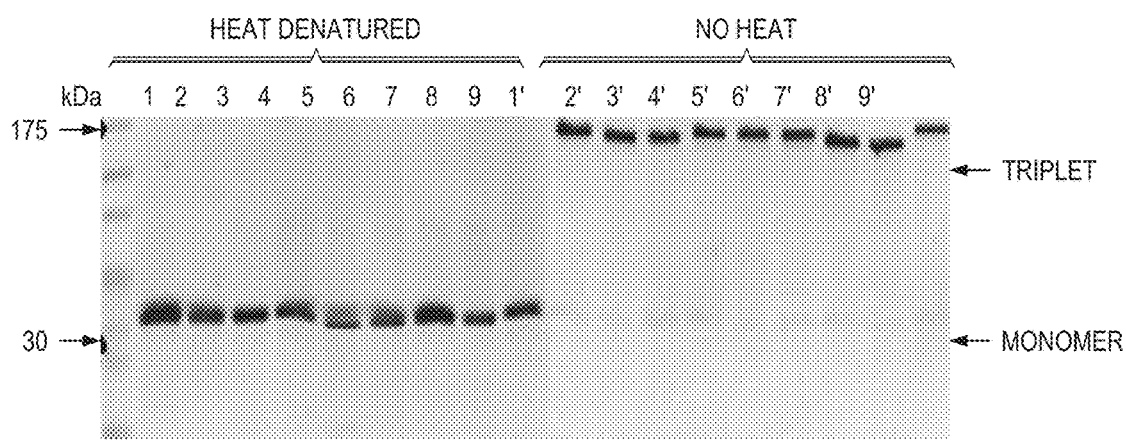
Figure 2B:
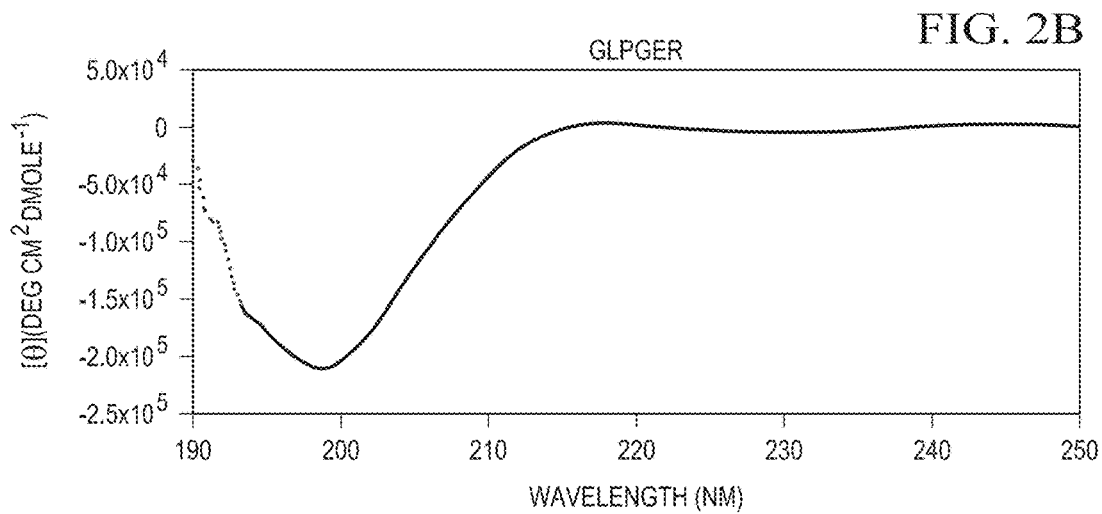
Figure 2C:
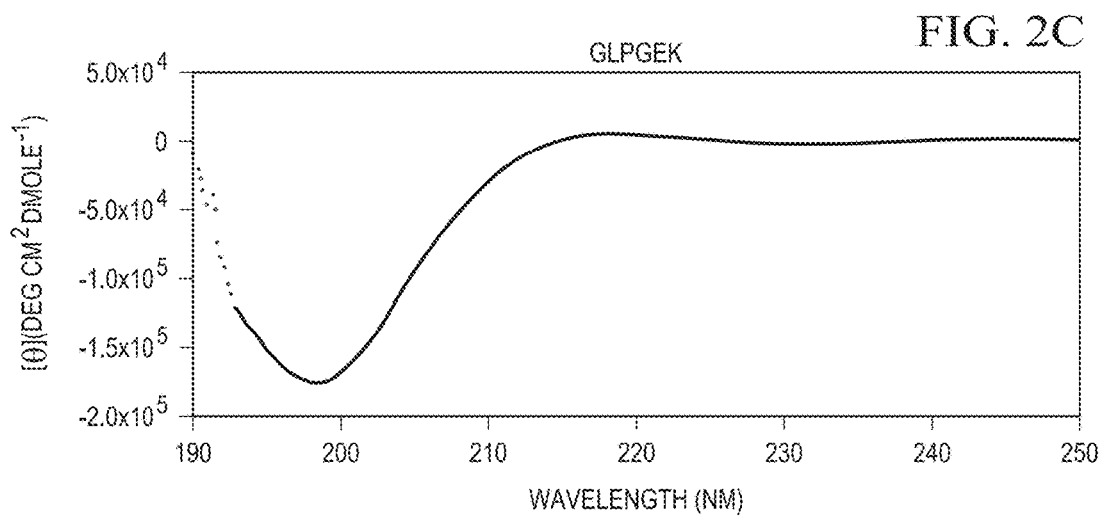
Figure 2D:
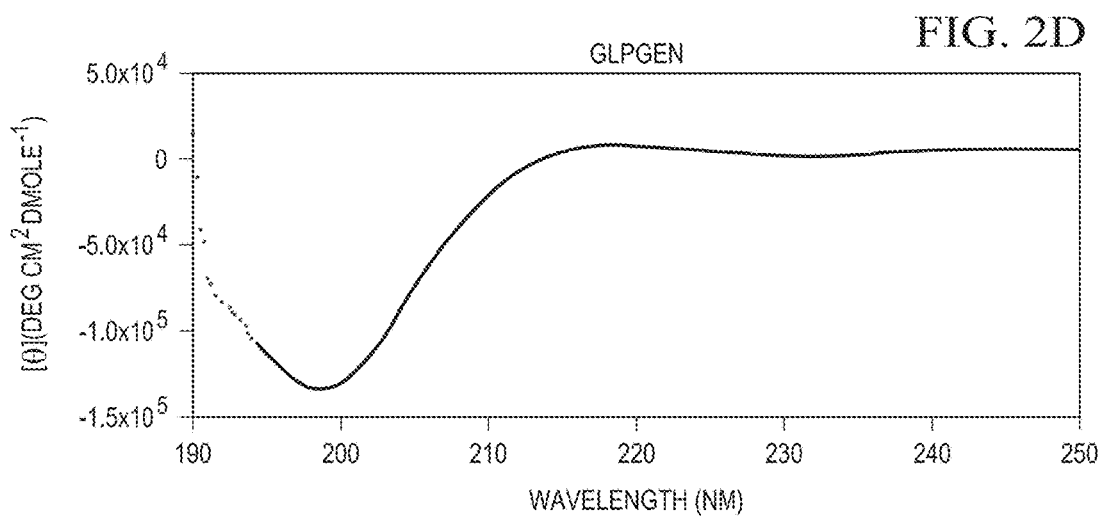
Figure 2E:
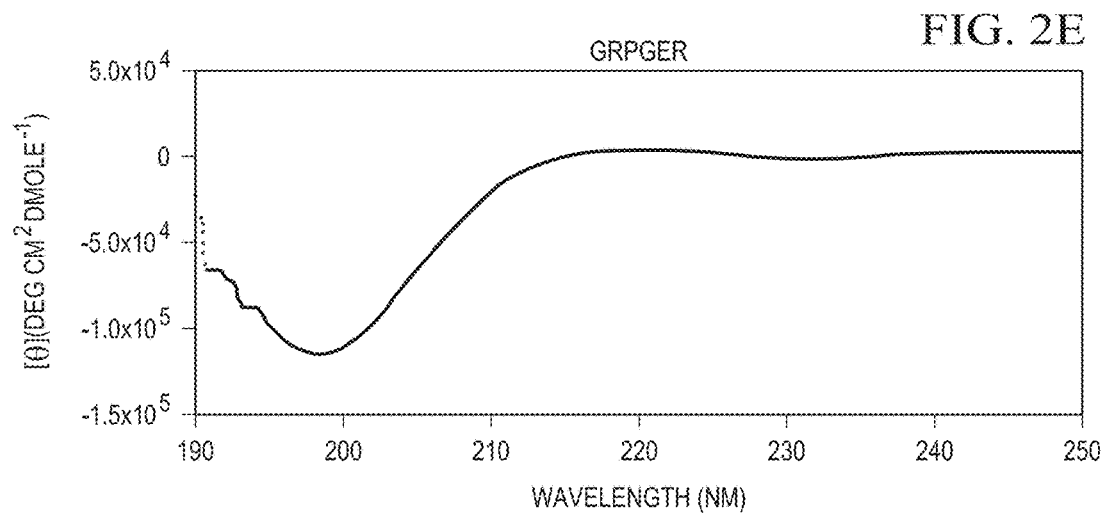
Figure 2F:
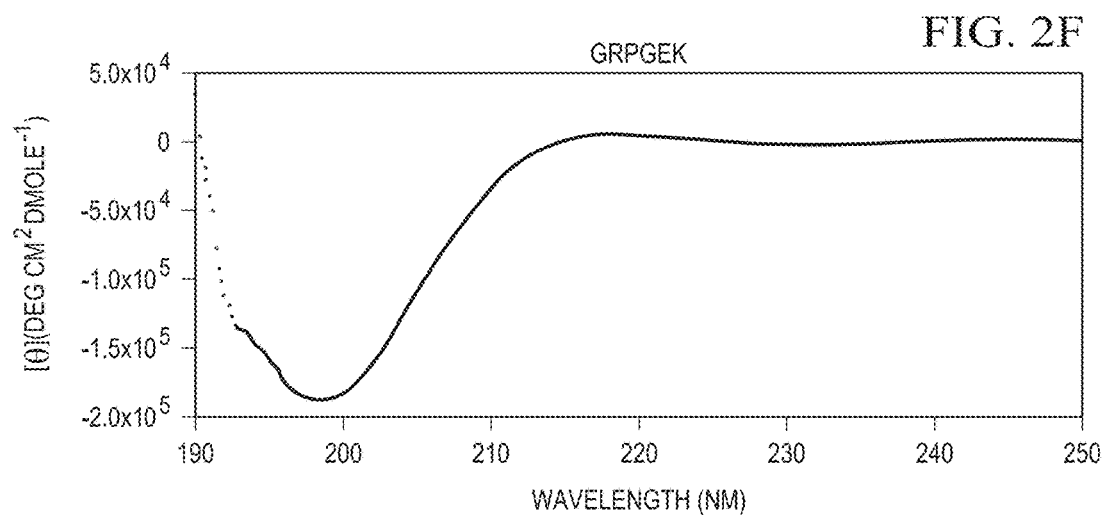
Figure 2G:
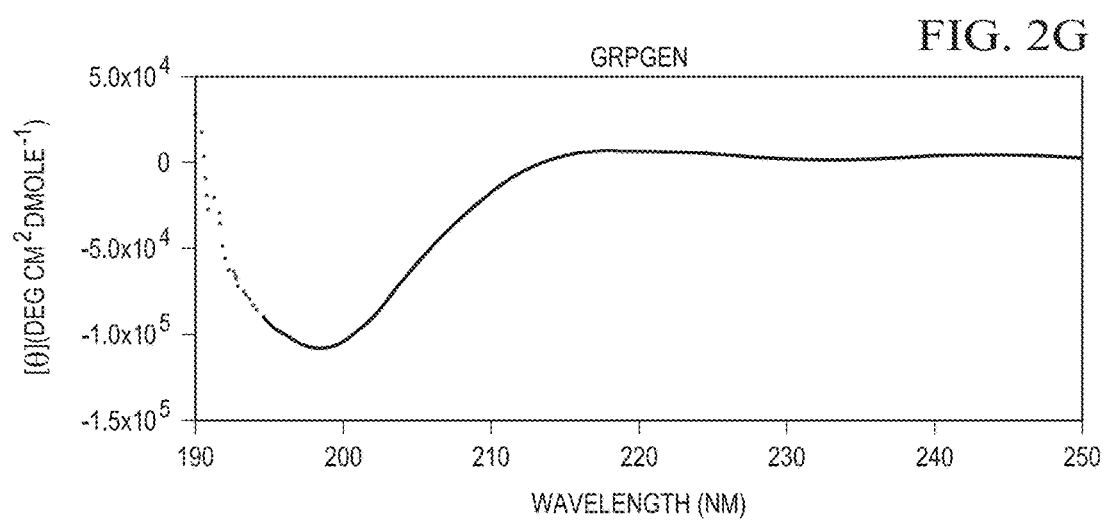
Figure 2H:
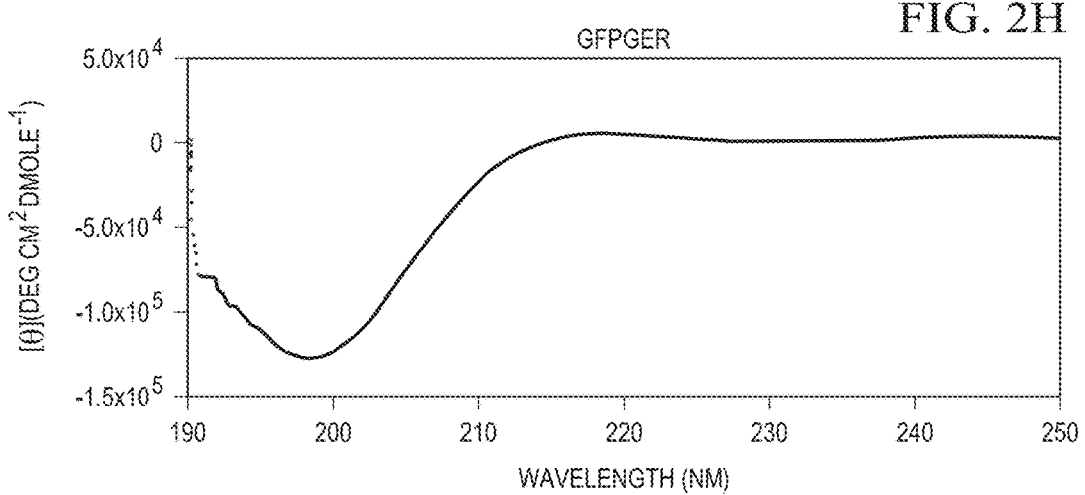
Figure 2I:
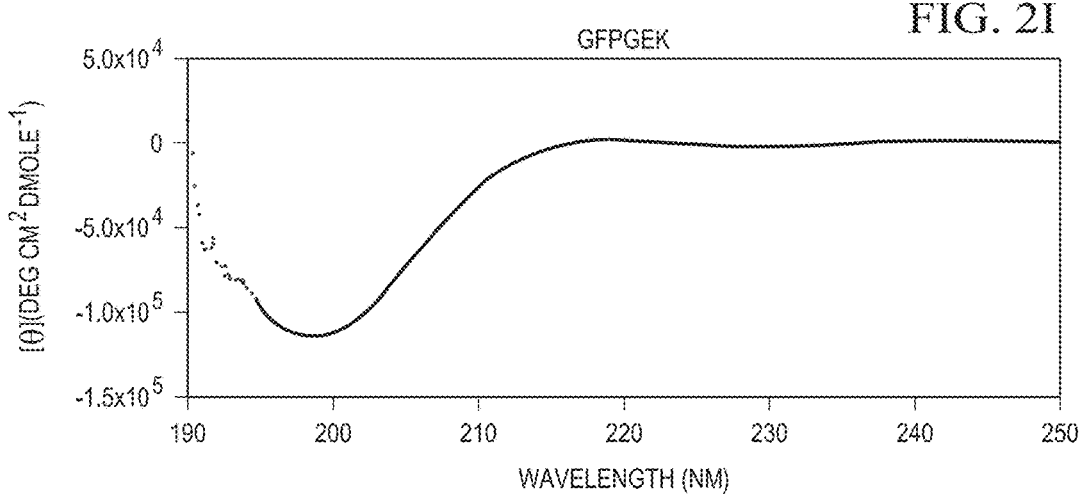
Figure 2J:
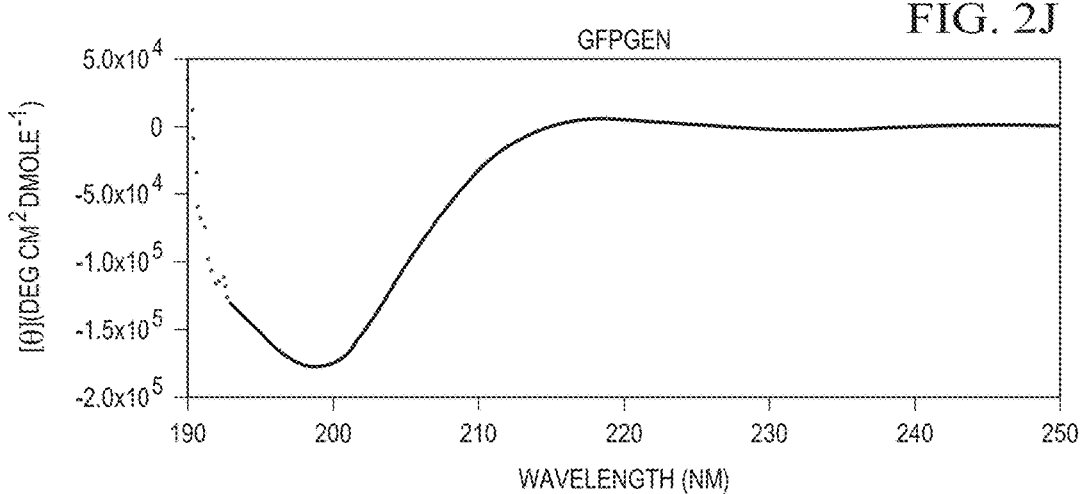
Figure 2K:
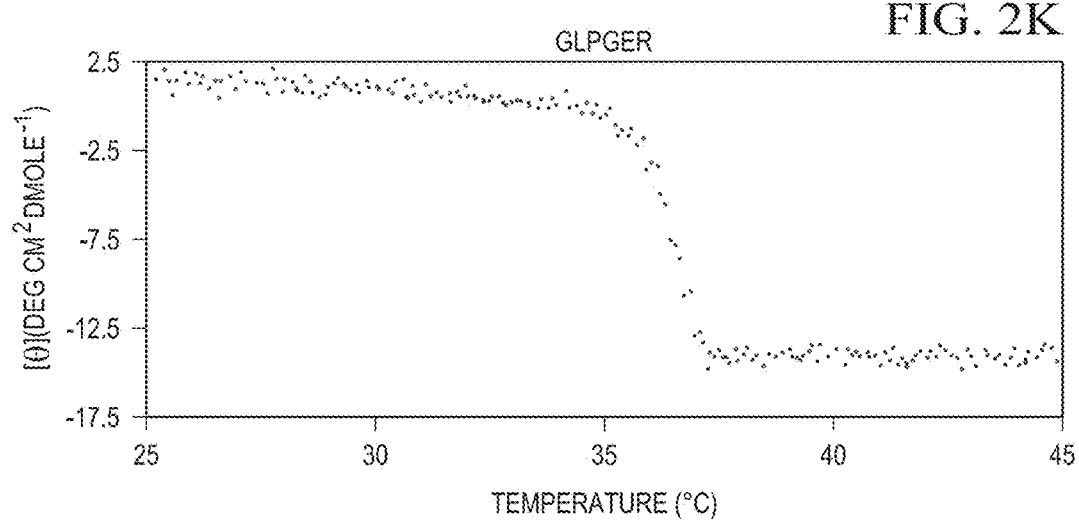
Figure 2L:
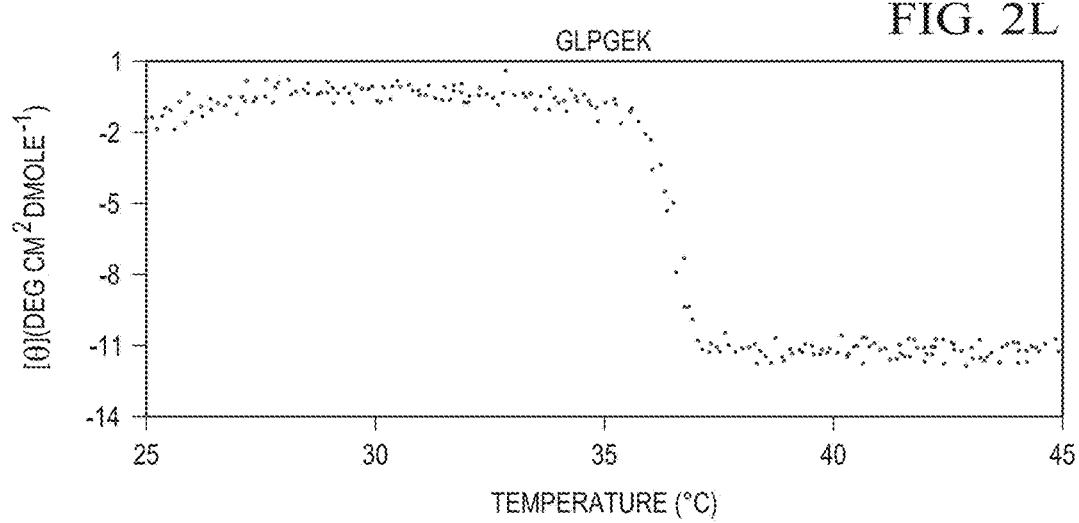
Figure 2M:
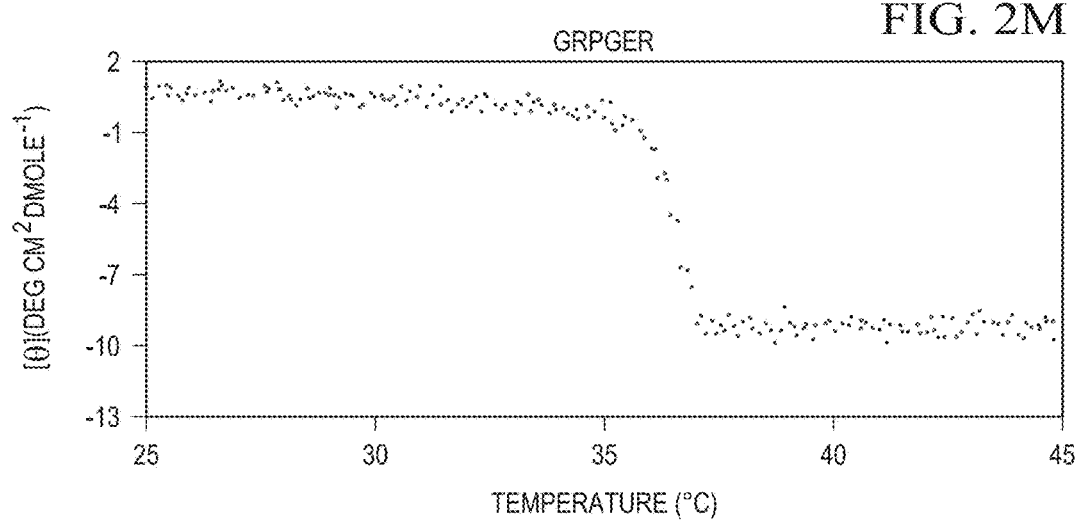
Figure 2N:
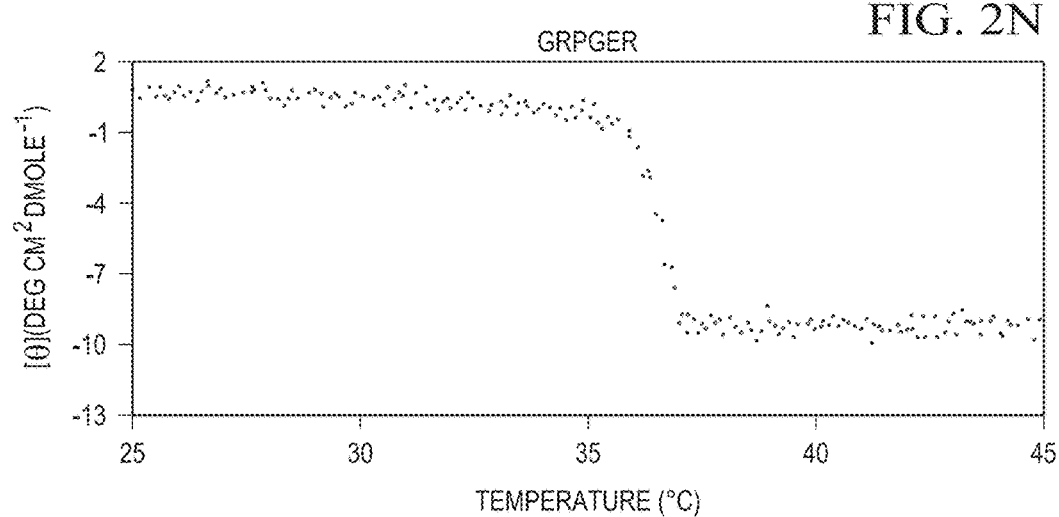
Figure 2O:
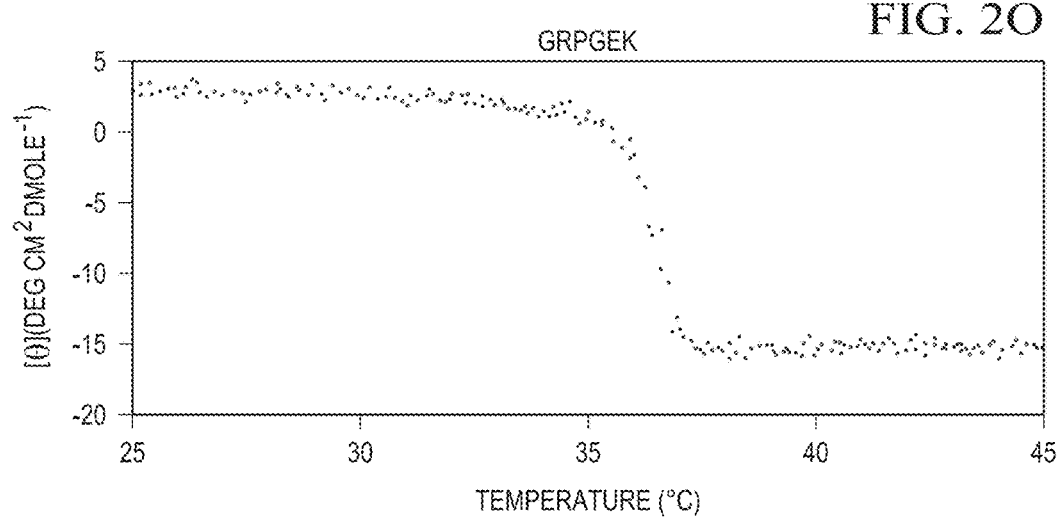
Figure 2P:
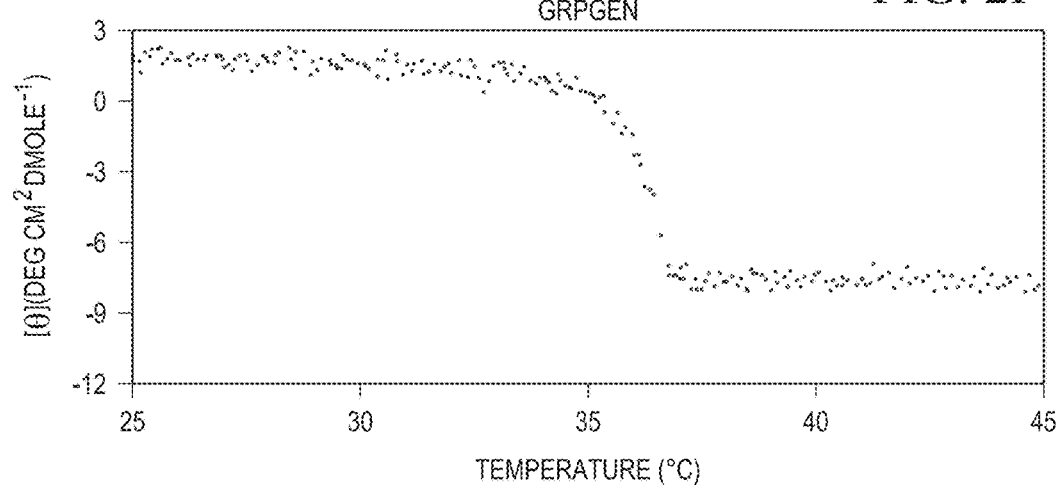
Figure 2Q:
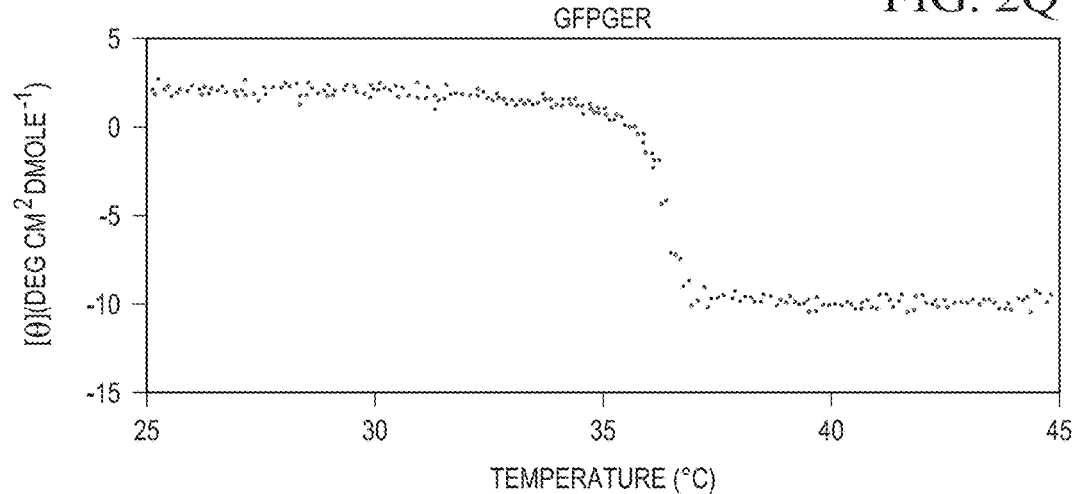
Figure 2R:
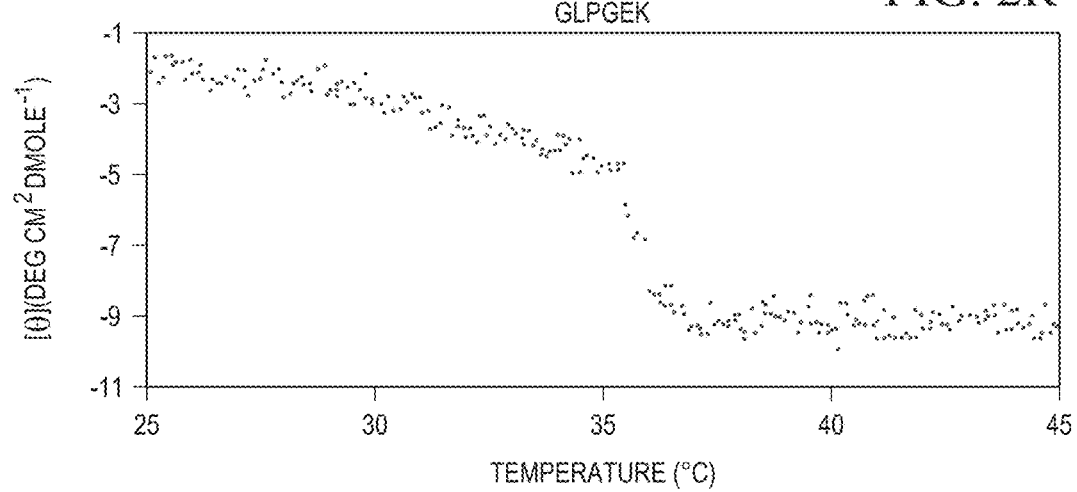
Figure 2S:
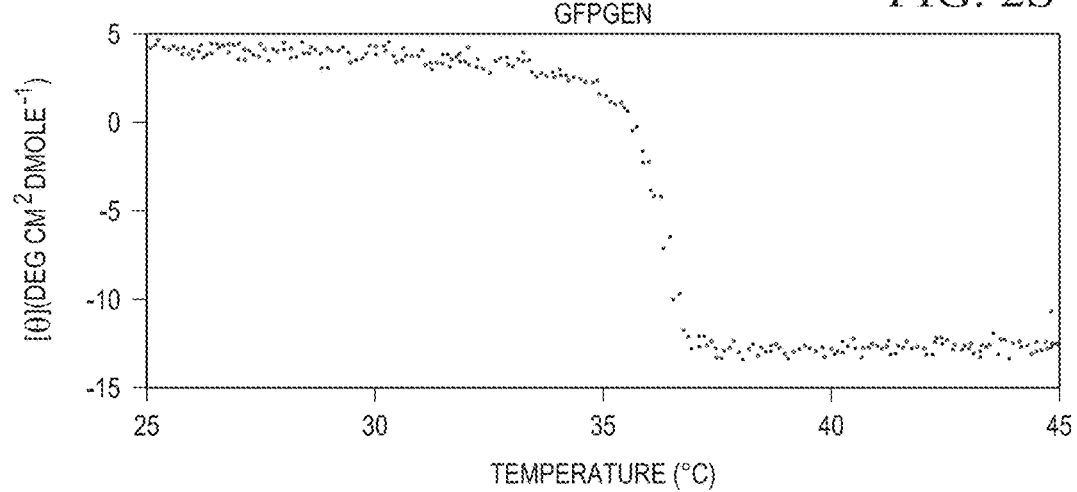
Figure 3A:
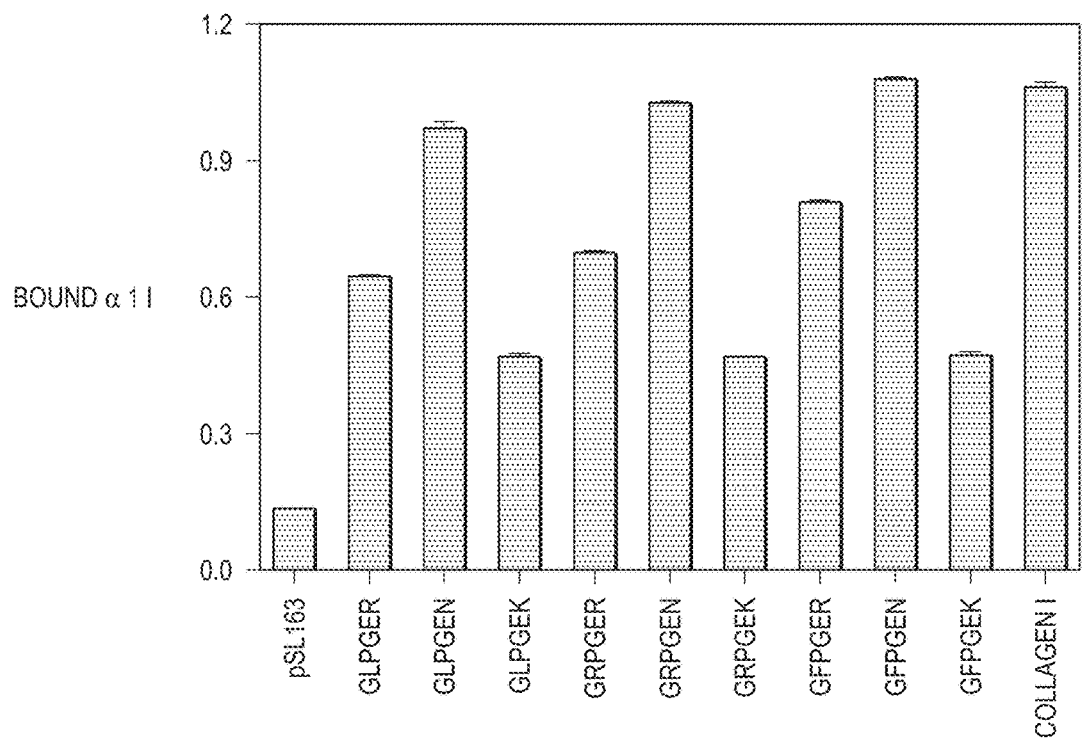
Figure 3B:
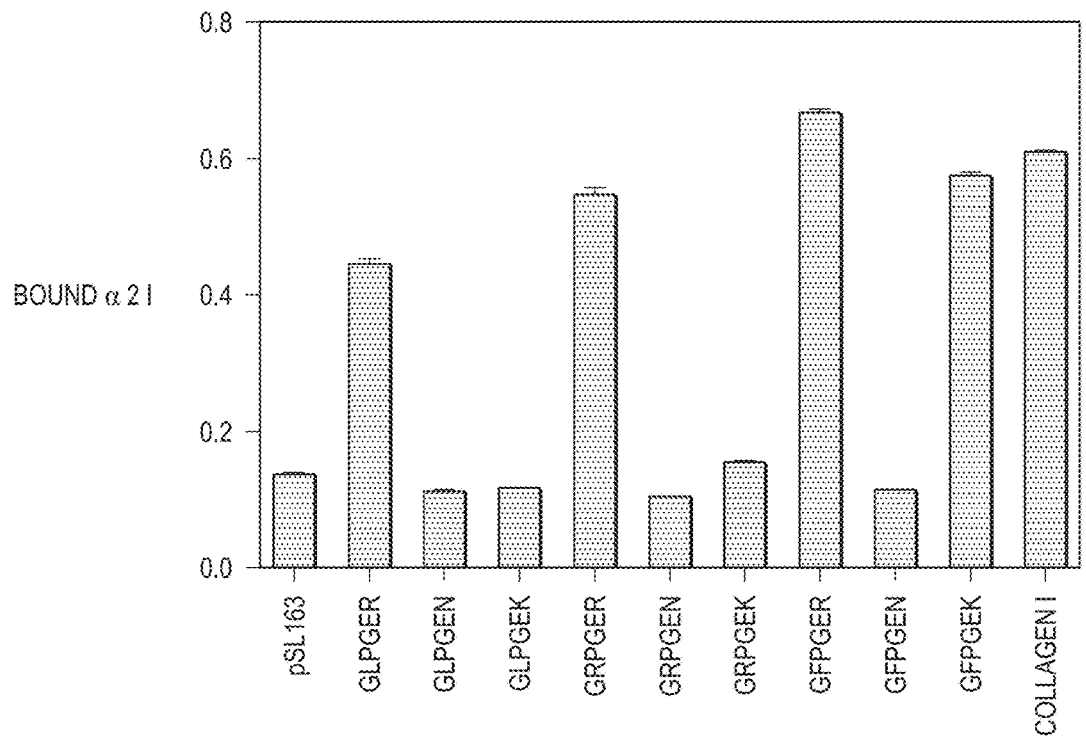

Recombinant Designer Collagens expressed in a bacterial system exhibit a triple helical structure at physiological temperatures. pSL163 (P163), a construct containing bacterial collagen-like sequences that form a triple helix, was used as a backbone. To generate receptor-binding motifs including, GLPGER (SEQ ID NO: 4), GLPGEN (SEQ ID NO: 5), GLPGEK (SEQ ID NO: 6), GRPGER (SEQ ID NO: 7), GRPGEN (SEQ ID NO: 8), GRPGEK (SEQ ID NO: 9), GFPGER (SEQ ID NO: 10), GFPGEN (SEQ ID NO: 11), GFPGEK (SEQ ID NO: 12), site-directed mutagenesis was used to 'insert' these cell-binding sites into the pSL163 backbone (FIG. 1). The constructs were expressed in E. coli and recombinant proteins were purified. As shown in FIG. 2A, purified collagen-like proteins have over 95% purity and form a triple helical structure under non-denatured conditions in 12% SDS-PAGE. Residue sequences correspond to the following numbered system (1-GLPGER (SEQ ID NO: 4), 2-GLPGEN (SEQ ID NO: 5), 3-GLPGEK (SEQ ID NO: 6), 4-GRPGER (SEQ ID NO: 7), 5-GRPGEN (SEQ ID NO: 8), 6-GRPGEK (SEQ ID NO: 9), 7-GFPGER (SEQ ID NO: 10), 8-GFPGEN (SEQ ID NO: 11), 9-GFPGEK (SEQ ID NO: 12)). Far UV Circular Dichroism spectral data recorded with wavelength scans of the Designer Collagens showed a typical triple helical structure (FIGS. 2B-2J). Circular Dichroism scans were recorded at 220 nm with a temperature slope of 10 degrees Celsius per hour. This data demonstrated that the Designer Collagens maintain a triple helical structure at a temperature close to normal human body temperature (FIGS. 2K-2S).

Example 6

Figure 4A:
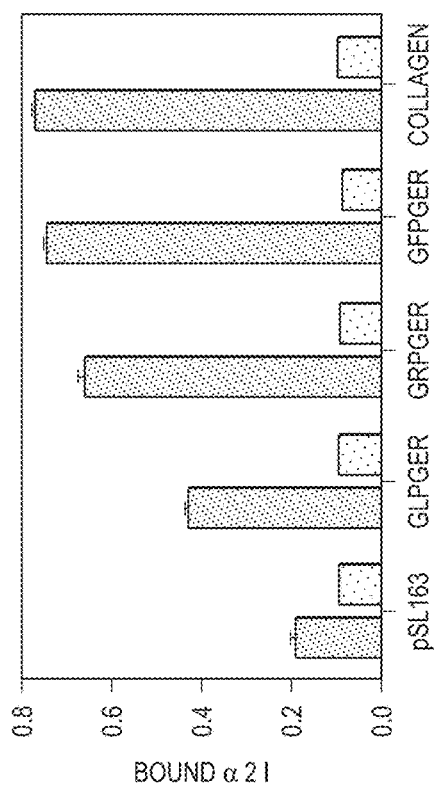
Figure 4B:
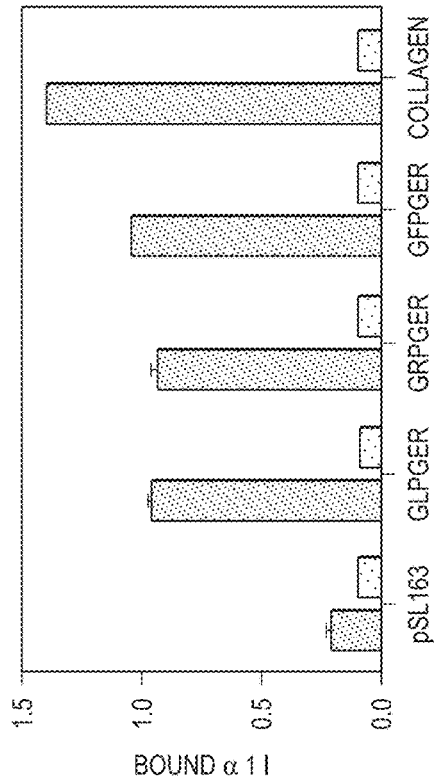
Figure 4C:
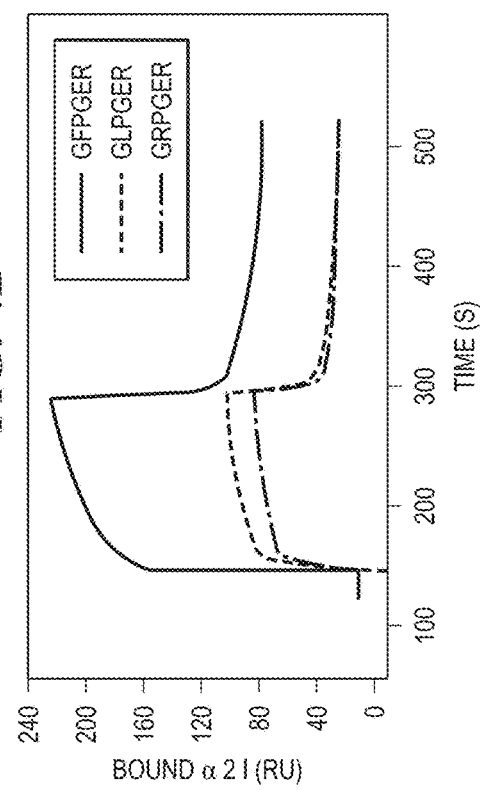
Figure 4D:
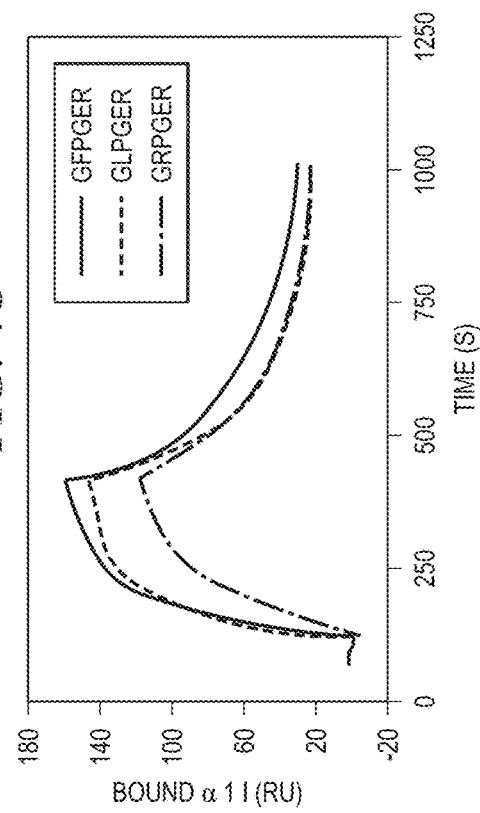

Integrins interact with Designer Collagens containing GLPGER (SEQ ID NO: 4), GLPGEN (SEQ ID NO: 5), GLPGEK (SEQ ID NO: 6), GRPGER (SEQ ID NO: 7), GRPGEN (SEQ ID NO: 8), GRPGEK (SEQ ID NO: 9), GFPGER (SEQ ID NO: 10), GFPGEN (SEQ ID NO: 11), and GFPGEK (SEQ ID NO: 12) cell-binding inserts. Binding of recombinant forms of integrins α1 and α2 I domains to immobilized Designer Collagens with GLPGER (SEQ ID NO: GLPGEN (SEQ ID NO: 5), GLPGEK (SEQ ID NO: 6), GRPGER (SEQ ID NO: 7), GRPGEN (SEQ ID NO: 8), GRPGEK (SEQ ID NO: 9), GFPGER (SEQ ID NO: 10), GFPGEN (SEQ ID NO: 11), and GFPGEK (SEQ ID NO: 12), motifs were determined by ELISA-based assays (FIGS. 3A-3B and FIGS. 4A-4B). Binding of recombinant forms of integrins α1 and α2 I domains to immobilized Designer Collagens with GRPGER (SEQ ID NO: 7), GLPGER (SEQ ID NO: 4), and GFPGER (SEQ ID NO: 10), was determined by Surface Plasmon Resonance analysis (FIGS. 5C and 5D-5F). The Designer Collagens with GLPGER (SEQ ID NO: 4), GRPGER (SEQ ID NO: 7), and GFPGER (SEQ ID NO: 10) support the binding of α1 and α2 I domains (FIGS. 4A-4B, grey bars) via a metal ion dependent manner since binding is completely abolished by EDTA (FIGS. 4A-4B, white bars). C2C12 cells stably expressing either integrin α1 or α2 subunit (C2C12-α1 or C2C12-α2) were used to determine whether the Designer Collagens with GLPGER (SEQ ID NO: 4), GRPGER (SEQ ID NO: 7), and GFPGER (SEQ ID NO: 10) motifs support adhesion of these cell lines.

Figure 5A:
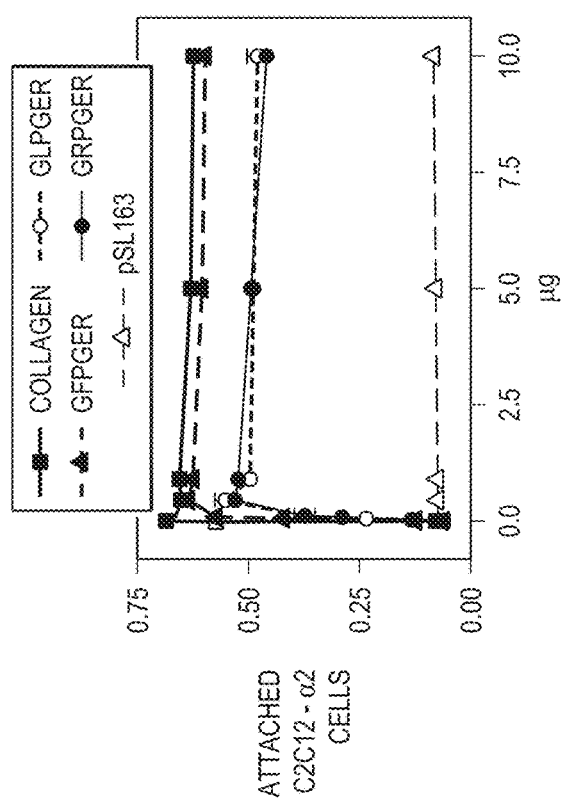
Figure 5B:
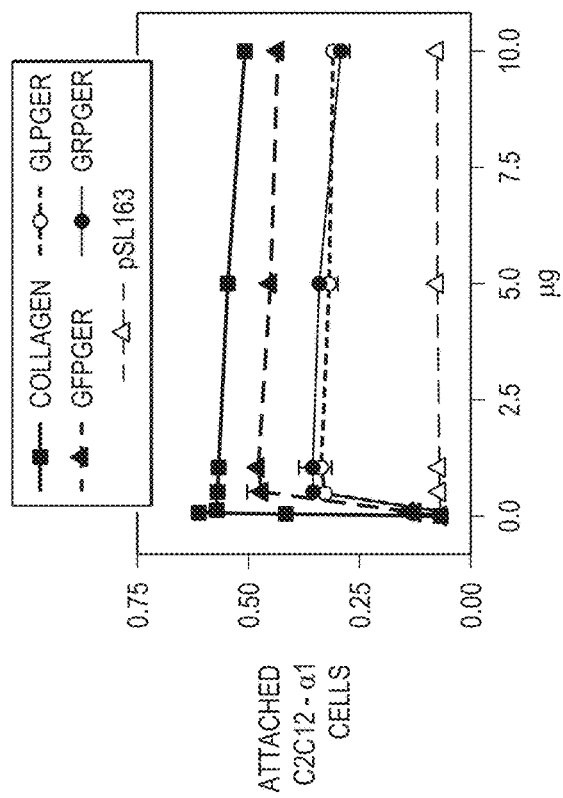
Figure 5C:
Figure 5E:
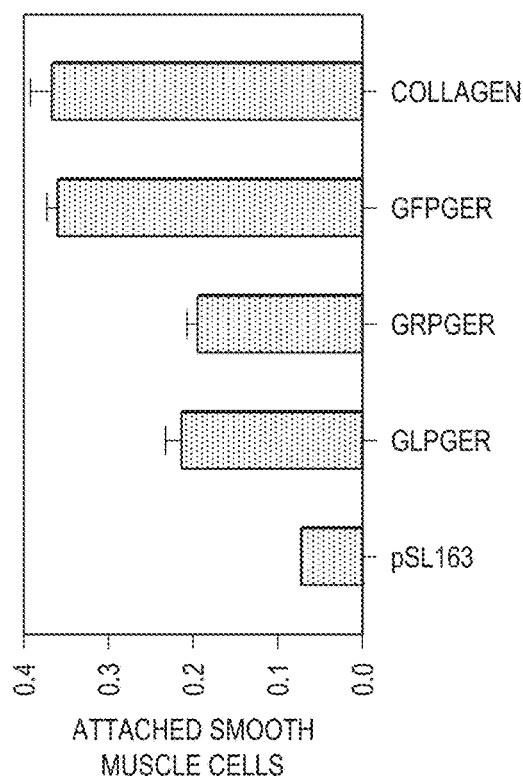
Figure 5G:
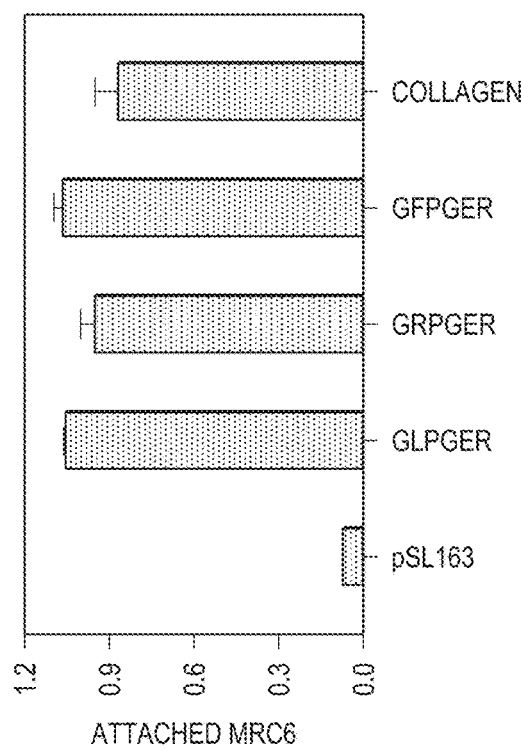
Figure 5D:
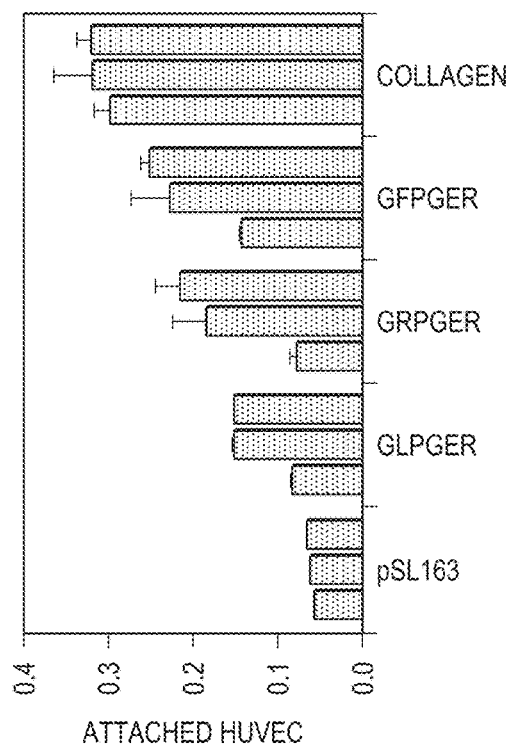
Figure 5F:
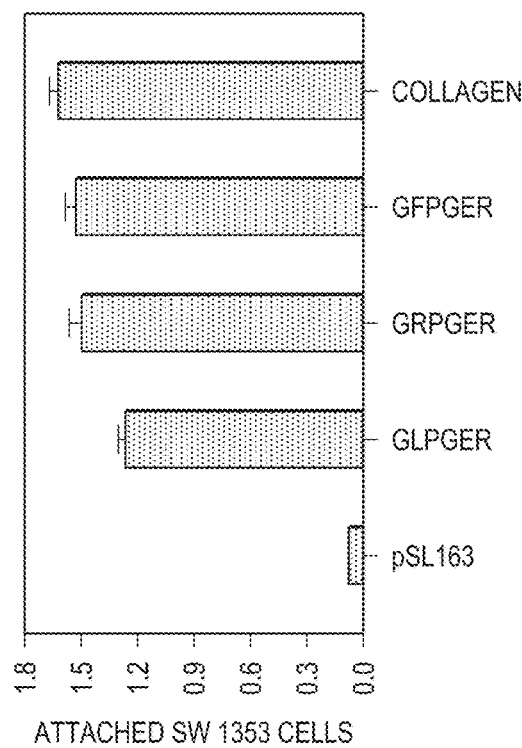

As shown in FIG. 5A, the Designer Collagens allowed adherence of C2C12-α1 cells or C2C12-α2 cells at a similar level of adherence to collagen type I, a positive control. Because pSL163 is a Designer Collagen without an 'inserted' motif, it is used as a negative control and did not mediate adherence of either cell type. This is an invaluable control because it implicates specific sequences are responsible for the interactions and not solely the presence of a triple helical protein. C2C12 parental cells did not adhere on any substrates; indicating the adhesion of C2C12-α1 and C2C12-α2 cells to the Designer Collagens is mediated by integrin α1β1 and α2β1. Cell adherence to substrates via specific integrins will exhibit outside-in signaling to induce intracellular signaling pathways, which will manifest as a morphology change resulting in spreading of cells. Adhered C2C12-α1 and C2C12-α2 cells on the Designer Collagens exhibited spreading within 60 minutes incubation at 37° C. in the presence of 5% CO2 (FIG. 5B). This indicates that integrin binding motifs, GLPGER (SEQ ID NO: 4), GRPGER (SEQ ID NO: 47), and GFPGER (SEQ ID NO: 10) actively bind to cells and induce intracellular signaling pathways. In addition, the Designer Collagens allow attachment and spreading of different cell types including endothelial cells in a dose-dependant manner (FIG. 5C), fibroblasts (MRC5), smooth muscle cells, and chondrocytic cells (SW1353) (FIGS. 5D-5F). FIG. 5D shows that the Designer Collagens allow attachment and spreading of endothelial cells in a dose-dependant manner. FIGS. 5E-5G show that the Designer Collagens allow attachment and spreading of fibroblasts (MRC5), smooth muscle cells, and chondrocytic cells (SW1353) in a dose-dependant manner.

Example 7

Designer Collagens with GLPGER (SEQ ID NO: 4), GRPGER (SEQ ID NO: 7), and GFPGER (SEQ ID NO: 10) motifs are non-thrombogenic. The Designer Collagens support adherence of different cell types, some through an interaction with α2β1. Thus, whether Designer Collagens activated platelets by binding to integrin α2β1 was examined. FIG. 6 shows that Designer Collagens did not induce platelet aggregations at a 10-fold higher concentration than collagen type I, which aggregates platelets to over 90% in 10 minutes.

Example 8

Figure 7C:
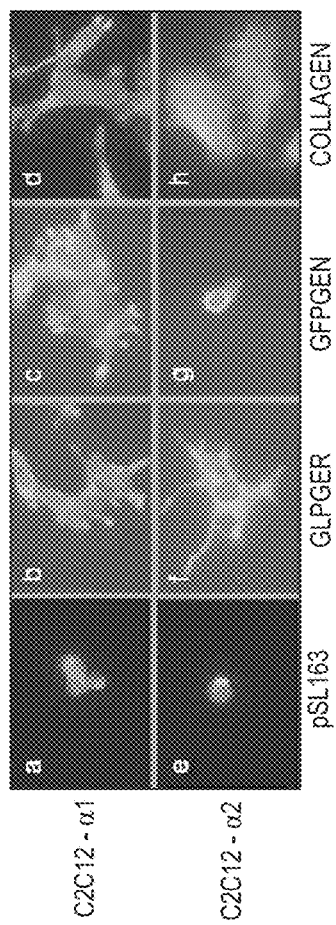
Figure 7D:
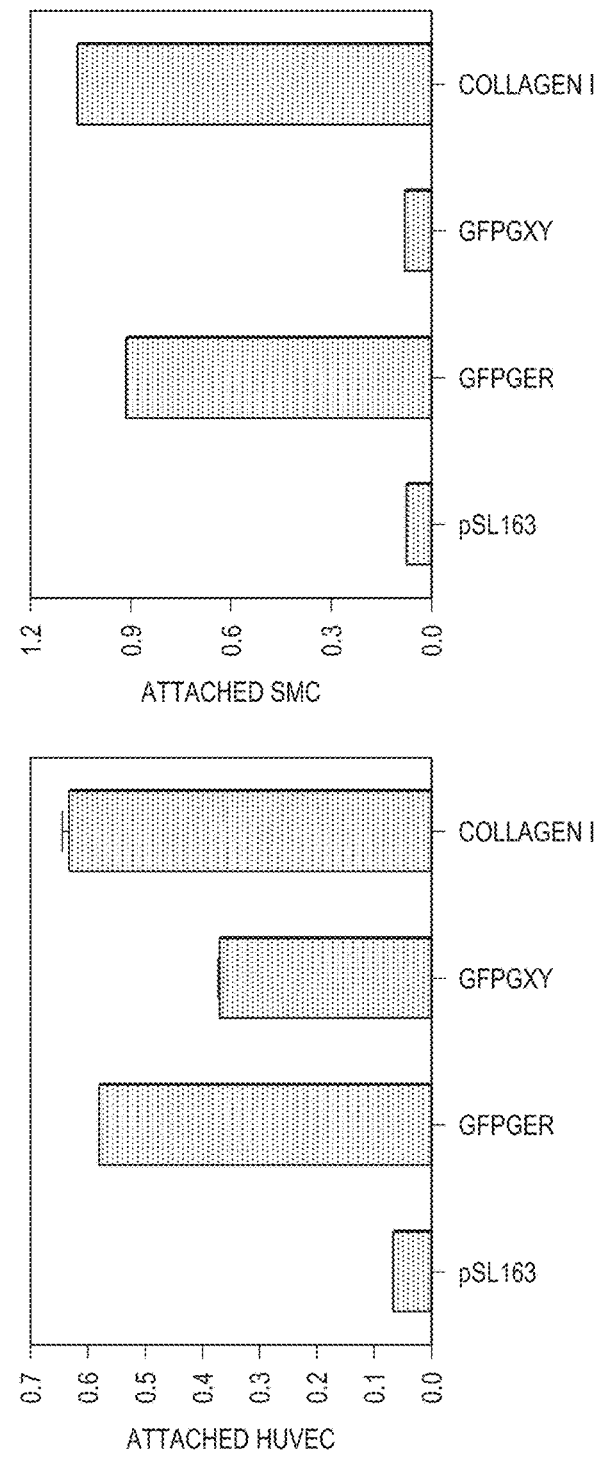

Designer Collagen with an inserted motif of GFPGEN (SEQ ID NO: 11) selectively binds to integrin α1β1, but not to α2β1. The Designer Collagen with a GFPGEN (SEQ ID NO: 11) motif was expressed in E. coli and purified. It was tested for binding to integrin α1 and α2 I domains by ELISA based assays and Surface Plasmon Resonance analysis. The integrin α1 I domain binds to immobilized GFPGEN (SEQ ID NO: 11) containing Designer Collagen, while the integrin α2 I domain fails to bind to Designer Collagen containing GFPGEN (SEQ ID NO: 11) motifs (FIG. 7A). Integrin α1 and α2 I domains bind to immobilized GFPGER (SEQ ID NO: 10) containing Designer Collagen and collagen type I as shown previously. In cell adherence assays, C2C12-α1 cells only adhere on GFPGEN (SEQ ID NO: 11) containing Designer Collagen, but C2C12-α2 cells and C2C12 parental cells do not (FIG. 7B), this indicates that GFPGEN (SEQ ID NO: 11) selectively interacts with integrin α1β1. The interaction of integrin α1β1 with GFPGEN induces intracellular signaling as shown by spreading of C2C12-α1 cells on a GFPGEN (SEQ ID NO: 11) containing Designer Collagen (FIG. 7C). GFPGEN (SEQ ID NO: 11) containing Designer Collagen also supported adhesion and spreading of human endothelial cells (FIG. 7D, where GFPGXY is GFPGEN (SEQ ID NO: 11), HUVEC graph). GFPGEN (SEQ ID NO: 11) containing Designer Collagen did not support the adherence of smooth muscle cells (SMC) (FIG. 7D, where GFPGXY is GFPGEN (SEQ ID NO: 11), SMC graph). Integrin α2β1 is expressed on endothelial cells as well as smooth muscle cells.

Intracellular pathways activated upon cell adherence to Designer Collagens with inserted motifs of GFPGER (SEQ ID NO: 10) and GFPGEN (SEQ ID NO: 11) were determined herein. Activation of focal adhesion kinase (FAK) was detected in human dermal microvascular endothelial cells lysate 30 minutes after adherence to Designer Collagens and Collagen type1, but not P163 as demonstrated by Western blot analysis (FIGS. 8A-8F). Binding and oligomerization of both α1 and α2 in complex with α1 leads to autophosphorylation of Y397. Therefore, the results demonstrated by activation of FAK pY397 by Collagen type 1 and Designer Collagens show Designer Collagen not only bind to integrins, but mediate intracellular signaling. Collagen type 1 will preferentially bind α2 when both ligands are available. α2 signaling does not activate Shc, however it activates p38. Results herein indicate a strong activation of Shc by GFPGEN (SEQ ID NO: 11) containing Designer Collagen, an activation of Shc by GFPGER (SEQ ID NO: 10) containing Designer Collagen, and minimal to no activation of Shc by Collagen type 1. The results also indicate a strong activation of p38 by Collagen type 1, activation of p38 by GFPGER (SEQ ID NO: 10) containing Designer Collagen, and minimal to no activation by GFPGEN (SEQ ID NO: 11) containing Designer Collagen.

The data shown indicates reproducible and predictable activation signals by Collagen type 1. However, GFPGER (SEQ ID NO: 10) containing Designer Collagen despite the capability of binding both α1 and α2 does not activate Shc or p38 in the same manner as Collagen type 1. These data suggest a more equal preference of GFPGER (SEQ ID NO: 10) containing Designer Collagen to bind α1 and α2 when compared to Collagen type 1. These intracellular signaling properties add to the usefulness of Designer Collagens mediating specific cell functions such as angiogenesis, wound healing, adhesion prevention, cell recruitment, cell proliferation, and cell death.

Example 9

Designer collagen with a GFPGEN (SEQ ID NO: 11) motif is non-thrombogenic. The Designer Collagen with a GFPGEN (SEQ ID NO: 11) motif is non-thrombogenic as shown in platelet aggregation assays (FIG. 6). Since GFPGEN (SEQ ID NO: 11) only binds to integrin α1β1, while GFPGER (SEQ ID NO: 10) binds to both integrin α1β1 and α2β1, whether GFPGER (SEQ ID NO: 10) and GFPGEN (SEQ ID NO: 11) could inhibit collagen-induced platelet aggregations was examined. GFPGER (SEQ ID NO: 10) shows inhibitory effects on collagen type I induced platelet aggregation. This indicates that the Designer Collagen binds to integrin α2β1 on platelets without activation and competitively blocks the binding of native collagen type I (FIG. 9). GFPGEN (SEQ ID NO: 11) containing Designer Collagen did not inhibit collagen induced platelet aggregation, indicating that GFPGEN (SEQ ID NO: 11) does not compete with native collagen type I for the binding to integrin α2β1 on platelets. It is known that integrin α1β1 is not expressed on platelets.

Example 10

Figure 10A:
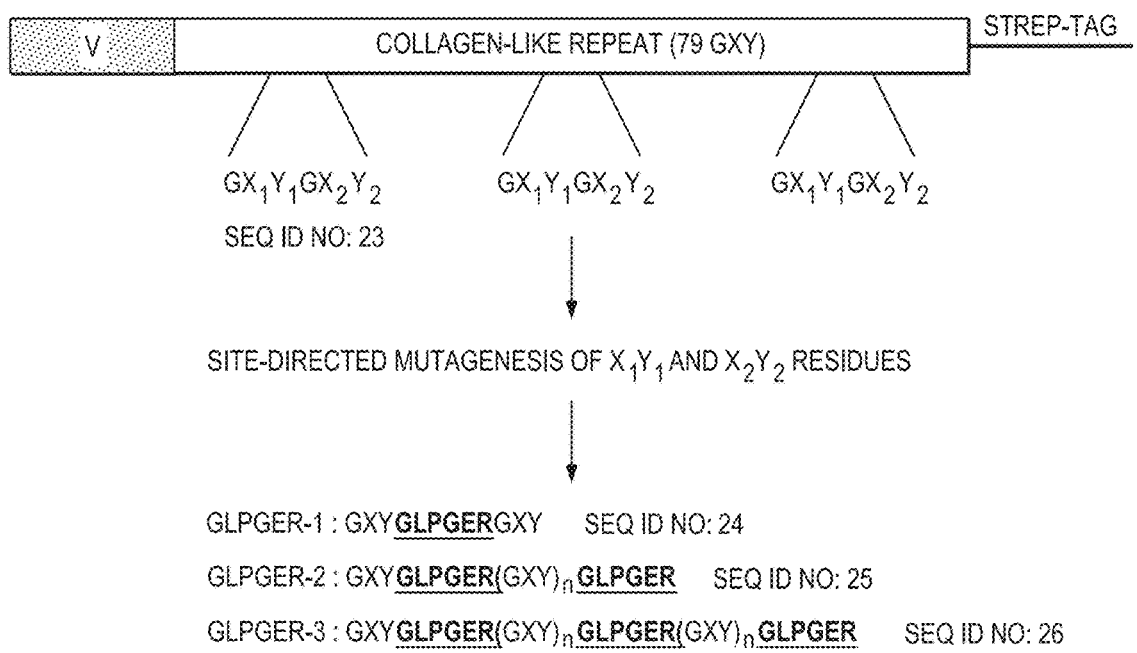
FIG. 10E shows that increased density and numbers of integrin specific motifs on Designer Collagens resulted in a dramatic increasing of cell migration that reached the highest level in comparison to Collagen type I.
FIG. 10F shows GLPGER (SEQ ID NO:4) (4) and GLPGER (SEQ ID NO:4) (5), where GLPGER (SEQ ID NO:4) (4) and GLPGER (SEQ ID NO:4) (5) contain 4 and 5 repeats of the integrin binding sequence, GLPGER (SEQ ID NO:4), respectively, bind α1 I domain with increased affinity in comparison to a single GLPGER (SEQ ID NO:4) repeat.
Figure 10B:
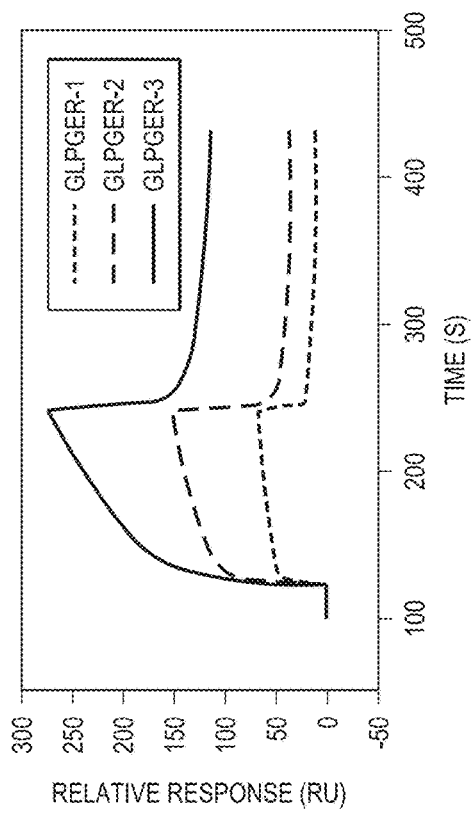

Cell adhesion and migration is modulated by density and affinity of integrin specific motifs on the Designer Collagen substrates. Whether modulation of density and affinity of integrin specific motifs on the Designer Collagen would influence cell behavior including attachment and migration on the substrates was determined. To this end, P163 was used to present spatial multiple integrin binding repeats that contain one, two, three, four or five repeats of GLPGER (SEQ ID NO: 4) sequences. GXY repeat sequences are located between the GLPGER (SEQ ID NO: 4) repeats to provide space between the integrin specific motifs (GLPGER-1 (SEQ ID NO: 4), GLPGER-2 (SEQ ID NO: 4), and GLPGER-3 (SEQ ID NO: 4)) (FIG. 10A). The Designer Collagens form oligomers on a polyacrylamide gel under non-reducing condition and also exhibited a typical triple helix structure with melting temperature values of 36.5° C. in thermal transition analyzed by CD spectroscopy. Surface Plasmon Resonance analysis was performed by passing over I domains to immobilized GLPGER-1 (SEQ ID NO: 4), GLPGER-2 (SEQ ID NO: 4), and GLPGER-3 (SEQ ID NO: 4). The results indicated that α1 I and α2 I domains bound to the Designer Collagens in the presence of 1 mM MgCl2 (FIG. 10B, where Y axis is α1 I domain and 11c, where Y axis is α2 I domain) and the binding was abolished in the presence of 1 mM EDTA. Normalized representative binding profiles of the I domains to captured GLPGER-1 (SEQ ID NO: 4), GLPGER-2 (SEQ ID NO: 4), and GLPGER-3 (SEQ ID NO: 4) resulted in an increased in the binding affinity of the I domains to Designer Collagens with increased number of GLPGER (SEQ ID NO: 4) repeats. The dissociation constant (KD) of integrin α1 I domain to captured GLGPER (SEQ ID NO: 4) repeats was 1.33±0.15 µM, while that of integrin α2 I domain was 39.7, 25.9, and 11.8 µM to captured GLPGER-1 (SEQ ID NO: 4), GLPGER-2 (SEQ ID NO: 4), and GLPGER-3 (SEQ ID NO: 4, respectively.

Figure 10C:
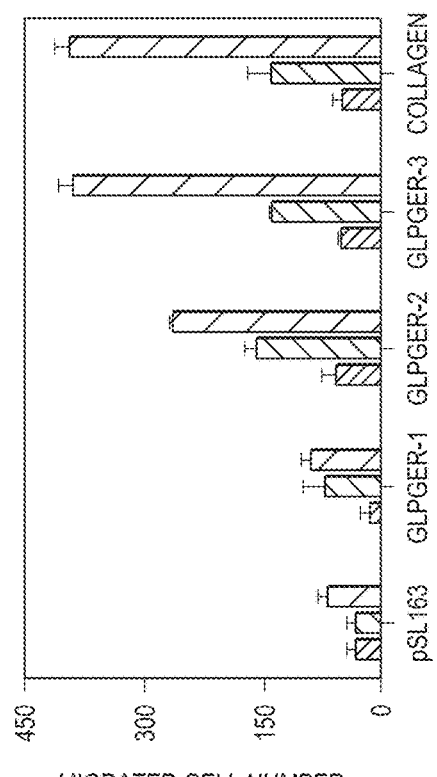
Figure 10D:
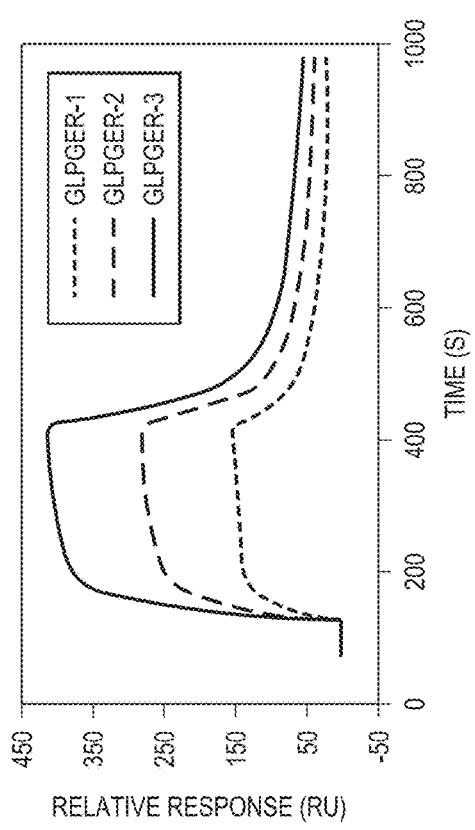

To assess the specificity of cell-substrate interactions, cell adhesion to the Designer Collagens was investigated by seeding human endothelial cells in serum-free medium containing 1 mM MgCl2 and 1 mM CaCl2 to 96 wells coated with increased concentration of GLPGER-1 (SEQ ID NO: 4), GLPGER-2 (SEQ ID NO: 4), GLPGER-3 (SEQ ID NO: 4), Collagen type I, and P163. All GLPGER (SEQ ID NO: 4) repeats served as a substrate for the attachment of the endothelial cells, as did type I Collagen (FIG. 10C). The attachment of cells depends on surface density of GLPGER (SEQ ID NO: 4) contributed from amounts of coated substrates as well as numbers of integrin specific motifs, which give rise to increased attachment of the endothelial cells on the substrates. FIG. 10D shows cell adhesion to the Designer Collagens investigated by seeding human endothelial cells in serum-free medium containing 1 mM MgCl2 and 1 mM CaCl2 to 96 wells coated with increased concentration of GLPGER-1 (SEQ ID NO: GLPGER-2 (SEQ ID NO: 4), GLPGER-3 (SEQ ID NO: 4), Collagen type I, and P163. All GLPGER (SEQ ID NO: 5) repeats served as a substrate for the attachment of the endothelial cells, as did type I Collagen.

Figure 10E:
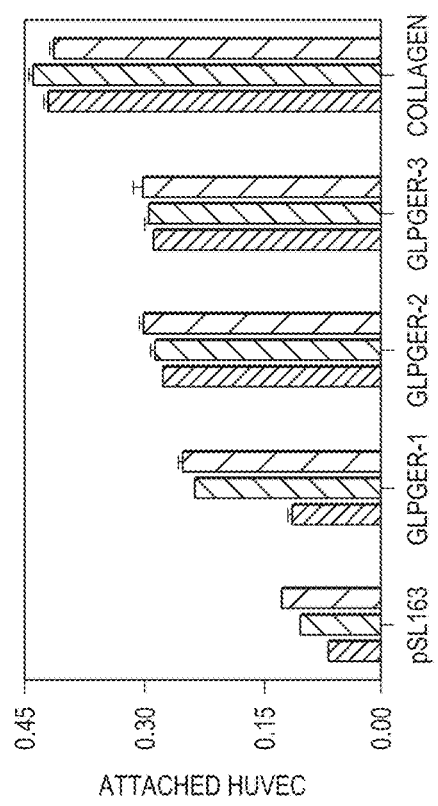
Figure 10F:
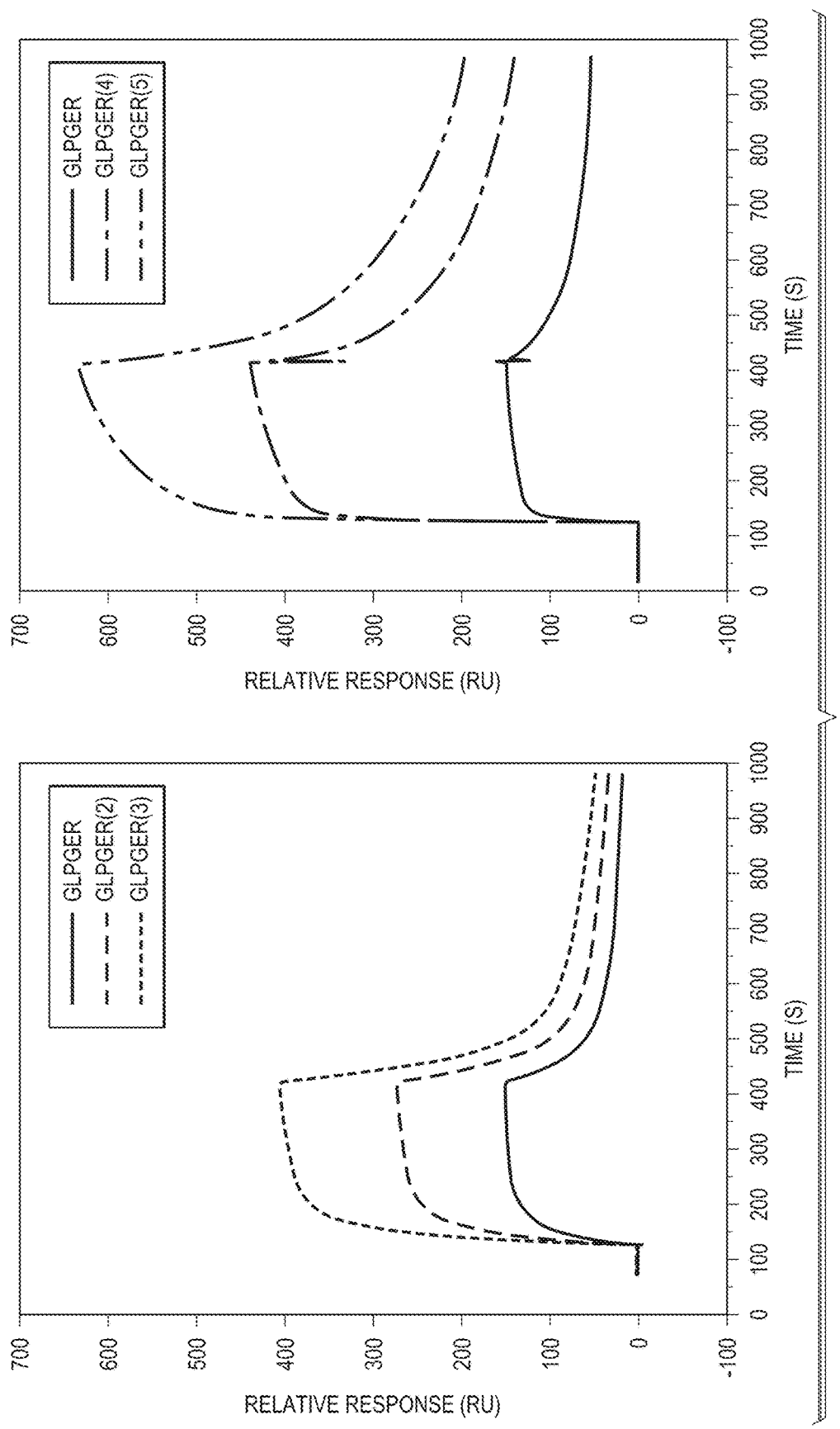

The effect of ligand density and affinity on endothelial cell migration was determined by counting migrated cells after a 4 hour time period in the presence and absence of soluble Designer Collagens GLPGER-1 (SEQ ID NO: 4), GLPGER-2 (SEQ ID NO: 4), GLPGER-3 (SEQ ID NO: 4), and type I Collagen and P163. These results showed that the integrin specific motifs on Designer Collagens are able to support cell migration in the absence of other cell-substrate adhesive interactions. Increased density and numbers of integrin specific motifs on Designer Collagens resulted in a dramatic increasing of cell migration that reached the highest level in comparison to Collagen type I (FIG. 10E). The endothelial cell migration is enhanced in a dose-dependent manner and controlled by modulating ligand surface density and binding affinity. FIG. 10F shows that Designer Collagens containing 4 and 5 repeats of the integrin binding sequence, GLPGER (SEQ ID NO: 4), respectively, bind $\alpha 1$ I domain with increased affinity in comparison to a single GLPGER (SEQ ID NO: 4) repeat.

Designer Collagen is prepared as a pathogen-free biomaterial using a prokaryotic expression system. Prokaryotic expression systems can be scaled up with current manufacturing process pipelines and offer lot-to-lot consistency with cost-effectiveness. Designer Collagens have the capacity to form a triple helix without the presence of hydroxyproline, which adds a cost advantage. Designer Collagens have multiple and different inserted sequences, which requires separate production. The mixing of Designer Collagens for product optimization is possible post-purification. A possible limitation of prokaryotic expression is the lack of post-translation modification. Certain applications of Designer Collagens do not require post-translational modification, but if the need arises, alternative expression systems could be used. Current methods of collagen purification rely on purification methods from an animal source. These methods are inconsistent, expensive, and offer only native collagen.

Designer Collagens that do not contain any 'inserted' residue such as, pSL163, showed minimal binding to integrin I domains did not support the adherence of different cell types. Thus, these Designer Collagens could be used as anti-adhesion biomaterials. Anti-adhesion materials currently use cellulose or other coatings of a mesh to prevent the formation of adhesion after trauma or surgery. Designer Collagens containing could be useful in cell recruitment or maintenance of a certain cell type in a localized area. The adherence to and subsequent intracellular signaling of $\alpha 1\beta 1$ and $\alpha 2\beta 1$ by GFPGER (SEQ ID NO: 10) containing Designer Collagens could be useful in stimulating multi-step processes such as angiogenesis. Designer Collagens containing GFPGEN (SEQ ID NO: 11) could be optimal vascular graft coatings or stent coatings. This unique biomaterial supports the adherence and spreading of endothelial cells but not smooth muscle cells and does not mediate platelet aggregation. Alternative formulations may include chimeric Designer Collagens encompassing different protein domains to achieve a desired function, chemical crosslinking effects needed to instill a certain property with regard to stability, a chemical effect needed to facilitate attachment of Designer Collagens to a certain material, and undetermined 'inserts' which impart a new property and function of Designer Collagens for new markets. These undetermined 'inserts' could range in function, however, other representative targets include bone sialoprotein binding sequences, integrins $\alpha 10\beta 1$ and $\alpha 11\beta 1$ binding sequences, and many extracellular matrix constituents.

Example 11

Figure 11:
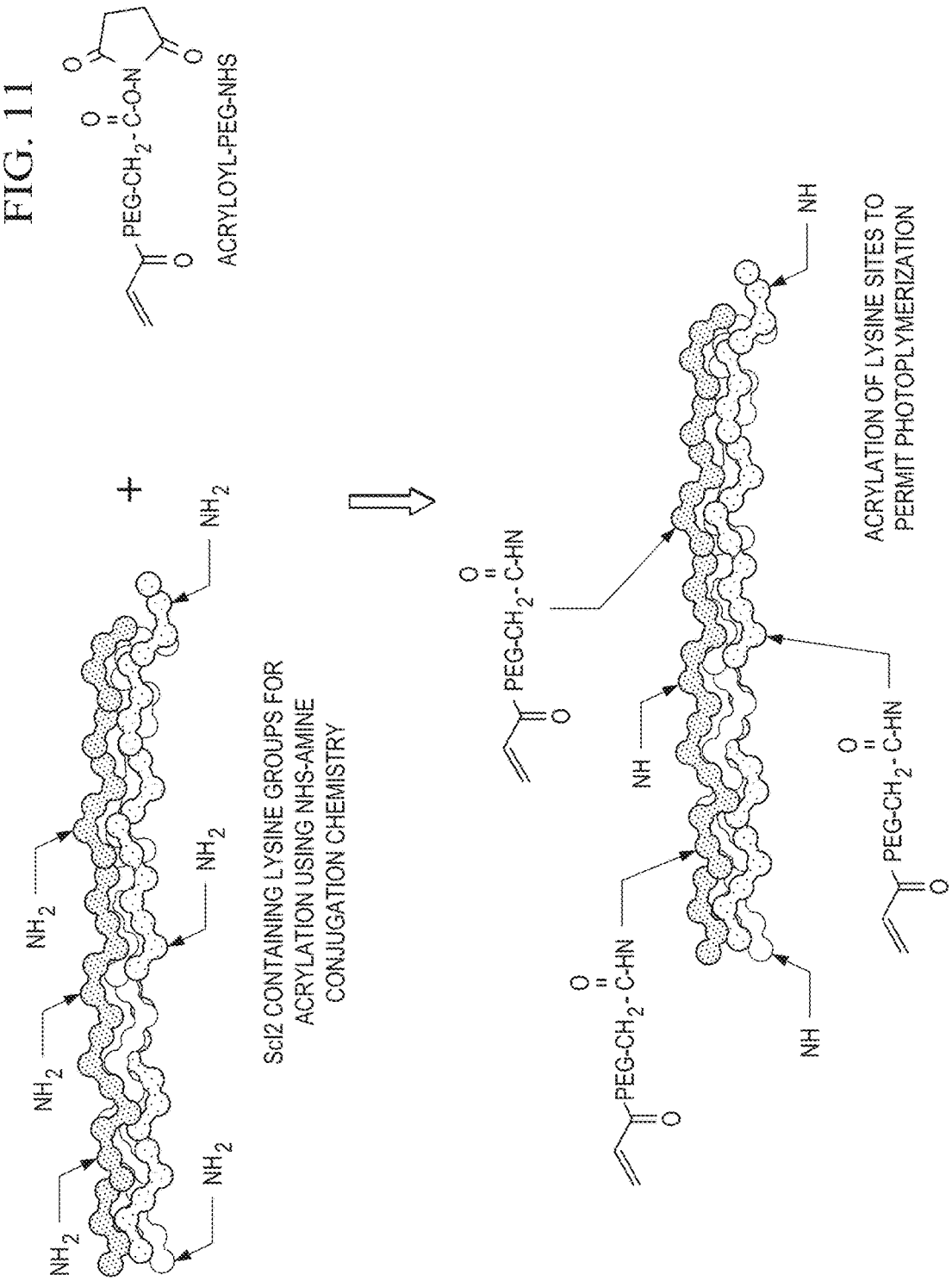
FIG. 11 shows the synthetic route of the functionalization of Designer Collagens (P163, GFPGER (SEQ ID NO:10) containing Designer Collagen, and GFPGEN (SEQ ID NO: 11) containing Designer Collagen) with photoreactive crosslink sites to enable conjugation into PEGDA hydrogels.

Designer Collagen conjugation to PEG linker with photoreactive crosslinks. Designer Collagens and a rat tail collagen I control (Sigma Aldrich) were functionalized with photoreactive crosslink sites to enable hydrogel formation. (FIG. 11). Designer Collagens contain ~9% lysine groups that readily facilitate bioconjugation chemistry via the established NHS-lysine ϵ-amino group reaction. Briefly, proteins were reacted with acrylate-PEG-N-Hydroxysuccinimide (Ac-PEG-NHS, MW 2000) in 50 mM sodium bicarbonate buffer (pH 8.5) at room temperature. A molar ratio of 2:1 Ac-PEG-NHS:$NH_2$ was used and the reaction was allowed to proceed for 18 hours at room temperature with shaking Excess Ac-PEG-NHS and other reaction byproducts were removed via dialysis (MWCO=20,000). Functionalization was confirmed with infrared (IR) spectroscopy and gel electrophoresis.

Example 12

Characterization of functionalized Designer Collagen proteins. Functionalized Designer Collagens were characterized by electrophoresis, circular dichroism, and $\alpha 1$ I domain binding. SDS-PAGE analysis was used to determine multimer formation of 163-F, GFPGER-F (SEQ ID NO: 10), and GFPGEN-F (SEQ ID NO: 11) (F denotes functionalized). Briefly, denatured proteins were incubated at 95° C. for 5 min in the presence of 0.1% SDS and 2% β-mercaptoethanol. Non-denatured samples were incubated in 5% glycerol and kept on ice prior to electrophoresis on 12% SDS-PAGE gels. Gels were stained with coomassie blue, and protein migration as it corresponds to size was determined using protein standards.

Circular dichroism spectra of protein samples in water were recorded on a Jasco J720 spectropolarimeter in a thermostatically controlled cuvette with a 0.5-mm path length. Data was collected in a wavelength range from 250 nm to 190 nm, and integrated for 1 s at 0.2-nm intervals with a bandwidth of 1 nm. For each spectrum, ten scans were averaged and the contribution from the buffer was subtracted. For thermal transition studies, the ellipticity at 220 nm was monitored as the sample temperature was increased from 25 to 45° C., with an average temperature slope of 10° C./hour. Each independently prepared batch of protein was analyzed.

An enzyme-linked immunosorbant assay (ELISA) was utilized to assess the specificity of recombinant $\alpha 1$ I domain binding to control and functionalized Designer Collagens. Microtiter wells were coated with 1 μg per well of P163-F, GFPGER-F (SEQ ID NO: 10), GFPGEN-F (SEQ ID NO: 11), or rat tail derived collagen type I (Cultrex R&D) in PBS containing 1 mM MgCl2 or 1 mM EDTA overnight at 4° C. The samples were blocked with PBS containing 1% BSA (w/v) for 1 hour. Five μM α1 I-domains were added to the wells and incubated for 2 hours at room temperature. A mouse monoclonal anti-his-HRP conjugate (Alpha Diagnostics) was used to detect bound I-domains. The absorbance at 450 nm was measured using a Thermomax plate reader (Molecular Devices Corp, Menlo Park, Calif.). Studies were performed in triplicate.

Example 13

Cell adhesion to functionalized Designer Collagens. To confirm that each Designer Collagen retained appropriate cell interactions following conjugation to PEG, the ability of five distinct cell populations to interact with the functionalized proteins was examined in 2D: 1) C2C12 cells, which do not natively express α1 and α2 subunits; 2) C2C12 cells modified to stably express human α1 subunits (C2C12-α1); (3) C2C12 cells modified to stably express human α2 subunits (C2C12-α2); 4) bovine aortic endothelial cells (ECs); and 5) rat aortic smooth muscle cells (SMCs). Mouse myoblast C2C12, C2C12-α1, and C2C12-α2 cells were provided by Dr. Donald Gullberg (University of Bergen) and maintained in DMEM with 10% FBS (Hyclone) supplemented with no antibiotic, 1 mg/ml geneticin (Invitrogen), or 10 μg/ml of puromycin (InvivoGen), respectively.

For cell adhesion studies, microtiter plates were coated with functionalized and unmodified P163, GFPGER (SEQ ID NO: 10), and GFPGEN (SEQ ID NO: 11). Microtiter wells were coated with 1 μg per well of P163, GFPGER (SEQ ID NO: 10), GFPGEN (SEQ ID NO: 11), or rat tail derived collagen type I (Cultrex R&D) in PBS overnight at 4° C. The Designer Collagen solutions were filter-sterilized using a 0.22 μm PDVF membrane (Millipore) prior to application to the microtiter plate. For each protein, 15 wells (3 wells per cell type examined) were coated. After blocking with PBS containing 1% BSA for 1 hour, the wells were rinsed extensively with PBS and cells were seeded onto the coated surfaces at 6,000 cell/cm2.

Prior to seeding, cells were adapted to serum free media (DMEM containing 1 mM $CaCl_2$ and 1 mM $MgCl_2$) for 3 hours, after which cells were harvested by brief exposure to 0.125% trypsin (Mediatech) and resuspended in serum free media supplemented with 0.2% BSA. Following 3 hour exposure to the coated surfaces at 37° C./5% $CO_2$, cells were fixed with 4% paraformaldehyde and stained with rhodamine phalloidin (Invitrogen) and SybrGreen (Invitrogen). Representative fluorescence images were obtained using a Zeiss Axiovert microscope. Rat tail collagen I coated wells served as positive controls.

Fluorescence images (3 images per sample, 3 samples per protein) of Sybr Green and rhodamine phalloidin stained cells seeded onto coated tissue culture plastic were utilized to quantify the extent of cell adhesion and spreading. The number of cell nuclei per image was used as a quantitative assessment of cell adhesion on each test surface and was assessed by two independent observers. Since different cell seeding densities were employed for various cell types, these cell counts were then normalized to the observed average cell count on the corresponding collagen controls to permit comparison across cell types.

Average cell spreading, or cell area, was quantified by applying the Photoshop "magic wand" tool to the image background and adjusting the tool tolerance so that all extracellular regions were selected. The histogram function was then utilized to evaluate the extracellular pixels. The average pixels per cell (Acell) for that image was then quantified as follows: Acell=(total image pixels−extracellular pixels)/(total image nuclei). Pixels were then converted to microns using known objective scaling. Data are reported as mean±standard error of the mean, p<0.05.

Example 14

Preparation of biologically active PEG-Designer Collagen hydrogels. PEGDA was synthesized by adding acryloyl chloride dropwise to a solution of PEG (3.4 kDa) and triethylamine in anhydrous dichloromethane (DCM) under an argon blanket. The molar ratio of diester, acryloyl chloride, and triethylamine was 1:2.5:2.1, respectively. The reaction was maintained at low temperature to reduce undesired side reactions utilizing a salt/ice bath. After the addition of acryloyl chloride, the reaction was stirred overnight. The resulting solution was washed with 2M K2CO3 to remove acidic byproducts. The DCM phase was subsequently dried with anhydrous MgSO4, and the PEGDA product was then precipitated in diethyl ether, filtered, and dried under vacuum. PEG functionalization was confirmed with IR and NMR spectroscopy. An ester peak at 1704 $cm^{-1}$ and loss of the hydroxyl peak at 3300 $cm^{-1}$ in the IR spectra of PEGDA was indicative of successful acrylation and $^1H$ NMR confirmed an acrylation of ~85%.

Functionalized Designer Collagens were conjugated within PEGDA hydrogels to examine the retention of their specific bioactivities (in terms of cell adhesion) upon incorporation into 3D networks. Proteins were dissolved at 6 mg protein/mL in 20 mM acetic acid. PEGDA powder was then added to each solution to 5 wt %, followed by the addition of 10 μL/mL of a 300 mg/ml solution of UV photoinitiator 2,2-dimethoxy-2-phenyl-acetophenone in N-vinylpyrrolidone. The resulting solutions were sterile-filtered, pipetted between glass plates separated by 200 μm spacers, and polymerized by 10 min exposure to longwave UV light (~6 mW/cm2, Spectroline). The resulting hydrogels were then immersed in PBS for 24 h. C2C12, C2C12-α1, C2C12-α2, EC, and SMC were harvested, resuspended in media containing 10% FBS, and seeded onto the swollen Designer Collagen-containing gels at 6,000 cell/cm2. After 3 hours at 37° C./5% CO2, cells were fixed with paraformaldehyde and stained with rhodamine phalloidin and SybrGreen. Representative fluorescence images were obtained using a Zeiss Axiovert microscope. Rat tail collagen I-containing hydrogels served as positive controls.

3 images per sample per protein of SybrGreen and rhodamine phalloidin stained cells seeded on to PEGDA hydrogels were utilized to quantify the extent of cell adhesion and spreading. The number of cell nuclei per image was used as a quantitative assessment of cell adhesion on each test surface and was assessed by two independent observers. Average cell spreading, or cell area, was quantified by applying the Photoshop "magic wand" tool to the image background and adjusting the tool tolerance so that all extracellular regions were selected. The histogram function was then utilized to evaluate the extracellular pixels. The average pixels per cell (Acell) for that image was then quantified as follows: Acell=(total image pixels−extracellular pixels)/(total image nuclei). Pixels were then converted to microns using known objective scaling. Data are reported as mean±standard error of the mean, p<0.05.

The utility of Designer Collagens was demonstrated in vascular applications by functionalizing Designer Collagens to permit their conjugation into PEGDA hydrogel networks. The ability to functionalize Designer Collagens without disrupting the native conformation, integrin binding affinity, and cell interactions of Designer Collagens was shown.

Example 15

Figure 12:
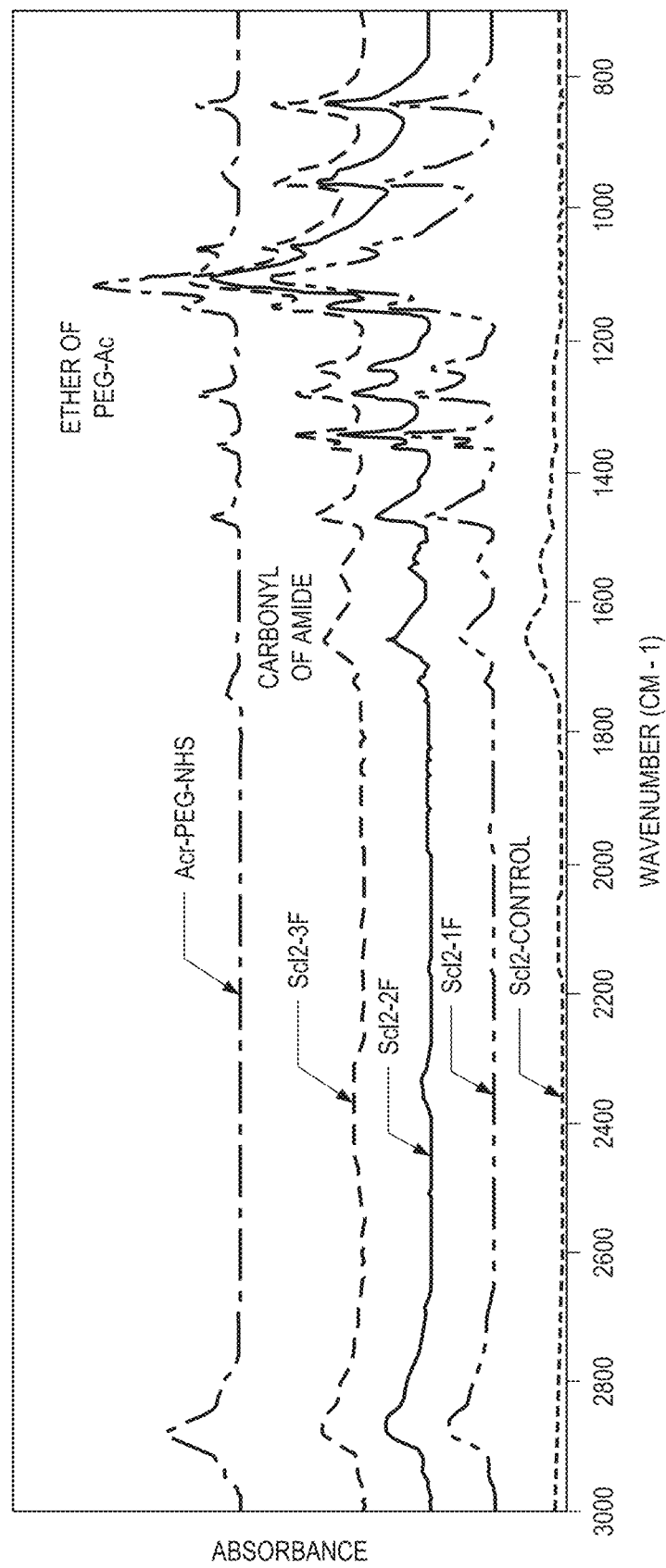
FIG. 12 shows the infrared spectra of functionalized Designer Collagens confirming conjugation of Designer Collagens with PEG-Ac linker.
Figure 13A:
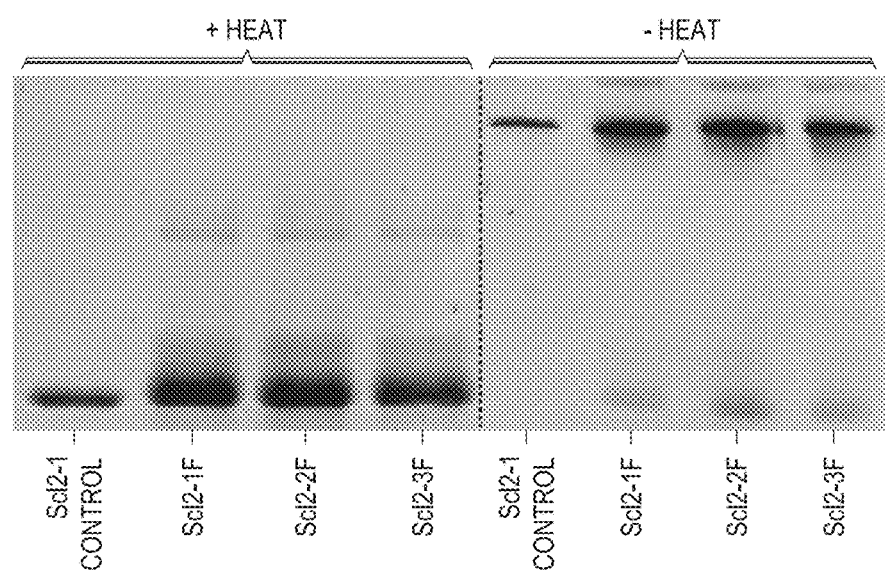
FIGS. 13A-13C show that that functionalized Designer Collagens retained their triple helical conformation and biological activity.

Confirmation of Designer Collagens functionalization. The functionalized proteins, denoted –F, were first analyzed using IR spectroscopy. IR absorbance peaks assigned to the peptide (amide, C=O) at 1630 cm-1 and PEG (ether, C—O—C) at 1110 cm-1 were both present in the purified product, (FIG. 12). Control studies confirmed that non-bonded PEG was removed by dialysis over the selected time period; thus, the presence of PEG in the product was concluded to be coupled to the Designer Collagens and collagen control. The ratio of the peak amide-to-peak ether absorbance was used to standardize the level of functionalization for each batch. As an additional confirmation of functionalization, collagen and Designer Collagens exposed to Ac-PEG-NHS were heat denatured and run on a native SDS-PAGE gel. The smeared bands associated with the products as compared to the unmodified controls confirmed conjugation and gave insight into polydispersity (FIG. 13A). Reduced electrophoretic mobility was attributed to increased molecular weight upon conjugation to the photoreactive PEG linker.

Example 16

Figure 13B:
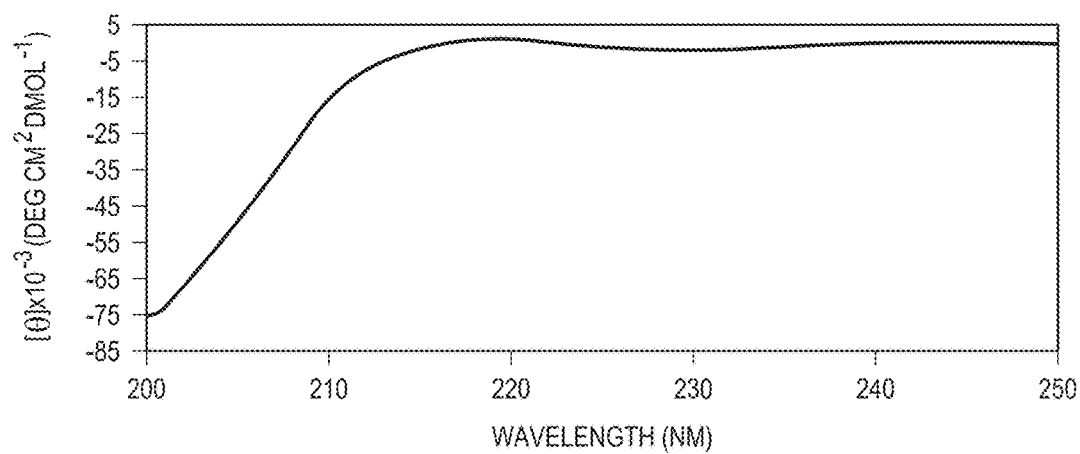
Figure 13C:
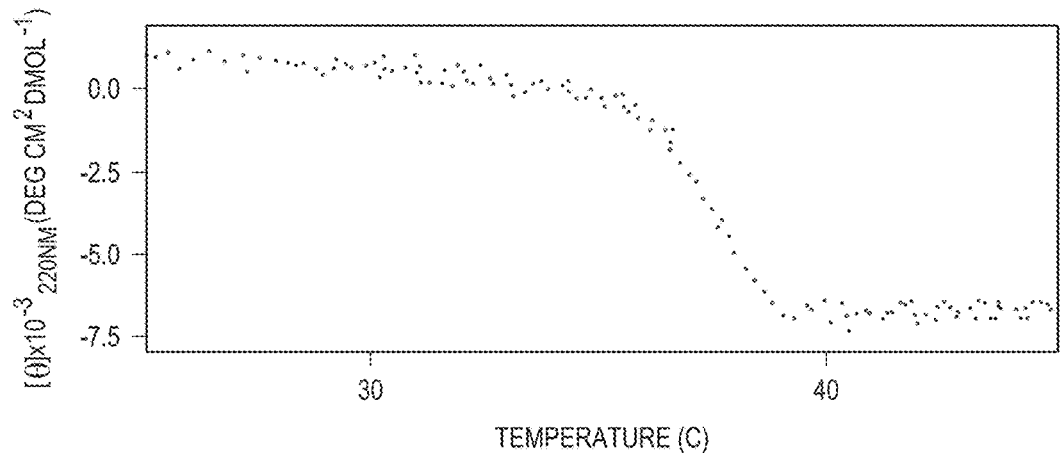

Maintenance of triple helical structure and bioactivity following PEGylation. Extensive protein functionalization can disrupt protein conformation and adhesion site availability. It was therefore important to confirm that Designer Collagens retained their triple helical conformation and biological activity. Designer Collagens ran as homogeneous trimers, with an estimated molecular weight of ~120 kDa, under non-denaturing electrophoretic conditions, in comparison to their heat-denatured counterparts, which exhibited molecular masses of ~35 kDa (FIG. 13A). Retention of a triple helical conformation by Designer Collagens-F was assessed by circular dichroism. P163-F spectra were analyzed and exhibited peaks at 220 nm indicating the presence of a triple helical structure (FIG. 13B). The thermal stability of P163-F triple helices was also monitored, and observed thermal transitions were similar for both P163 and P163-F proteins (FIG. 13C).

Figure 14:
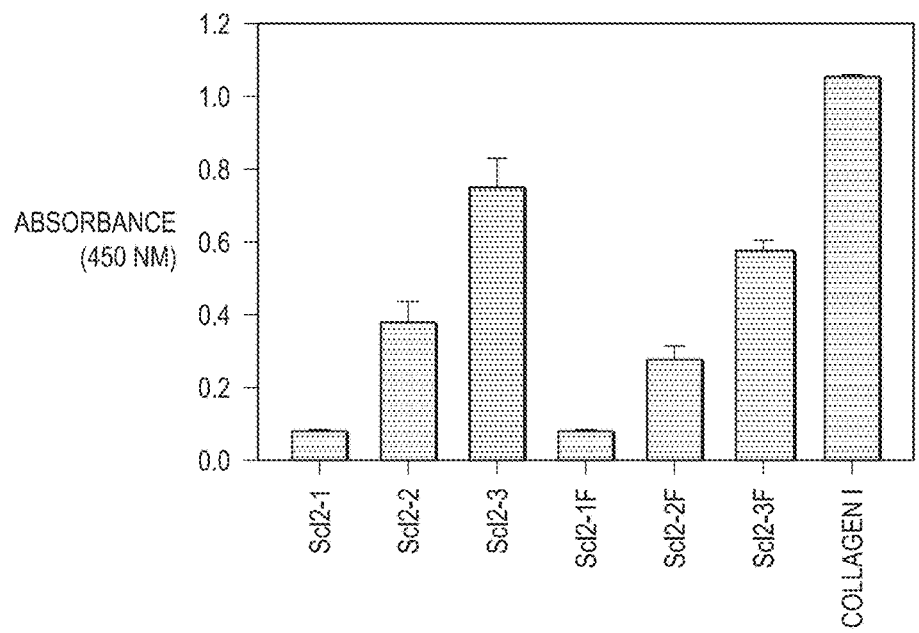
FIG. 14 shows microtiter plates were coated with Designer Collagens and functionalized Designer Collagens at a concentration of 1 mg/well. Recombinant α1 I-domains (5 μM) were allowed to adhere for 2 h and ELISA was performed to quantify integrin binding.

Retention of expected bioactivity was qualitatively evaluated by solid phase binding assays. Microtiter wells were coated with unmodified P163, GFPGER (SEQ ID NO: 10), GFPGEN (SEQ ID NO: 11), P163-F, GFPGER-F (SEQ ID NO: 10), GFPGEN-F (SEQ ID NO: 11) or collagen type I and exposed to recombinant human α1 I-domains. As expected, P163 bound minimal α1 I domains levels and collagen type I bound maximal α11 levels (FIG. 14). Furthermore, GFPGER (SEQ ID NO: 10) and GFPGEN (SEQ ID NO: 11) bound α1 I-domain at levels intermediate between collagen I and P163. Similar trends were observed with functionalized Designer Collagens, which indicated that appropriate integrin binding was retained on functionalization.

Example 17

Figure 15A:
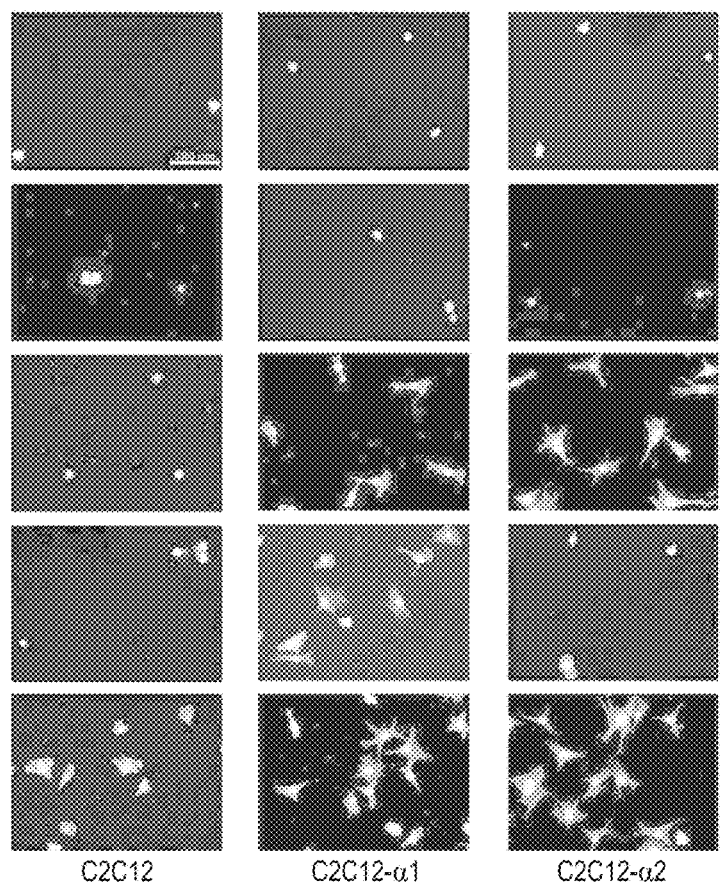
FIG. 15A shows that high binding polystyrene 96 well plates were coated with BSA, P163-F, GFPGER-F (SEQ ID NO:10), GFPGEN-F (SEQ ID NO:11), and functionalized type I collagen (collagen-F) at 1 μg protein per well. C2C12, C2C12-α1, C2C12-α2 cells were seeded at a density of 6000 cell/cm2 and allowed to spread for 3 hours. Attached cells were fixed with 4% paraformaldehyde, stained with rhodamine phalloidin (for F-actin) and SybrGreen (nucleus), and imaged by fluorescence microscopy. Scale bar applies to all images and equals 100 μm.
Figure 15B:
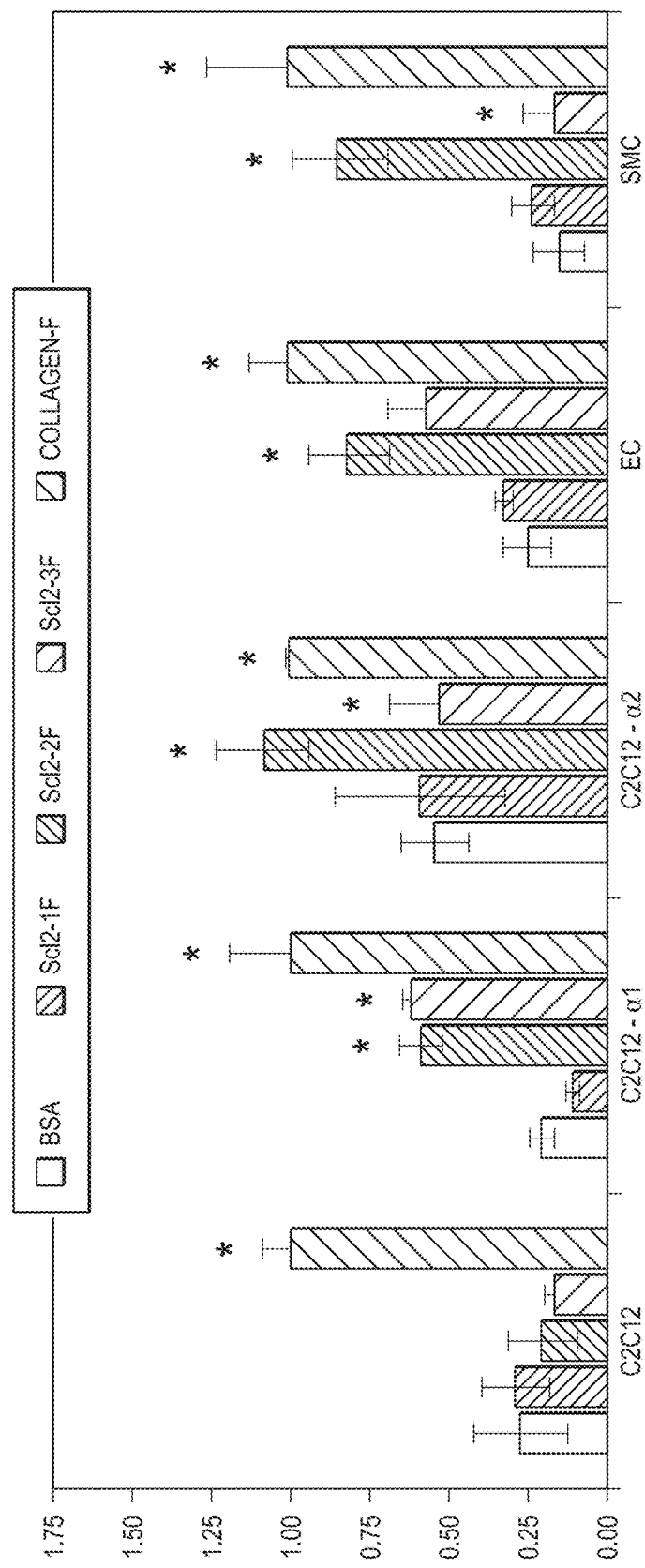
FIG. 15B shows relative cell adhesion on Scl2-F versus collagen-coated tissue culture polystyrene. *, indicates a statistically significant different with the corresponding BSA control, p<0.05.

Cell adhesion to functionalized Designer Collagens. To confirm that cells could recognize and bind the integrin binding motifs in Designer Collagen-F proteins, cell adhesion and spreading studies were performed using mouse C2C12 cells that were modified to express human integrin α1 subunit, C2C12-α1, or human integrin α2 subunit, C2C12-α2. The expression of α1 or α2, and α1 subunits on the cell surface of the cells was confirmed by immunocytochemistry prior to cell culture studies. C2C12, C2C12-α1, or C2C12-α2 were allowed to adhere and spread for 3 hours on microtiter plates coated with 1 µg protein per well. GFPGER-F (SEQ ID NO: 10) and GFPGEN-F (SEQ ID NO: 111) induced spreading of C2C12-α1 (FIG. 15A, second column), as did the collagen-F positive control. However, C2C12-α2 cells (FIG. 15A, third column), adhered and spread on GFPGER-F (SEQ ID NO: 10) and collagen-F but not on GFPGEN-F (SEQ ID NO: 11). These results were consistent with the known integrin binding of each protein. As expected, P163-F coated surfaces displayed similar cell adhesion and spreading as BSA-coated negative controls. FIG. 15B shows that these qualitative assessments were further underscored by quantitative analysis of cell adhesion (BSA, used here as a negative control; Scl2-1F, also referred to as P163-F; Scl2-2F, also referred to as GFPGER-F (SEQ ID NO: 10); Scl2-3F, also referred to as GFPGEN-F (SEQ ID NO: 11), Collagen-F, type I collagen used as a positive control).

Figure 16A:
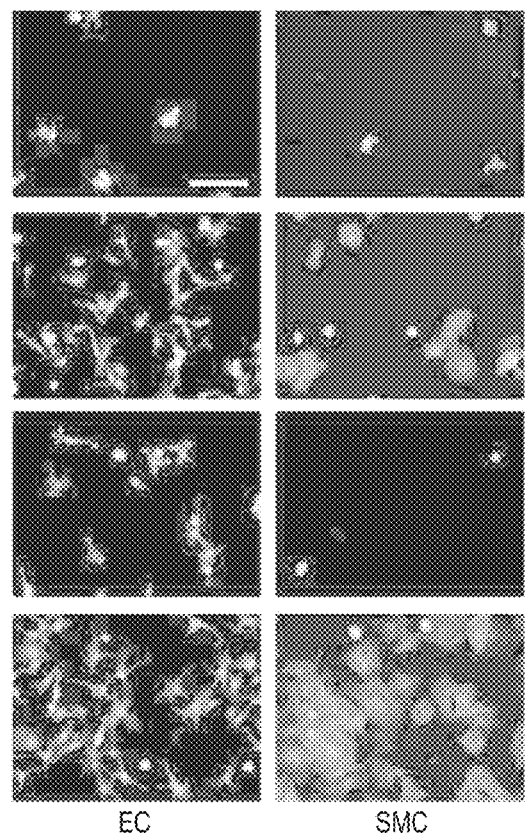
FIG. 16A shows that high binding polystyrene 96 well plates were coated with P163-F, GFPGER-F (SEQ ID NO:10), GFPGEN-F (SEQ ID NO:11), and functionalized type I collagen (collagen-F) at 1 μg protein per well. ECs and SMCs were seeded at a density of 6000 cell/cm² and allowed to spread for 3 hours. Attached cells were fixed with 4% paraformaldehyde, stained with rhodamine phalloidin and SybrGreen, and imaged by fluorescence microscopy. Scale bar applies to all images and equals 100 μm.
Figure 16B:
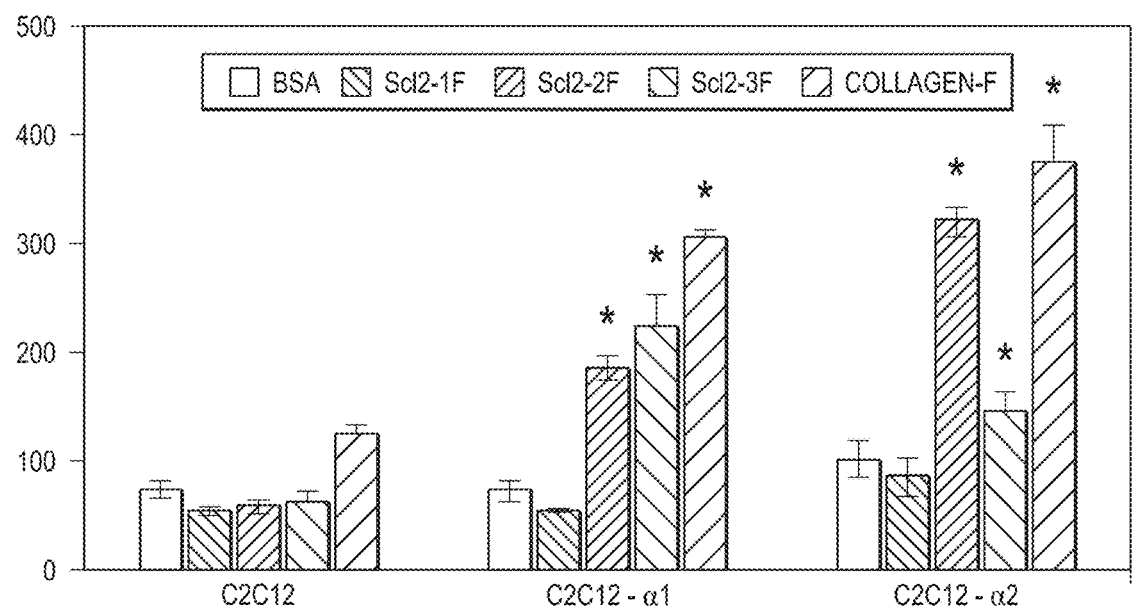
FIG. 16B shows relative cell spreading on Scl2-F versus collagen-coated tissue culture polystyrene. *, indicates a statistically significant different with the corresponding BSA control, p<0.05.

FIG. 16A shows the utility of functionalized Designer Collagens in vascular applications, the attachment and spreading of endothelial cells and smooth muscle cells. Both smooth muscle cells and endothelial cells strongly spread on collagen-F coated surfaces. Furthermore, GFPGER-F (SEQ ID NO: 10) and GFPGEN-F (SEQ ID NO: 11) coated surfaces mediated endothelial cell attachment and spreading, although endothelial cells adhesion on P163-F coated wells was minimal. As with endothelial cells, smooth muscle cells were unable to significantly attach to P163-F. However, in contrast to endothelial cells, smooth muscle cells were able to spread on GFPGER-F (SEQ ID NO: 10) coated surfaces but not on GFPGEN-F (SEQ ID NO: 11) coated wells. Therefore, GFPGER-F (SEQ ID NO: 10) and GFPGEN-F (SEQ ID NO: 11) promoted selective attachment and spreading of endothelial cells versus smooth muscle cells. FIG. 16B shows that these qualitative assessments were further underscored by quantitative analysis of cell spreading (BSA, used here as a negative control; Scl2-1F, also referred to as P163-F; Scl2-2F, also referred to as GFPGER-F (SEQ ID NO: 10); Scl2-3F, also referred to as GFPGEN-F (SEQ ID NO: 11), Collagen-F, type I collagen used as a positive control).

Example 18

Bioactive hydrogels with cell-specific adhesion. Functionalized Designer Collagens were conjugated within 5 wt % PEGDA hydrogels to examine the retention of their specific bioactivities in terms of cell adhesion upon incorporation into 3D networks. PEGDA was selected as the base-material for the hydrogel network due to its established non-thrombogenicity, making these gels particularly desirable for vascular applications. However, the biological blank slate character of PEGDA also allowed observed cell binding to Designer Collagens containing gels to be attributed to the presence of the inserted 'biologically active sequence' alone.

Figure 17A:
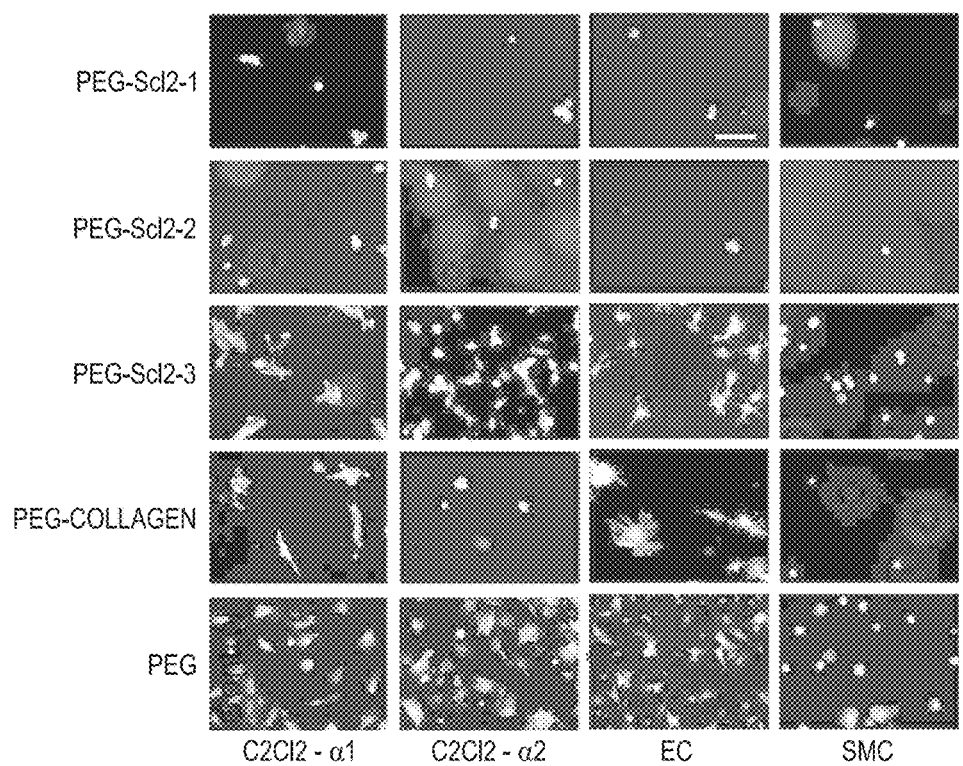
FIG. 17A shows that PEG-Designer Collagen hydrogels were fabricated by combining 5 wt % PEGDA (3.4 kDa) with photoinitiator (Irgacure 2959), 6 mg protein/mL of P163-F, GFPGER-F, GFPGEN-F, or functionalized type I collagen. PEG hydrogels served as a negative control. Cells were seeded at a density of 6000 cell/cm2 and allowed to spread for 3 hours. Attached cells were fixed with 4% paraformaldehyde, stained with rhodamine phalloidin and SybrGreen, and imaged by fluorescence microscopy. Scale bar applies to all images and equals 100 μm.
Figure 17B:
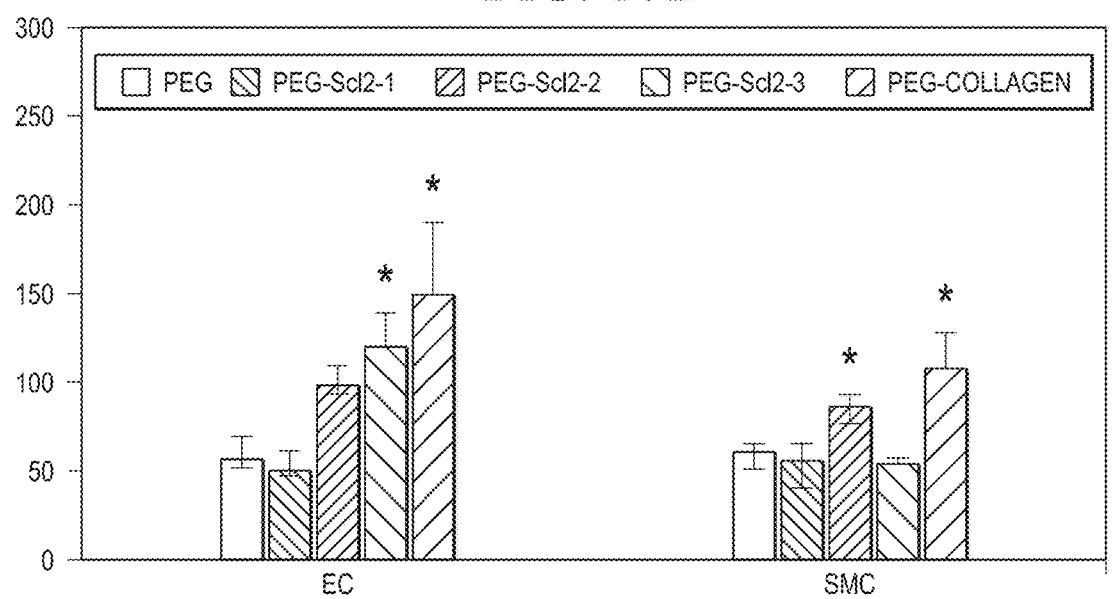
FIG. 17B shows relative cell spreading on PEG-Scl2 gels versus PEG-Collagen gels. *, indicates a statistically significant different with the corresponding PEG control, p<0.05.

Cell adhesion and spreading on the Designer Collagen-based hydrogels was examined using the C2C12-α1, C2C12-α2, endothelial cells, and SMCs, FIG. 17A. As anticipated, each cell type spread on collagen-F coated surfaces, although the extent of their spreading on the gel surfaces was significantly lower than on the collagen-F coated polystyrene well. This observation is consistent with studies demonstrating a reduction in cell spreading with decreasing substrate stiffness. Similarly, GFPGER-F (SEQ ID NO: 10) promoted adhesion of C2C12-α1, C2C12-α2, endothelial cells, and SMCs. GFPGEN-F (SEQ ID NO: 11) gels, however, were unable to support C2C12-α2 and SMC adhesion, as can be seen by comparison with P163-F gels and PEGDA negative controls. FIG. 17B shows that these qualitative assessments were further underscored by quantitative analysis of cell spreading (BSA, used here as a negative control; PEG-Scl2-1, also referred to as P163-F gels; PEG-Scl2-2, also referred to as GFPGER-F (SEQ ID NO: 10) gels; PEG-Scl2-3, also referred to as GFPGEN-F (SEQ ID NO: 11) gels, PEG-Collagen, type I collagen used as a positive control). Thus, functionalized Designer Collagens can be incorporated into 3D matrices to generate cell selective, bioactive hydrogels.

Tissue engineered vascular graft clinical outcomes could be significantly improved by limiting two primary complications associated with vascular grafts, namely thrombosis initiated by platelet adhesion and hyperplastic ingrowth of smooth muscle cells. The ability to differentially bind specific cells is therefore critical to the tissue engineered vascular graft field, where endothelial cell attachment is needed to provide a bioactive blood-graft interface but attachment of blood cells and vessel wall cells is undesired. This is a challenging problem because most scaffolds promote cell attachment through a layer of adsorbed serum proteins that enable the non-selective adhesion of a range of cell types. In the current study, a novel biomaterial platform is disclosed that does not rely upon adsorbed proteins for cell adhesion and thus can be manipulated to promote selective cell interactions.

Designer Collagens were functionalized with photocrosslinking sites to enable incorporation into a three dimensional hydrogel matrix. Bioactive hydrogels were then fabricated by combining the functionalized Designer Collagens with PEGDA and photocrosslinking via exposure to UV light. The P163 protein forms a stable triple helix similar to native collagen but lacks collagen's intrinsic cell-binding sites. As demonstrated herein, endothelial cells and smooth muscle cells are unable to significantly adhere to P163 containing hydrogels. Thus, the P163 protein provided a blank slate into which binding motifs specific to α1β1 and α2β1 integrins could be inserted in a controlled manner while maintaining the triple helical structure of native collagen. Characterization studies confirmed that the functionalization of Designer Collagens did not disrupt triple helix conformation, integrin binding, or cell adhesion. Initial cell studies also confirmed differential endothelial cell and smooth muscle cell adhesion to GFPGER (SEQ ID NO: 10) and GFPGEN-based hydrogels (SEQ ID NO: 11) due to selective integrin binding. In particular, the GFPGEN (SEQ ID NO: 11) based hydrogels were found to selectively promote adhesion of endothelial cells but not of smooth muscle cells. Since Designer Collagens are non-thrombogenic in terms of platelet aggregation, the spatial localization of various modified Designer Collagens within tissue engineered vascular graft scaffolds may prove to be a powerful tool for promoting luminal endothelial cell adhesion while inhibiting thrombosis and intimal hyperplasia.

The present invention describes the development of semisynthetic hydrogels that contain Designer Collagens having tunable mechanical properties and controllable bioactivity. Bacterial expression of recombinant Designer Collagens enables a level of batch consistency and economies of scale not possible with solid phase synthesis or native collagen extraction. Conjugation of the Designer Collagens within a synthetic PEG network permits the impact of Designer Collagens on cell behavior to be explored within a mechanically stable hydrogel network and broadens the range of mechanical properties available in the hydrogel design. The present invention describes the use of Designer Collagen Hydrogels (DCH) with properties that recruit selective cell adherence and spreading dependent on the integrin-binding motif included in the Designer Collagen. Cell selectivity is therefore based on the cell's collagen-binding integrin profile. Designer Collagen Hydrogel-1 (or referred to as P163-F) does not contain an integrin binding motif and therefore, does not support optimal adherence or spreading. Designer Collagen Hydrogels-2 (or referred to as GFPGER-based hydrogels (SEQ ID NO: 10)) contains α11 and α12 binding sites. Because of the widespread expression profiles of the collagen-binding integrins, Designer Collagen Hydrogel-2 is an optimal biomaterial for the adherence of many cell types. Designer Collagen Hydrogel-3 (or referred to as GFPGEN-based hydrogels (SEQ ID NO: 11)) contains GFPGEN (SEQ ID NO: 11), which selectively binds α1, but not α2.

Representative uses of Designer Collagen Hydrogels include but are not limited to 1) vascular applications, 2) hernia repair, 3) adhesion prevention, 4) wound healing, 5) cell delivery, 6) bone formation and healing, 7) cartilage replacement, and 8) breast augmentation. Generally, vascular products include grafts, patches, shunts, catheters and stents. Study of Designer Collagen in combination with hydrogels has resulted in a platform of formulations that direct endothelial cell adhesion and growth while minimizing the potential for thrombosis, intimal hyperplasia, and mechanical failure. Accordingly, the present invention contemplates that Designer Collagen hydrogels may be usefully incorporated into, for example, 1) vascular patches for carotid endarterectomy, dialysis access, bypass functions, and aneurysm treatment; 2) vascular grafts for bypass functions and dialysis access; 3) vascular stenting such as angioplasty or carotid stenting for the treatment of aneurysms, weak vascular, and flow blockage, shunts, which are used in a variety of situations to reroute blood flow; and 4) vascular catheters, for venous access in patients.

Abdominal wall defects may require surgical repair surgery using the tissue or in combination with a medical device, such as mesh. Current mesh-type products, including both synthetic and biological, could be coated with Designer Collagen hydrogels which would provide the cell-material interface. The Designer Collagen hydrogel mesh would be designed to have specific cell-interacting areas and areas that minimize cell-interactions.

Adhesions are scar-like tissues that form between peritoneum surfaces when the normal mesothelial cell layer is perturbed. Efforts to prevent adhesion formation post-surgery are based on barriers or pharmaceuticals. Barrier efforts have resulted in mesh-types and gel-types. Cell types that have been implicated in adhesion formation include myofibroblasts, endothelial cells, and inflammatory cells with wound healing functions. Designer Collagen hydrogels with decreased modulus would function as a gel and be appropriate for laparoscopy procedures. Designer Collagen hydrogels would contain P163, which does not contain any ligand binding sites and therefore, would not allow cell recruitment to the area. The application of Designer Collagen hydrogels to the damaged area would act as a barrier in the colonization of cells that may facilitate adhesion formation.

Wound healing applications may include chronic or acute wounds or superficial wounds. Adult mesenchymal stem cells (MSCs) are being investigated for their use in regenerative medicine as these cells have the capacity to differentiate into: osteogenic, chondrogenic, adipogenic, myogenic, and neurogenic lineages. Efforts to utilize mesenchymal stem cells in localized areas for tissue growth have met challenges, such as cell retention. Cell retention must be achieved without alteration of the mesenchymal stem cell phenotype, allowing the influx of host factors to the mesenchymal stem cells, and by the support structure being tolerated by existing host tissues. Designer Collagen hydrogels can interact with collagen-binding integrins on the mesenchymal stem cell surface and would therefore function as an optimal cell retention material. Also, directing mesenchymal stem cells towards a specific phenotype has proved challenging. Designer Collagen hydrogels can be used to induce specific cell differentiation by altering the Designer Collagen content and also the properties of the hydrogel itself. Designer Collagens also are a substrate for the adherence of adipocyte stem cells.

The protein, DC3 (containing integrin binding sequence, GFPGEN (SEQ ID NO: 11)), possesses a unique characteristic in that it binds $\alpha 1\beta 1$ integrin on the cell surface, but not $\alpha 2\beta 2$. This specific protein-integrin interaction is what determines cell binding specificity, i.e., endothelial adhesion and spreading with minimal smooth muscle cell spreading and a lack of thrombosis. This property gives Designer Collagen hydrogels-3 an advantage in vascular device applications. The protein, DC2 (containing integrin binding sequence, GFPGER (SEQ ID NO: 10)), possesses the ability to act as a support for a wide variety of cell types. This characteristic is important when anastomosis of tissue with a device is warranted. An example of this is hernia mesh. DC2 or Designer Collagen hydrogel-2 coated on a mesh would allow for cell adherence and in growth on and around the mesh, and the mesh would contribute support in terms of strength and suture capability.

DC1(P163) is a triple helical protein that does not support the adherence of any cell type tested. This is advantageous because a triple helical protein is resistant to many proteases, thereby, remaining in the body for a longer period of time. This would be appropriate for adhesion prevention therapies. A gel-like substance of DC1 or DCH-1 would not allow the adherence of cells that would eventually lay down fibrotic material.

Figure 18:
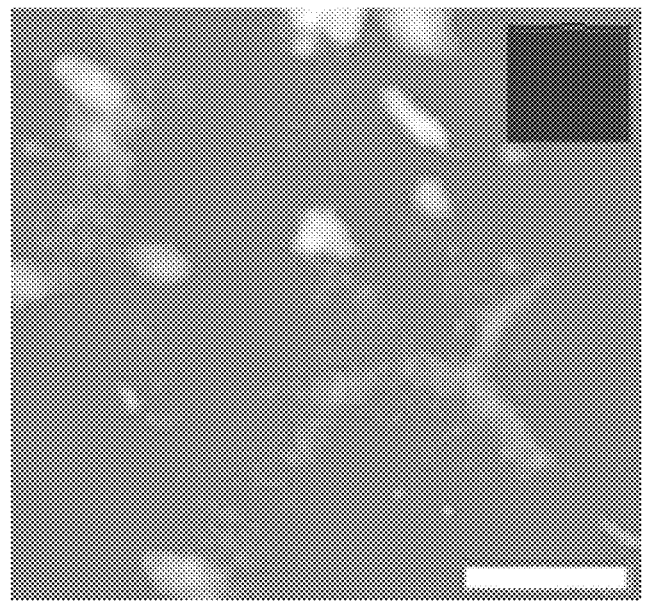
FIG. 18 shows that Designer Collagen Hydrogels with encapsulated MSCs remain viable. Mesenchymal stem cells were mixed with the PEG-DA (polyethylene (glycol) Diacrylate) (3400 g/mol) dissolved in buffer (10 wt %), a photoinitiator (Irgacure 2959) and 1 mg/mL of AC-PEG-DC2 (also referred to as GFPGER-F (SEQ ID NO:10)). The solution was then crosslinked via 90 s exposure to 365 nm UV light (UV-Transilluminator, 9 mW/cm²) and viability assessed after 24 hours using a standard Live-Dead kit. MSCs encapsulated within the gel network rapidly spread within the matrix.
Figure 19:
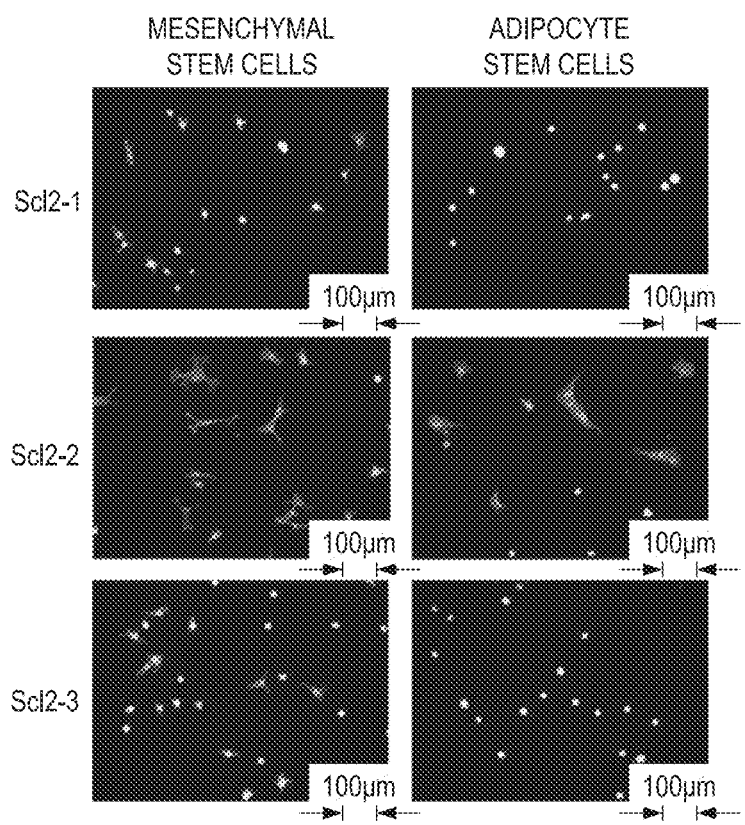
FIG. 19 shows high binding polystyrene 96-well plates coated with P163 (Scl2-1), GFPGER (Scl2-2), and GFP-GEN (Scl2-3) at 1 μg protein per well. Mesenchymal stem cells and adipocyte derived stem cells were seeded and allowed to adhere for 3 hours. Attached cells were fixed with 4% paraformaldehyde, stained with rhodamine phalloidin and SybrGreen, and imaged by fluorescence microscopy.
Figure 22:
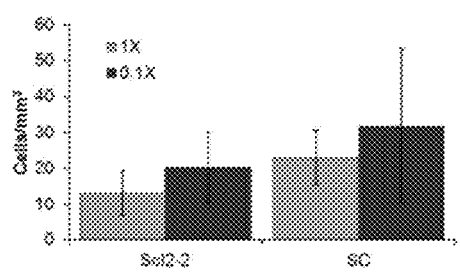
FIG. 22 is a plot of cell adhesion on PEG diacrylamide PEGDAA gels and shows the high functionalization density of SCM had similar adhesion to the low functionalization density of Scl2-2.

Hydrogels with encapsulated MSCs remain viable. To ensure that cells remained viable while encapsulated in DC hydrogels, mesenchymal stem cells were mixed with the PEG-DA dissolved in buffer, a photoinitiator and AC-PEG-DC2. The solution was then crosslinked via exposure to UV light and viability assessed. MSCs encapsulated within the gel network rapidly spread within the matrix. In addition, Live-Dead staining of mesenchymal stem cells (MSC) encapsulated in PEG-Designer Collagen gels indicated that these gels and the associated polymerization process are cytocompatible (FIG. 18). FIG. 19 shows that both MSC and adipocyte stem cells can adhere and spread on GFPGER (SEQ ID NO: 10), but that MSC adhere and spread on both GFPGER (SEQ ID NO: 10) and GFPGEN (SEQ ID NO: 11).

Collagens are abundant extracellular matrix proteins and play a major role in the structural integrity of many tissues. In addition, collagens regulate cell functions through interactions with cellular receptors and extracellular matrix constituents. There are at least 28 different mammalian collagens classified as homotrimeric or heterotrimeric depending on the identity of their 3 polypeptide chains. Each polypeptide chain contains continuous GXY motifs, where G is a glycine amino acid, X is often a proline amino acid and Y is usually a hydroxyproline residue. Because of its small size, every glycine is found embedded in the center of the triple helical structure and allows the chains to pack tightly into a stable left-handed triple helix. Proline hydroxylation and protein glycosylation of lysine residues are important in overall triple helix stability and collagen network formation.

Collagen is a commonly used biomaterial due to its structure and bioactive cues. Animal-derived collagen is currently used in medical devices because current methods of obtaining recombinant collagens are not commercially viable and synthetic collagen peptides have limited quantities and are cost prohibitive. In addition, animal-derived materials have inherent disease risk and batch variability. Bacterial originated collagens are triple helical proteins lacking hydroxyproline that are stabilized by charged residues and have been recently characterized as potentially useful biomaterials. Their production and purification from bacterial expression systems allows for batch conformity and scale-up without the need for post translation modification of proline. Scl2, a bacterial collagen from *Streptococcus pyogenes* is a candidate for biomaterial applications. Scl2 contains a N-terminal globular domain followed by a collagen-like region composed of GXY repeats, where X is often proline or a charged residue that provides helix stability. Bacterial collagens have limited capabilities in forming networks and are therefore limited. Since bacterial protein engineering is possible in reasonable time frames, Scl2 possess an additional advantage in that it can be engineered with specific cellular and biomechanical properties.

Ligands for Scl2 have not been identified and therefore this triple helical blank slate has been used to introduce mammalian collagen sequences. The collagen recognition sequences of heparin, integrins ($\alpha 1\beta 1$, $\alpha 2\beta 1$, $\alpha 11\beta 1$), and matrix metalloproteinases have been identified and when subsequently introduced into the Scl2 blank slate, provide bioactivity to Scl2. Integrins are cell surface heterodimers that enable outside in and inside out cell signaling. The introduction of the integrin motifs GFPGEN (SEQ ID NO: 11) and GFPGER (SEQ ID NO: 10), enabled Scl2 to be a cell selective substrate based on integrin recognition profiles. Cell instruction could be useful in biomedical application development.

Poly(ethylene glycol) (PEG) hydrogels are a widely used biomaterial due to their biocompatibility and highly tunable properties. PEG hydrogels are inherently resistant to protein adsorption and cell adhesion, which permits controlled introduction of bioactive agents and corollary control of cell interactions. The present disclosure provides Streptococcal collagen-like protein (Scl2) coupled into PEG-based hydrogels utilizing conjugation chemistry. Specifically, the Lys residues of Scl2-2 were conjugated to a photo-crosslinkable PEG linker for incorporation into PEG hydrogels. The addition of a hydrogel network to the bacterial collagen provides a tunable network where material properties can be altered (i.e. modulus, degradation, and compliance). The degree of functionalization has an effect on cell:material interactions where a higher degree of functionalization imparted steric hindrance of the integrin binding site. Sufficient functionalization is required to maintain protein within hydrogels over time as a result too little functionalization results in protein loss and therefore a loss of cell: material interactions.

The present disclosure provides a designed bacterial collagen based on Scl2$_{GFPGER}$. This protein was designed to decrease steric hindrance of functionalization and increase helix stability. The present disclosure presents data to demonstrate an increase in triple helix melting temperature. The present disclosure shows that this increase in stability results in an increase in integrin affinity. The location of linkers on the collagen-like domain effects integrin availability and therefore cell adhesion and spreading rates. The construction of this novel collagen, stable collagen-mimetic (SCM), demonstrates that bacterial collagens can be altered in numerous ways to achieve very specific properties.

In addition to the creation of a new protein with novel characteristics, the present disclosure provides data indicating that Scl2-2 (triple helical protein with GFPGER (SEQ ID NO: 10) integrin binding site) contributed to wound closure at faster rates than untreated controls. Dose dependent effects were observed when comparing a high (5 mg/ml) and a low dose (0.5 mg/ml).

Protein engineering: Recombinant SCM protein was derived from Scl2 containing integrin binding motif GFPGER (SEQ ID NO: 10) at positions 118-123. The C-terminus of Scl2 contains regions where triple helix is predicted to be less stable and contributes to a lower melting temperature (algorithm used to predict collagen stability is described in Persikov, A., Ramshaw, J. A., and Brodsky, B., J. Biol. Chem (2005): Prediction of collagen stability from amino acid sequence). Using this algorithm GXY triplets were identified that contribute to protein stability and selected triplets were mutated to more stable triplets. To generate a more thermally stable collagen, two triplets GKDGKD (SEQ ID NO: 27) were mutated to GDRGER (SEQ ID NO: 28) (Lys314→Asp314, Asp315→Arg315, Lys317→Glu317, Asp318→Arg318) where D and E at X position and R in Y position of GXY triplet are predicted to be more stable. To stabilize functionalization of Scl2GFPGER single Lys residues were replaced by Arg residues in GKD triplets at Lys positions 182, 236, 248, 263, 269, 275, 278, 284, 290, 293, 299, 305, 308, and 323 (the Arg at the X position of a GXY triplet exist at same frequency in eukaryotic collagens as replaced Lys residues and are similarly thermally stable). The mutations were introduced by gene synthesis (Genewiz). Recombinant proteins were expressed in E. coli Top3 cells and purified by affinity chromatography on a 5 ml column (GE Healthcare). Protein purity was determined by SDS-PAGE followed by Coomassie blue staining and western blot analysis. SDS-PAGE analysis was used to determine multimer formation of Scl2 and derivatives proteins as described. Briefly, proteins were denatured by incubation at 95° C. for 5 minutes in the presence of 0.1% SDS and 2% β-mercaptoethanol. Non-denatured samples were incubated in 5% glycerol and kept on ice prior to electrophoresis on 12% SDS gels. Gels were stained with Coomassie blue, and protein migration as it corresponds to size was determined using protein standard.

Circular dichroism: Circular dichroism spectra of protein samples in 20 mM Acetic acid were recorded on a Jasco J720 spectropolarimeter in a thermostatically controlled cuvette with a 0.5-mm path length. Data was collected at ambient temperature in a wavelength range from 250 nm to 190 nm, and integrated for 1 second at 0.2-nm intervals with a bandwidth of 1 nm. For each spectrum, ten scans were averaged and the contribution from the buffer was subtracted. For thermal transition studies, the ellipticity at 220 nm was monitored as the sample temperature was increased from 25 to 50° C., with an average temperature slope of 10° C./hour.

Solid phase binding assays. Microtiter wells were coated with 1 μg per well of prokaryotic collagens or rat tail derived collagen type I in 20 mM Acetic acid overnight at 4° C. The samples were blocked with HEPES containing 1% bovine serum albumin (BSA) for 1 hr. 5 μM α1 domain was added to the wells and incubated for 1 hour at room temperature. A mouse monoclonal anti-FLAG conjugate followed by goat-anti mouse-HRP. SigmaFast OPD was used to detect bound I-domains. The absorbance at 450 nm was measured using a Thermomax plate reader.

Protein Functionalization: Scl2-2 and SCM were then functionalized with acrylate-PEG-N-hydroxysuccinimide (Acr-PEG-NHS) with varying ratios of PEG:NH$_2$ (1:1, 0.1:1) to produce proteins with high and low PEG linker densities (1x; 0.1x). Bioactive hydrogels were fabricated by combining the functionalized proteins with (10% w/v) PEG-diacrylamide (3.4 kDa) solutions and exposing to UV light to initiate crosslinking.

Endothelial Cell Interactions: ECs were seeded onto the swollen gels at 10,000 cells/cm$^2$. After 3 hours, cells were fixed and stained with rhodamine phalloidin, and Sybr-Green. Cell images were obtained using a fluorescent microscope and used to quantify EC adhesion and spreading.

Stable Collagen-mimetic Structural Characterization: To generate one embodiment of a more useful collagen-like protein, 2 aspects were considered: 1) thermal stability, 2) residue location for functionalization. To produce a thermally stable collagen, two triplets, GKDGKD, were mutated to GDRGER. To tailor functionalization of Scl2-2 away from the integrin binding motif, 14 single Lys residues were replaced by Arg residues in GKD triplets. Arg at the X position of GXY triplets exists at the same frequency in eukaryotic collagens as replaced Lys residues and are similarly thermally stable. The mutations were introduced by gene synthesis (Genewiz) and the protein named, stable collagen-mimetic (SCM).

FIGS. 20A and 20B are circular dichroism spectra of SCL2-2 and SCM. The peak at 220 nm in the plot is indicative of the formation of a triple helix structure. FIG. 20C is a plot of the thermal transitions of Scl2-2 (red crossing 0 at 36) and SCM (green crossing 0 at 42). The engineered SCM protein was purified by affinity chromatography and circular dichroism was used to determine the protein's secondary structure. FIGS. 20A and 20B, showed a typical triple helical spectra with a characteristic peak at 220 nm indicating the triple helical nature of SCM. A marked increase in melting temperature from 37° C. to 45° C. was observed in thermal transition studies, FIG. 20C. These results indicated that protein stability predictions may be used to stabilize the triple helices and that selective triplet substitutions may be used to optimize the backbone helix to achieve certain properties.

Stable Collagen-Mimetic Binds alpha1 With Enhanced Affinity: A triple helical conformation is required for integrin binding and activation. ELISA type assays were used to determine that SCM can bind alpha1. The interaction between SCM and alpha1 is a higher affinity interaction when compared to Scl2-2. This indicates that modulation of the triple helical backbone can affect ligand interactions and potentially cellular behavior. The present disclosure demonstrates that intact cellular integrins are ligands for SCM, by using mouse myoblast C2C12 cells expressing single collagen-binding integrins.

FIG. 21 is a graph of cell adherence of collagen mimetics to substrates for $C_2C_{12}$ cell adherence. (sDC2=SCM, DC2=Scl2-2, DC1=Scl2). FIG. 21 shows the levels of cell adhesion to various substrates and indicates that SCM is able to serve as a cell attachment substrate through integrin binding. In addition to SCM binding alpha1beta1 expressing cells, cells expressing alpha2beta are able to adhere to SCM substrate.

Fibronectin Binding of SCM: Fibronectin (Fn) is an extracellular matrix protein that interacts with collagen using a discreet binding motif. The mammalian collagen Fn binding motif is present at the C-terminal end of SCM. The ability of SCM to bind Fn was shown using ELISA-type assays. SCM binds Fn in the dose dependent and saturable manner to show that multiple motifs can be engineered within one SCM without altering ligand interactions. These data lend the possibility of mixing and matching motifs to enhance a cellular interaction.

SCM incorporation into PEG-hydrogels: FTIR spectroscopy confirmed successful functionalization of Scl2-2 and SCM with low and high densities of PEG linkers. The functionalized protein spectra contained absorption peaks corresponding to the carbonyl of the amides (~1650 $cm^{-1}$) in the protein backbone and ether (~1110 $cm^{-1}$) of PEG linker. There was a marked increase in cellular adhesion on the SCM gels.

FIG. 22 is a plot of cell adhesion on PEGDAA gels and shows the high functionalization density of SCM had similar adhesion to the low functionalization density of Scl2-2. EC spreading was comparable for Scl2 2 and SCM at the 0.1× functionalization density. However, spreading for the 1× functionalization density was increased for SCM gel.

The present disclosure illustrates the modification of the Scl2-2 protein into a new protein that can be used to generate bioactive hydrogels. The modification of the SC protein enhanced both stability and cell interactions with the bioactive hydrogel. The present disclosure provides a designer collagen platform for engineering a completely unique collagen, relevant to a broad range of devices and therapeutics. To our knowledge, this is not possible with any other system.

Collagen is a commonly used biomaterial for tissue regeneration due to its ability to regulate cell behavior through interactions with α1β1 and α2β1 integrins. However, it is far from an ideal substrate given its multitude of biological cues, significant batch variability, rising concerns regarding immunogenicity, and disease risk associated with contaminants. The instant disclosure circumvents these limitations by generating novel bioactive materials using a collagen mimetic protein engineered to have enhanced therapeutic action and improved scale-up potential.

One embodiment of the present invention provides a collagen-mimetic protein is based on Scl2 from *Streptococcus pyogenes* that incorporates human integrin binding sites into the Scl2 protein and the human integrin binding sites function within the engineered protein to bind and activate α1β1/α2β1. This "Designer Collagen" has several advantages: 1) triple helical protein, 2) introduction of multiple and specific biological cues, 3) consistent batch-to-batch properties, 4) relatively resistant to enzymatic degradation, 5) suitable for large-scale purification, 6) thermally more stable than mammalian collagen, and 7) non-cytotoxic and non-immunogenic. The present invention also includes biosynthetic hydrogels based on these Designer Collagens. The recombinant nature of Designer Collagen also allows for genetic engineering of a variety of aspects, such as: A) nature, spacing and specificity of biological cues, B) stability, half-life and tissue targeting, and C) optimization of manufacturing, protein architecture or product properties.

One embodiment of the present invention provides a stable bacterial triple helix that retains its cell instructive cues the melting temperature is increased from 37° C. to about 42° C. Another embodiment of the present invention provides maximized functionalization by introducing hydrogel cross-liking residues away from biologically active motifs.

The present invention provides a synthetic methodology to functionalize designer collagen with photocrosslinking sites to enable incorporation into hydrogel matrices that enables 3D properties. Hydrogel integrated Designer Collagen greatly expands the potential applications beyond the traditional uses for collagen in soft tissue repair. These matrices provide a wide range of geometries, matrix mechanics, and degradation rates that can be tuned to match application design criteria. The present disclosure relates to small-diameter vascular grafts, chronic wound dressings, and matrices for bone and cartilage regeneration.

For example, diabetic foot, pressure, and venous ulcers have a 25% lifetime incidence rate and chronic wound cost burden is a staggering $25 billion. Using conventional first-line treatments such as debridement, offloading, and moist saline dressings, a 40% wound size reduction in 4 weeks is considered promising. Subsequent treatments such as skin substitutes, negative pressure wound therapy, and hyperbaric oxygen treatment dramatically increase treatment cost and do not have impressive closure rates. Current second-line treatments offer a 12% increase in closure rates, bringing only ~⅓ of wounds to closure. Current dermal substitutes are fraught with problems limiting clinical success. A skin substitute is a common second-line therapy yielding modest 30% closure rates compared to saline gauze at 18%. Given that diabetic ulcers are increasing at a rate of 2.8%, the clinical and economic burden of chronic ulcers necessitates an improved first-line treatment that provides efficient wound closure while remaining cost effective. The mechanism of healing using skin substitutes is multifaceted but likely relies on a combination of extracellular matrix (ECM) physical properties and embedded biological cues. Since the basis of deriving skin substitute components relies on harvesting mammalian ECM components such as collagen, fibronectin or acellular ECM, there is little to no opportunity for optimizing the inherent properties of these materials, and they are manufactured with a disclaimer of disease risk. Since they are rather ineffective, frequent applications of skin substitute dressings increase patient pain and cost. Current efforts towards improving chronic wound dressings are focused on infection prevention, which is important but does not achieve the ultimate goal of healing the wound. A first-line therapeutic dressing capable of transitioning these chronic wounds back to acute wound healing processes is not available and would fulfill a clear unmet need for a growing diabetic population.

One embodiment of the present invention can modulate both the physical properties and the biological cues of native ECM to enhance wound closure in a cost effective dressing. This biomimetic dressing is a first-line therapy option to offer superior wound closure rates by engaging integrins to attract and instruct cells. Integrin-mediated wound closure: Integrins facilitate wound healing by serving as cell anchors during infiltration of non-resident cells, migration of keratinocytes and fibroblasts, angiogenesis, and myofibroblast contraction. α1β1 and α2β1 integrins are key players in the wound healing process. α1β1 regulates fibroblast proliferation, collagen synthesis (COLL), and angiogenesis whereas α2β1 increases fibroblast contraction and adhesion and increases keratinocyte and endothelial cell migration. The collagen-binding integrins, α1β1 and α2β1, recognize specific 6-residue motifs (e.g. GFO/PGER) that must be presented in a triple helical structure.

One embodiment of the present invention provides a collagen mimetic protein as a vehicle for the presentation of these motifs is a, Scl2 from *Streptococcus pyogenes*. Although, integrin signaling is not the only event leading to wound closure, our preliminary studies in a rodent excisional wound model demonstrated that soluble application of Scl2 containing an integrin-binding site increased wound closure rates.

In one embodiment, a modified Scl2, termed Designer Collagen, is incorporated into a biodegradable hydrogel matrix, which offers tunable degradation, rheological, and mechanical properties. These hydrogels are then formulated into microspheres providing an amorphous gel-like dressing that is conformable to wound shape offering immediate hydration balance and infection protection to the wound, while over time allowing cellular infiltration into the microsphere network through Designer Collagen, which will attract and instruct cells through integrin binding. This wound dressing harnesses the specific bioactivity in a biodegradable hydrogel matrix to provide a product that balances exudate and wound hydration, promotes cell migration and proliferation, and degrades at an appropriate rate to eliminate the need for frequent dressing changes.

The wound dressing of the present invention is innovative because it uses a biomaterial based on the bacterial protein Scl2 from *Streptococcus pyogenes*. Scl2.28 was the first bacterial collagen-like protein described and shares many key characteristics with mammalian collagen including forming a triple helix. Importantly for its use as a biomaterial, it is relatively resistant to enzyme degradation and is non-cytotoxic. An exciting advantage of the bacterial collagen mimetic is that it is a "blank slate" lacking the array of binding sites for cells and proteins that are present in mammalian collagens. This allows for directed engineering to introduce specific biological cues. Site directed mutagenesis introduced human integrin binding sites into Scl2 (termed Scl2-2) and provided evidence that human integrin binding sites function within Scl2-2 to bind and activate $\alpha1\beta1/\alpha2\beta1$. The capability of introducing a single biologically active motif allows a direct and undiffused message to the cell as opposed to native collagen where multiple motifs are present. A specific motif can also be presented multiple times with defined spacing in a single bacterial collagen. Multiple integrin binding sites enhance the cell's behavior on the scaffold. Scl2 has been described as non-immunogenic since injection of soluble protein did not elicit a robust immune response regardless of the addition of adjuvant. Subcutaneous implants of Scl2-2-PEG hydrogels did not elicit a robust host response and histopathology of the implants was unremarkable. The Scl2-2 platform provides a unique opportunity to investigate the contribution of collagen binding integrins to wound healing. In an effort to increase triple helical stability and increase protein functionalization (discussed below), a novel protein based on Scl2-2, termed Designer Collagen. Designer Collagen contains a single human integrin-binding site as its built-in biological cue and exhibits an increased melting temperature. The melting temperature is one key to making sure the triple helix remains intact since this conformation is required for cellular interactions. An ELISA based binding assay shows an increased binding of $\alpha1$ I-domain to Designer Collagen compared to Scl2-2 and demonstrates that this engineered protein binds similar to collagen type 1.

Novel Biomaterial Platform PEG-Designer Collagen Hydrogels: Designer Collagen is a valuable tool for controlling integrin binding, but cannot form stable 3D scaffolds and is limited by solubility. To remedy this, the present invention provides a synthetic methodology to functionalize collagen-like proteins with photocrosslinking sites to enable incorporation into hydrogel matrices, which allows for finer control of delivery, bioactivity, and improved solubility. This was the first time that collagen-like proteins were incorporated into a 3D matrix, which enables their use in medical device and tissue engineering applications. The present invention provides tunable biodegradation and microsphere fabrication as new features to our bioactive hydrogel system. Poly($\beta$ amino ester) (PAE) and poly(ethylene glycol) (PEG) were selected for the hydrogel base to provide a system with tunable swelling and degradation kinetics. It is well established that excess wound fluid and degradation rates affect cellular functions such as cell adhesion, migration, and differentiation; however, these properties are poorly controlled in current human/animal derived dermal substitutes, which are often milled with heterogeneous size distributions and properties with inherent disease and immunological risks. Described here, microsphere geometry allows for a conformable dressing with enhanced cell migration and the ability to tailor the bioactivity, swelling, and biodegradation rate.

The present disclosure provides the treatment for wounds and more specifically diabetic wounds that have an inherent imbalance in ECM deposition/turnover and cell recruitment and migration by introducing integrin binding motifs in Designer Collagen PEG-PAE hydrogel microspheres as a way to kick-start the wound healing process. PEG-PAE hydrogels have highly tunable swelling and degradation rates to provide enhanced moisture control. The formation of hydrogel microspheres allows a conformable dressing that can be easily implemented into the clinic similar to microparticle/hydrocolloid dressings. The uniformity of microsphere size provides control of viscosity and degradation as compared to the highly variable particle size of animal derived products.

The present invention includes Designer Collagen microspheres with controlled swelling/degradation properties. PAE was selected due to its promising cytocompatibility and rapid degradation rate, which is tunable independent of crosslink density and associated gel properties by substituting a fraction of the biodegradable PAE macromer with a hydrolytically stable PEG-based macromer of comparable molecular weight. PAE macromers were synthesized by PEG-diacrylate (PEGDA, 400 g/mol) was stirred with 3-methoxypropylamine (3MOPA) for 48 hours at 85° C., and the resulting PAE was quenched at 4° C. Macromer molecular weight was modulated by varying the molar ratio of diacrylate to amine from 2:1 to 4:3 resulting in molecular weights from approximately 400 to 1,000 Da. The final product chemical structures were verified using $^1$HNMR spectroscopy. Biodegradable hydrogels were synthesized by combining the PAE macromer (0-100%) with PEGDA (10 kDa) at a constant total macromer concentration of 10%. Swelling ratios of photopolymerized hydrogels were measured in PBS and 0.015 M NaOH (accelerated hydrolysis) to monitor degradation rate. This library of biodegradable hydrogels was fabricated and tested to elucidate the effect of compositional variables on degradation rate and to generate hydrogels with a range of degradation rates from hours to months.

Designer Collagen of the instant invention can be introduced into 3D PEG networks by functionalization with acrylated-PEG linkers. Designer Collagen was incorporated into PEG-PAE hydrogels, and viability, adhesion, and spreading of human dermal fibroblasts (hDFs) was found to be comparable to tissue culture polystyrene controls at 24 hours. Adhesion and spreading were significantly increased relative to PEG-PAE control gels. It is well-established that cell phenotype and migration are influenced by receptor-ligand binding affinity and ligand concentration. Increased cell adhesion, spreading and migration is seen with increased ligand density (protein concentration in bioactive hydrogels).

Microspheres were fabricated using a standard emulsification protocol including 5 vol % aqueous phase (10 wt % PEGDA-10 kDa, 1 wt % Irgacure) was dispersed in hexane (1 wt % Span80/Tween80) by vortexing. Hydrogel microspheres were photopolymerized while stirring for 6 minutes using 365 nm light and purified by multiple hexane washes and vacuum-drying. The effect of microsphere concentration (mg of dry mass/ml of water) on viscosity was investigated using a cone plate rheometer. Microsphere suspensions with concentrations ranging from 2-65 mg/ml were produced with viscosities between 1,700-104,000 cP. Microsphere suspensions with viscosities between 2,000 cP (honey) and 10,000 cP (molasses) were selected for ease of handling.

In vitro degradation studies in simulated wound fluid (0.68 g NaCl, 0.22 g KCl, 2.5 g of $NaHCO_3$, and 0.35 g of $NaH_2PO_4$ in 100 ml of distilled water) were characterized to verify degradation of microspheres in approximately 6 weeks. Microsphere degradation was measured using mass loss of lyophilized samples and rheology to monitor changes in viscosity of swollen, degrading microspheres. Iterative selections are contemplated based on established relationships between compositional variables and degradation rates until the target rate is achieved. The water uptake of the final microsphere formulation is characterized to determine a range of swelling volumes that result in viscosities between 2,000 and 10,000 cP. Upon verification of PEG-PAE hydrogel degradation rate, Designer Collagen at a low (1 mg/ml) and high (8 mg/ml) concentration are functionalized with Acr-PEG-NHA linkers and incorporated into PEG-PAE microspheres. Microspheres will then be characterized using 3D in vitro studies of cell-material interactions. Cell viability of primary human dermal fibroblasts, epidermal keratinocytes, and dermal microvascular endothelial cells are measured at 24 and 72 hours to confirm that high viabilities are maintained with the microspheres (>90%). Cell adherence is assessed at 3 and 24 hours to determine initial effects of Designer Collagen concentrations by crystal violet assays.

Biodegradable microsphere formulations may have a viscosity range 2,000-10,000 cP and achieve full dissolution in simulated wound fluid of in 4-6 weeks and display over 90% cell viability after 72 hours of all relevant cell types for wound healing. Cell adhesion and spreading on Designer Collagen microspheres will be within 20% of corresponding PEG-collagen controls. The present invention provides hydrogel and microsphere that are tunable by several methods to tune both degradation rate and viscosity if needed.

In one example, a rat excisional wound model was used to evaluate integrin contribution to wound healing. Soluble Scl2-2, a collagen-like protein with integrin binding sites but without stability optimization, at a 0.5 mg/ml (low) or a 5 mg/ml (high) concentration was applied to wound beds every other day for 14-days and wound closure was analyzed. After a single application, a 5% and 8% increase in closure in the low- and high-Scl2-2 treated wounds was observed, respectively. On the eighth day, high-Scl2-2 treated wounds were 13% more closed than PBS treated wounds and at the conclusion the high-Scl2-2 treated wounds were 50% more closed than the low and PBS treated wounds. These data indicate that integrin binding contributes to wound closure and that Scl2-2 is an appropriate vehicle for their presentation.

The wound is immediately splinted and covered with a semi-occlusive dressing in order for repair mechanisms to recapitulate those used in humans rather than rodents. Similar to humans, splinted rodent wounds heal primarily by granulation tissue formation and epithelialization rather than contraction. Using this model, the contribution of integrin binding to wound healing is evaluated by comparing the effect of DCMs to DCMsΔintegrin, with the inclusion of IFM, a clinically relevant control.

In addition, the present invention evaluates changes in gene expression using a Wound Healing PCR Array from SABiosciences. Array target genes include growth factors, inflammatory cytokines and chemokines, collagens, integrins, and extracellular matrix proteases and their inhibitors. A total of 84 unique genes are targeted, many of which have dysregulated expression in chronic diabetic wounds, including matrix metalloproteinase genes, which can be regulated by $α2β1$.

Figure 23:
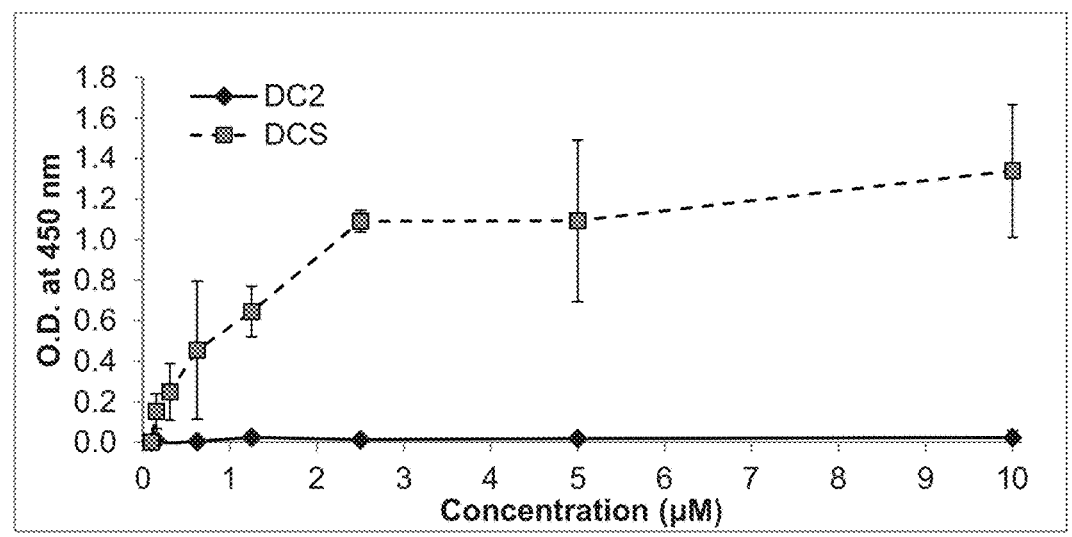
FIG. 23 is a plot showing DC2 (Scl2 with GFPGER (SEQ ID NO:10)) and DCS (Scl2 backbone modified to have increased stability and a Fn binding motif).

FIG. 23 is a plot showing DC2 (Scl2 with GFPGER (SEQ ID NO: 10)) and DCS (Scl2 backbone modified to have increased stability and a Fn binding motif). The plot was made from data from microtiter plates that were coated with Fn and increasing amounts of DC2 or DCS were added to the wells. Binding was detected by OD at 450 nm and shows a saturable and dose dependent curve.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing"

(and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

Xu et al. J Biol Chem 2000 Dec. 15; 275(50):38981-38989.
Kim et al. J Biol Chem 2005 Sep. 16; 280(37):32512-32520.
Xu Y, J Biol Chem 2002 Jul. 26; 277(30):27312-27318.
Humtsoe et al. J Biol Chem 2005 Apr. 8; 280(14):13848-13857.
Sweeney et al. J Biol Chem 2003 Aug. 15; 278(33):30516-30524.
Han et al. Appl Microbiol Biotechnol. 2006 Mar. 22: (72) 109-115.
Mohs et al. J Biol Chem 2007 Oct. 12: 282(41)29757-29765.
Hoe et al. FEMS Microbiology 2007 Oct. 24: (277)142-149.
Yoshizumi, et al. Protein Sci. 2009 June; 18(6):1241-51.
Caswell, et al. J Biol Chem. 2008 Dec. 26; 283(52):36168-75.
FDA, Federal Register. Department of Health and Human Services 2007, 72, (8), 1581-1619.
Yu et al. Protein Sci. 2010, 19, (4), 775-85.
Yu et al. J Biol Chem. 2011, 286, (21), 18960-8.
Yoshizumi et al. Protein Sci. 2009, 18, (6), 1241-51.
Xu et al. J Biol Chem. 2002, 277, (30), 27312-8.
Seo et al. J Biol Chem. 2010, 285, (40), 31046-54.
Peng et al. Biomaterials 2010, 31, (10), 2755-61.
Peng et al. Microbial cell factories 2012, 11, 146.
Mohs et al. J Biol Chem. 2007, 282, (41), 29757-65.
Hoe et al. FEMS microbiology letters 2007, 277, (2), 142-9.
Han et al. Applied microbiology and biotechnology 2006, 72, (1), 109-15.
Cosgriff-Hernandez et al. Acta biomaterialia 2010, 6, (10), 3969-77.
Browning et al. Biomaterials 2011, submitted.
Persikov et al. The Journal of biological chemistry 2005, 280, (19), 19343-9.
Ko et al. Plastic and reconstructive surgery 2011, 127 Suppl 1, 10S-20S.
An et al. Biomaterials 2013, 34, (2), 402-12.
Yu et al. J Biol Chem. 2012, 287, (27), 22988-97.
Browning et al. Biomacromolecules 2013, 14, (7), 2225-33.
Shi et al. J Biol Chem. 2012, 287, (42), 35139-52.

What is claimed is:

1. A synthetic collagen that facilitates wound closure comprising:
   an isolated and purified triple helical backbone protein that facilitates the wound closure comprising:
   one or more alterations in a triple helical backbone protein sequence comprising charged residues without hydroxyproline that stabilize the isolated and purified triple helical backbone protein, wherein the one or more alterations do not disrupt an additional collagen ligand interaction and do not bind or activate platelets; wherein the altered triple helical backbone protein sequence has been modified to comprise two or more GFPGER (SEP ID NO: 10) integrin binding motifs that binds an integrin α1, wherein the isolated and purified triple helical backbone protein facilitates the wound closure.

2. The synthetic collagen of claim 1, wherein the isolated and purified triple helical backbone protein is produced in a prokaryotic expression system.

3. The synthetic collagen of claim 1, wherein the triple helical backbone is derived from a Streptococcal protein.

4. The synthetic collagen of claim 1 wherein the synthetic collagen is formulated with a topical carrier to form a topical composition.

5. The synthetic collagen of claim 1, wherein the collagen ligand is an integrin.

6. The synthetic collagen of claim 5, wherein the collagen ligand is an integrin α1β1.

7. The synthetic collagen of claim 1, wherein the isolated and purified triple helical backbone protein has a higher melting temperature than an unmodified triple helical backbone protein.

8. The synthetic collagen of claim 1, wherein the isolated and purified triple helical backbone protein is supported by a matrix.

9. The synthetic collagen of claim 8, wherein the matrix is a polymer matrix.

10. The synthetic collagen of claim 8, wherein the polymer matrix is a Poly(ethylene glycol) hydrogel.

11. The synthetic collagen of claim 8, wherein the matrix is an acellular derived mammalian matrix.

12. The synthetic collagen of claim 1, wherein the isolated and purified triple helical backbone protein is formed into a vascular graft, a wound dressing, or a matrices for bone and cartilage regeneration.

13. The synthetic collagen of claim 1, wherein the isolated and purified triple helical backbone protein is formed into a lumen of a vascular graft.

14. The synthetic collagen of claim 1, wherein the isolated and purified triple helical backbone protein binds a fibronectin.

15. The synthetic collagen of claim 14, wherein the fibronectin is in an acellular matrix derived from mammals.

16. A topical synthetic collagen composition that facilitates wound closure comprising:
   a topical carrier;
   a synthetic and isolated triple helical backbone protein that facilitates the wound closure disposed in the topical carrier, wherein the synthetic and isolated triple, helical backbone protein comprises:
   one or more alteration in the triple helical backbone protein sequence, that stabilize the synthetic and isolated triple helical backbone protein and does not disrupt interaction of integrin $\alpha_1\beta_1$ or integrin $\alpha_2\beta_1$ with collagen and does not bind and activate platelets; wherein the altered triple helical backbone protein sequence has been modified to comprise two or more GFPGER (SEP ID NO: 10) repeats that are integrin binding motifs which bind integrin $\alpha_1$ and have an increased binding affinity for the integrin.

* * * * *

SEQUENCE LISTING

<160> NUMBER OF SEQ ID NOS: 26

<210> SEQ ID NO 1
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is a hydroxyproline

<400> SEQUENCE: 1

Gly Phe Xaa Gly Glu Arg
1               5

```
<210> SEQ ID NO 2
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (3)..(3)
<223> OTHER INFORMATION: Xaa is hydroxyproline

<400> SEQUENCE: 2

Gly Leu Xaa Gly Glu Arg
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic peptide

<400> SEQUENCE: 3

Gly Ala Ser Gly Glu Arg
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide

<400> SEQUENCE: 4

Gly Leu Pro Gly Glu Arg
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic peptide

<400> SEQUENCE: 5

Gly Leu Pro Gly Glu Asn
1               5

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide

<400> SEQUENCE: 6

Gly Leu Pro Gly Glu Lys
1               5

<210> SEQ ID NO 7
<211> LENGTH: 6
<212> TYPE: PRT
<213> ORGANISM: Artificial Sequence
<220> FEATURE:
<223> OTHER INFORMATION: Synthetic peptide

<400> SEQUENCE: 7
```

```
Gly Arg Pro Gly Glu Arg
1               5

<210> SEQ ID NO 8
<211> LENGTH: 6
<212> TYPE: PRT
<213> ORGANISM: Artificial Sequence
<220> FEATURE:
<223> OTHER INFORMATION: Synthetic peptide

<400> SEQUENCE: 8

Gly Arg Pro Gly Glu Asn
1               5

<210> SEQ ID NO 9
<211> LENGTH: 6
<212> TYPE: PRT
<213> ORGANISM: Artificial Sequence
<220> FEATURE:
<223> OTHER INFORMATION: Synthetic peptide

<400> SEQUENCE: 9

Gly Arg Pro Gly Glu Lys
1               5

<210> SEQ ID NO 10
<211> LENGTH: 6
<212> TYPE: PRT
<213> ORGANISM: Artificial Sequence
<220> FEATURE:
<223> OTHER INFORMATION: Synthetic peptide

<400> SEQUENCE: 10

Gly Phe Pro Gly Glu Arg
1               5

<210> SEQ ID NO 11
<211> LENGTH: 6
<212> TYPE: PRT
<213> ORGANISM: Artificial Sequence
<220> FEATURE:
<223> OTHER INFORMATION: Synthetic peptide

<400> SEQUENCE: 11

Gly Phe Pro Gly Glu Asn
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic peptide

<400> SEQUENCE: 12

Gly Phe Pro Gly Glu Lys
1               5

<210> SEQ ID NO 13
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
```

```
<220> FEATURE:
<221> NAME/KEY: MISC_FEATURE
<222> LOCATION: (5)..(5)
<223> OTHER INFORMATION: Xaa is Leu, Arg or Phe
<220> FEATURE:
<221> NAME/KEY: MISC_FEATURE
<222> LOCATION: (6)..(6)
<223> OTHER INFORMATION: Xaa is Pro
<220> FEATURE:
<221> NAME/KEY: MISC_FEATURE
<222> LOCATION: (8)..(8)
<223> OTHER INFORMATION: Xaa is Glu
<220> FEATURE:
<221> NAME/KEY: MISC_FEATURE
<222> LOCATION: (9)..(9)
<223> OTHER INFORMATION: Xaa is Arg, Lys or Asn
<220> FEATURE:
<221> NAME/KEY: MISC_FEATURE
<222> LOCATION: (11)..(12)
<223> OTHER INFORMATION: Xaa is any amino acid

<400> SEQUENCE: 13

Gly Xaa Xaa Gly Xaa Xaa Gly Xaa Xaa Gly Xaa Xaa
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 14

Gly Xaa Xaa Gly Leu Pro Gly Glu Arg Gly Xaa Xaa
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 15

Gly Xaa Xaa Gly Leu Pro Gly Glu Asn Gly Xaa Xaa
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
```

```
<220> FEATURE:
<221> NAME/KEY: misc_feature
<222> LOCATION: (11)..(12)
<223> OTHER INFORMATION: Xaa can be any naturally occurring amino acid

<400> SEQUENCE: 16

Gly Xaa Xaa Gly Leu Pro Gly Glu Lys Gly Xaa Xaa
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 17

Gly Xaa Xaa Gly Arg Pro Gly Glu Arg Gly Xaa Xaa
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 18

Gly Xaa Xaa Gly Arg Pro Gly Glu Asn Gly Xaa Xaa
1               5                   10

<210> SEQ ID NO 19
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 19

Gly Xaa Xaa Gly Arg Pro Gly Glu Lys Gly Xaa Xaa
1               5                   10

<210> SEQ ID NO 20
<211> LENGTH: 12
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 20

Gly Xaa Xaa Gly Phe Pro Gly Glu Arg Gly Xaa Xaa
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 21

Gly Xaa Xaa Gly Phe Pro Gly Glu Asn Gly Xaa Xaa
1               5                   10

<210> SEQ ID NO 22
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 22

Gly Xaa Xaa Gly Phe Pro Gly Glu Lys Gly Xaa Xaa
1               5                   10

<210> SEQ ID NO 23
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (2)..(2)
<223> OTHER INFORMATION: Xaa is Leu, Arg or Phe
<220> FEATURE:
<221> NAME/KEY: MISC_FEATURE
<222> LOCATION: (3)..(3)
<223> OTHER INFORMATION: Xaa is Pro
<220> FEATURE:
<221> NAME/KEY: MISC_FEATURE
<222> LOCATION: (5)..(5)
<223> OTHER INFORMATION: Xaa is Glu
<220> FEATURE:
<221> NAME/KEY: MISC_FEATURE
<222> LOCATION: (6)..(6)
```

```
<223> OTHER INFORMATION: Xaa is Arg, Lys or Asn

<400> SEQUENCE: 23

Gly Xaa Xaa Gly Xaa Xaa
1               5

<210> SEQ ID NO 24
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 24

Gly Xaa Xaa Gly Leu Pro Gly Glu Arg Gly Xaa Xaa
1               5                   10

<210> SEQ ID NO 25
<211> LENGTH: 18
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 25

Gly Xaa Xaa Gly Leu Pro Gly Glu Arg Gly Xaa Xaa Gly Leu Pro Gly
1               5                   10                  15

Glu Arg

<210> SEQ ID NO 26
<211> LENGTH: 27
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(3)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid

<400> SEQUENCE: 26

Gly Xaa Xaa Gly Leu Pro Gly Glu Arg Gly Xaa Xaa Gly Leu Pro Gly
1               5                   10                  15

Glu Arg Gly Xaa Xaa Gly Leu Pro Gly Glu Arg
            20                  25
```